US007790377B2

(12) United States Patent
Henrich et al.

(10) Patent No.: US 7,790,377 B2
(45) Date of Patent: Sep. 7, 2010

(54) COMPOUNDS THAT ACT TO MODULATE INSECT GROWTH AND METHODS AND SYSTEMS FOR IDENTIFYING SUCH COMPOUNDS

(75) Inventors: Vincent C. Henrich, Greensboro, NC (US); Cary Alan Weinberger, Carrboro, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 633 days.

(21) Appl. No.: 10/929,090

(22) Filed: Aug. 27, 2004

(65) Prior Publication Data
US 2005/0049230 A1    Mar. 3, 2005

Related U.S. Application Data

(60) Provisional application No. 60/498,847, filed on Aug. 29, 2003.

(51) Int. Cl.
    C12Q 1/68      (2006.01)
    C12N 15/63     (2006.01)
    C07H 21/04     (2006.01)
    C12N 5/00      (2006.01)
(52) U.S. Cl. .......................... 435/6; 435/455; 536/23.4
(58) Field of Classification Search ....................... None
    See application file for complete search history.

(56) References Cited

U.S. PATENT DOCUMENTS

| | | | |
|---|---|---|---|
| 5,849,320 A | 12/1998 | Turnblad et al. | |
| 5,891,431 A | 4/1999 | Palli et al. | |
| 5,942,542 A | 8/1999 | Killick et al. | |
| 6,063,610 A | 5/2000 | Silver et al. | |
| 6,265,173 B1 * | 7/2001 | Evans et al. ............ | 435/7.1 |
| 6,326,165 B1 | 12/2001 | Wilson et al. | |
| 6,333,318 B1 * | 12/2001 | Evans et al. ............ | 514/171 |
| 6,362,394 B1 | 3/2002 | Crossland et al. | |
| 6,586,470 B1 | 7/2003 | Lojek et al. | |
| 6,603,044 B1 | 8/2003 | Tohnishi et al. | |
| 6,617,341 B1 | 9/2003 | Iwataki et al. | |
| 6,630,465 B2 | 10/2003 | Treacy et al. | |
| 6,737,382 B1 | 5/2004 | Iwataki et al. | |
| 2003/0211455 A1 * | 11/2003 | Tran et al. ............ | 435/4 |
| 2008/0020381 A1 | 1/2008 | Henrich et al. | |

FOREIGN PATENT DOCUMENTS

| | | |
|---|---|---|
| WO | WO 91/13167 | 5/1991 |
| WO | WO-98/46724 | 10/1998 |
| WO | WO 99/36520 | 7/1999 |
| WO | WO 01/70816 A2 | 9/2001 |

OTHER PUBLICATIONS

Agric, University of Missouri, Plant Sciences,( Award Type-HATCH .c H), "Characterization of the Upstream Regulator(s) of S6 Kinase and of Ecdysone Receptor Complex (citation)." Printed Aug. 12, 2003.
Allgood, V. et al., "Modulation by Vitamin $B_6$ of Glucocorticoid Receptor-Mediated Gene Expression Requires Transcription Factors in Addition to the Glucocorticoid Receptor." J. Biol. Chem., 1993, vol. 268, No. 28, 20870-20876.
Bak, A. et al., "The Effect of Serum Cholesterol Levels of Coffee Brewed by Filtering and Boiling." N. Engl. J. Med., 1989, vol. 321, No. 21, 1432-1437.
Baker, K. et al., "Transcriptional Activation of the *Drosophila ecdysone* Receptor by Insect and Plant Ecdysteroids." Insect Biochem. Mol. Biol., 2000, 30:1037-1043.
Baker, K. et al., "The *Drosophila* Orphan Nuclear Receptor DHR38 Mediates an Atypical Ecdysteroid Signaling Pathway." Cell, 2003, 113:731-742.
Bender, M. et al. "*Drosophila ecdysone* Receptor Mutations Reveal Functional Differences among Receptor Isoforms." Cell, 1997, 91:777-788.
Biggers, W. et al., "Detection of Juvenile Hormone-Active Compounds by Larvae of the Marine *Annelid capitella* Sp. I." Arch. of Insect Biochem. Physiol., 1996, 32:475-484.
Birkett, M. et al., "New Roles for Cis-Jasmone as an Insect Semiochemical and in Plant Defense." Proc. Natl. Acad. Sci. USA, 2000, vol. 97, No. 16, 9329-9334.
Bonning, B. et al., "Development of a Recombinant Baculovirus Expressing a Modified Juvenile Hormone Esterase with Potential for Insect Control." Arch. Insect Biochem. and Physiol., 1995, 30:177-194.
Bowers, W., "Juvenile Hormone: Activity of Natural and Synthetic Synergists." Science, 1968, vol. 161, No. 3844, 895-897.
Bowers, W., "Juvenile Hormone: Activity of Aromatic Terpenoid Ethers." Science, 1969, vol. 164, No. 3877, 323-325.
Bowers, W. et al., "Juvenile Hormone: Identification of an Active Compound from Balsam Fir." Science, 1966, vol. 154, No. 3752, 1020-1021.
Bowers, W. et al., "Juvocimenes: Potent Juvenile Hormone Mimics from Sweet Basil." Science, 1980, vol. 209, No. 4460, 1030-1032.
Bowers, W. et al., "Discovery of Insect Anti-Juvenile Hormones in Plants". Science, 1976, vol. 193, No. 4253, 542-547.
Bowers, W. et. al., "Natural and Synthetic Allatotoxins: Suicide Substrates for Juvenile Hormone Biosynthesis." Science, 1982, vol. 217, No. 4560, 647-648.
Brooks, G. et al., "The Action of Precocenes in Milkweed Bugs (*Oncopeltus fasciatus*) and Locusts (*Locusta migratoria*)." Nature, 1979, 281:570-572.

(Continued)

*Primary Examiner*—Quang Nguyen
(74) *Attorney, Agent, or Firm*—Kilpatrick Stockton LLP

(57) ABSTRACT

Disclosed are methods and systems for screening for compounds that act to modulate insect growth. Bioassays including cell culture and/or transgenic insects engineered with various components of the ecdysoid receptor (EcR) and/or the farsenoid-X receptor (RXR) systems to identify compounds that act as insecticides and/or hormone receptor activators are described. Also described are compounds, and compositions, identified as being putative insecticides based upon their ability to activate EcR and/or FXR mediated transcription.

21 Claims, 23 Drawing Sheets

OTHER PUBLICATIONS

Bruenger, E. et al., "Determination of Isopentenyl Diphosphate and Farnesyl Diphosphate in Tissue Samples with a Comment on Secondary Regulation of Polyisoprenoid Biosynthesis." Anal. Biochem., 1988, 173:321-327.

Buckingham, S. et al., "Imidacloprid Actions on Insect Neuronal Acetylcholine Receptors." J. Exp. Biol., 1997, 200:2685-2692.

Burke, Y. et al., "Inhibition of Pancreatic Cancer Growth by the Dietary Isoprenoids Farnesol and Geraniol." Lipids, 1997, vol. 32, No. 2, 151-156.

Carchman, R. et al., "The Inhibition of DNA Synthesis by Cannabinoids." Cancer Res., 1976, 36:95-100.

Carney, G. et al., "The *Drosophila ecdysone* Receptor (EcR) Gene is Required Maternally for Normal Oogenesis." Genetics, 2000, 154:1203-1211.

Carlisle, D. et al., "Insect Hormones: Olive Oil is not an Inert Vehicle for Hormone Injection into Locusts." Science, 1968, vol. 162, No. 3860, 1393-1394.

Carlson, G. et al., "The Chemical and Biological Properties of Methoxyfenozide, A New Insecticidal Ecdysteroid Agonist." Pest Manag. Sci., 2001, 57:115-119.

Case, G. et al., "Induction of Geranyl Pyrophosphate Pyrophosphatase Activity by Cholesterol-Suppressive Isoprenoids." Lipids, 1995, vol. 30, No. 4, 357-359.

Chance, B. et al., "Inhibition of Electron and Energy Transfer in Mitochondria. Effects of Amytal, Thiopental, Rotenone, Progesterone, and Methylene Glycol." J. Biol. Chem., 1963, vol. 278, No. 1, 418-431.

Chen, J. et al. "Molecular Cloning and Induction of Nuclear Receptors from Insect Cell Lines." Insect Biochem. Mol. Biol., 2002, 32:657-667.

Cherbas, L. et al., "Effects of Juvenile Hormone on the Ecdysone Response in *Drosophila* KC Cells." Dev. Genet., 1989, 10:177-188.

Cherbas, L. et al., "EcR Isoforms in *Drosophila*: Testing Tissue-Specific Requirements by Targeted Blockade and Rescue." Development, 2003, 130:271-284.

Chiang, J. et al., "Farnesoid X Receptor Responds to Bile Acids and Represses Cholesterol 7 α-Hydroxylase Gene (CYP7A1) Transcription." J. Biol. Chem., 2000, vol. 275, No. 15, 10918-10924.

Chihara, C. et al., "Effects and Interactions of Juvenile Hormone and β-Ecdysone on *Drosophila* Imaginal Discs Cultured in Vitro." Dev. Biol., 1973, 35:36-46.

Christophe, J. et al., "Studies on the Biosynthesis of Cholesterol. XIV. The Origin of Prenoic Acids from Allyl Pyrophosphates in Liver Enzyme Systems." J. Lipid Res., 1961, vol. 2, No. 3, 244-257.

Christopherson, K. et al., "Ecdysteroid-Dependent Regulation of Genes in Mammalian Cells by a *Drosophila ecdysone* Receptor and Chimeric Transactivators." Proc. Natl. Acad. Sci. USA, 1992, 89:6314-6318.

Dai, J. et al., "Metamorphosis of the *Corpus allatum* and Degeneration of the Prothoracic Glands during the Larval-Pupal-Adult Transformation of *Drosophila melanogaster*: A Cytophysiological Analysis of the Ring Gland." Dev. Biol., 1991, 144:309-326.

Daves, G. et al., "Discovery of Ubiquinones-1, -2, -3, and -4 and the Nature of Biosynthetic Isoprenylation." Biochemistry, 1967, vol. 6, No. 9, 2861-2866.

Dubrovsky, E. et al. "Juvenile Hormone Signaling During Oogenesis in *Drosophila melanogaster*." Insect Biochem. Mol. Biol., 2002, 32:1555-1565.

Elegbede, J. et al., "Inhibition of DMBA-Induced Mammary Cancer by the Monoterpene D-Limonene." Carcinogenesis, 1984, vol. 5, No. 5, 661-664.

Elekonich, M. et al., "Juvenile Hormone Levels in Honey Bee (*Apis mellifera* L.) Foragers: Foraging Experience and Diurnal Variation." J. Insect Physiol., 2001, 47:1119-1125.

Farkas, R. et al., "Ecdysone-Modulated Response of *Drosophila cytosolic* Malate Dehydrogenase to Juvenile Hormone." Arch. Insect Biochem. Physiol., 1997, 35:71-83.

Forman, B. et al., "Identification of a Nuclear Receptor that is Activated by Farnesol Metabolites." Cell, 1995, 81:687-695.

Fukami, J. et al., "Metabolism of Rotenone In Vitro by Tissue Homogenates from Mammals and Insects." Science, 1967, vol. 155, No. 3763, 713-716.

Goldstein, J. et al., "Regulation of the Mevalonate Pathway." Nature, 1990, 343:425-430.

Henrick, C. et al., "Alkyl 3,7,11-Trimethyl-2,4-Dodecadienoates, A New Class of Potent Insect Growth Regulators with Juvenile Hormone Activity." J. Agr. Food Chem., 1973, vol. 21, No. 3, 354-359.

Hiruma, K. et al., "Juvenile Hormone Modulates 20-Hydroxyecdysone-Inducible Ecdysone Receptor and Ultraspiracle Gene Expression in the Tobacco Hornworm, Manduca Sexta." Dev. Genes Evol., 1999, 209:18-30.

Hosie, A. et al., "Actions of the Insecticide Fipronil, on Dieldrin-Sensitive and- Resistant GABA Receptors of *Drosophila melanogaster*." Br. J. Pharmacol., 1995, 115:909-912.

Howard, W. et al., "Catabolites of Cholesterol Synthesis Pathways and Forskolin as Activators of the Farnesoid X-Activated Nuclear Receptor." Tox. Appl. Pharm., 2000, 163:195-202.

Huang, M. et al., "Inhibition of Skin Tumorigenesis by Rosemary and its Constituents Carnosol and Ursolic Acid." Cancer Res., 1994, 54:701-708.

Jacobson, M. et al., "Naturally Occurring Insect Growth Regulators. III. Echinolone, a Highly Active Juvenile Hormone Mimic from *Echinacea angustifolia* Roots." Lloydia, 1975, vol. 38, No. 6, 473-476.

Jarvis, D. et al., "Construction and Characterization of Immediate Early *Baculovirus pesticides*." Biol. Control, 1996, 7:228-235.

Johnson, J. et al., "Two-Year Toxicity and Carcinogencity Study of Methyleugenol in F344/N Rats and B6C3F$_1$ Mice." J. Agric. Food Chem., 2000, 48:3620-3632.

Jones, G. et al., "Ultraspiracle: An Invertebrate Nuclear Receptor for Juvenile Hormones." Proc. Natl. Acad. Sci. USA, 1997, vol. 94, No. 25, 13499-13503.

Jones, G. et al., "Juvenile Hormone III-Dependent Conformational Changes of the Nuclear Receptor Ultraspiracle." Insect Biochem. Mol. Biol., 2001, 32:33-49.

Katiyar, S. et al., "Protective Effects of Silymarin against Photocarcinogenesis in a Mouse Skin Model." J. Natl. Cancer Inst., 1997, vol. 89, No. 8, 556-566.

Kitareewan, S. et al., "Phytol Metabolites are Circulating Dietary Factors that Activate the Nuclear Receptor RXR." Mol. Biol. Cell, 1996, 7:1153-1166.

Koelle, M. et al., "The *Drosophila* EcR Gene Encodes an Ecdysone Receptor, A New Member of the Steroid Receptor Superfamily." Cell, 1991, 67:59-77.

Kumar, R. et al., "The Structure of the Nuclear Hormone Receptors." Steroids, 1999, 64:310-9.

Kunkel, et al., "Rapid and Efficient Site-Specific Mutagenesis without Phenotypic Selection." Proc. Natl. Acad. Sci. USA, 1985, vol. 82, No. 2, 488-492.

Law, J. et al., "Synthesis of a Material with High Juvenile Hormone Activity." Proc. Natl. Acad. Sci. USA, 1966, vol. 55, No. 3, 576-578.

Lefebvre, P. et al., "Two Regions of the Mouse Mammary Tumor Virus Long Terminal Repeat Regulate the Activity of its Promoter in Mammary Cell Lines." Mol. Cell Biol., 1991, vol. 11, No. 5, 2529-2537.

Lezzi, M. et al., "The Ecdysone Receptor Puzzle." Archives of Insect Biochem. and Physiol., 1999, 41:99-106.

Louvion, J. et al., "Fusion of GAL4-VP16 to a Steroid-Binding Domain Provides a Tool for Gratuitous Induction of Galactose-Responsive Genes in Yeast." Gene, 1993, 131:129-134.

Mangelsdorf et al., "The Nuclear Receptor Superfamily: The Second Decade." Cell, 1995, 83:835-839.

McNamee, D., "Limonene Trial in Cancer." Lancet, 1993, 342:801.

Meyers, M. et al., "Estrogen Receptor Subtype-Selective Ligands: Asymmetric Synthesis and Biological Evaluation of Cis- and Trans-5,11-Dialkyl- 5,6,11, 12-Tetrahydrochrysenes." J. Med. Chem., 1999, 42:2456-2468.

Miesfeld et al., "Genetic Complementation of a Glucocorticoid Receptor Deficiency by Expression of Cloned Receptor cDNA." Cell, 1986, 46:389-399.

Miller, E. et al., "Structure-Activity Studies of the Carcinogenicities in the Mouse and Rat of Some Naturally Occurring and Synthetic Alkenylbenzene Derivatives Related to Safrole and Estragole." Cancer Res., 1983, 43:1124-1134.

Minakuchi, M. et al., "Molecular Cloning and Expression Analysis of Ultraspiracle (USP) from the Rice Stem Borer Chilo Suppressalis." Insect Biochem. Mol. Biol., 2003, 33:41-49.

Mouillet, J. et al., "Differential Control of Gene Activity by Isoforms A, B1, and B2 of the *Drosophila ecdysone* Receptor." Eur. J. Biochem., 2001, 268:1811-1819.

Munson, A. et al., "Antineoplastic Activity of Cannabinoids." JNCI, 1975, vol. 55, No. 3, 597-602.

Nathanson, J., "Caffeine and Related Methylxanthines: Possible Naturally Occurring Pesticides." Science, 1984, vol. 226, No. 4671, 184-187.

Nishino, H. et al., "Inhibition of the Tumor-Promoting Action of 12-O-Tetradecanoylphorbol-13-Acetate by some Oleanane-Type Triterpenoid Compounds." Cancer Res., 1988, 48:5210-5215.

No, D. et al., "Ecdysone-Inducible Gene Expression in Mammalian Cells and Transgenic Mice." Proc. Natl. Acad. Sci. USA, 1996, 93:3346-3351.

Oberdorster, E. et al., "Interaction of PAHs and PCBs with Ecdysone-Dependent Gene Expression and Cell Proliferation." Tox. Appl. Pharm., 1999, 160:101-108.

Oro, A. et al., "Relationship between the Product of the *Drosophila* Ultraspiracle Locus and the Vertebrate Retinoid X Receptor." Nature, 1990, 347:298-301.

Palli, S. et al., "Improved Ecdysone Receptor Based Inducible Gene Regulation System." Eur. J. Biochem., 2003, 270:1308-1315.

Pearson et al., "Improved Tools for Biological Sequence Comparison." Proc. Natl. Acad. Sci. USA, 1988, vol. 85, No. 8, 2444-2448.

Pratt, G. et al., "Lethal Metabolism of Precocene-I to a Reactive Epoxide by Locust Corpora Allata." Nature, 1980, 284:320-323.

Ratnayake, W. et al., "Investigation of the Effect of Coffee Lipids on Serum Cholesterol in Hamsters." Food Chem. Toxicol., 1995, vol. 33, No. 3, 195-201.

Richards, G. "Sequential Gene Activation by Ecdysone in Polytene Chromosomes of *Drosophila melanogaster*." Dev. Biol., 1978, 66:32-42.

Riddiford, L. "Cellular and Molecular Actions of Juvenile Hormone I. General Considerations and Premetamorphic Actions." Adv. Insect Physiol., 1994, 24:213-274.

Riddiford, L. et al., "Regulation and Role of Nuclear Receptors during Larval Molting and Metamorphosis of Lepidoptera." Amer. Zoologist, 1999, vol. 39, No. 4, 736-746.

Riddiford, L., "Hormone Receptors and the Regulation of Insect Metamorphosis." Receptor, 1993, 3:203-209.

Riddiford, L., "Juvenile Hormone: The Status of its "Status Quo" Action." Arch. Insect Biochem. Physiol., 1996, 32:271-286.

Riddihough, G. et al., "An Ecdysone Response Element in the *Drosophila* hsp27 Promoter." EMBO J., 1987, vol. 6, No. 12, 3729-3734.

Sacklin, J. et al., "Effect of DDT on Enzymatic Oxidation and Phosphorylation." Science, 1955, vol. 122, No. 3165, 377-378.

Sasorith, S. et al., "Structure-Based Analysis of the Ultraspiracle Protein and Docking Studies of Putative Ligands." J. of Insect Sci., 2002, 2:1-11.

Schneiderman, H. et al., "Control of Growth and Development in Insects." Science, 1964, vol. 143, No. 3604, 325-333.

Sheng, L. et al.(Abstract) "Developmental Changes in the Ability to Synthesize Juvenile Hormone In Vitro by Corpora Allata from the Eri Silkworm, Samia Cynthia Ricini (Lepidoptera: Satumiidae) (citation)." Euro. J. Entomol., 2002, vol. 99, No. 4, 413-419.

Shonouda, M. et al., "Efficacy of the Botanical Extract (MYRRA), Chemical Insecticides and their Combinations on the Cotton Leafworm, Spodoptera Littoralis Boisd (Lepidoptera : Noctuidae)." J. Environ. Sci. Health, 2000, B35, vol. 3, 347-356.

Smagghe, G. et al., "Comparative Toxicity and Ecdysone Receptor Affinity of Non-Steroidal Ecdysone Agonists and 20-Hydroxyecdysone in Chironomus Tentans." Insect Biochem. Mol. Biol., 2002, 32:187-192.

Smith, T. et al., "Comparison of Biosequences." Adv. Appl. Math, 1981, 2:482.

Soderlund, D. et al., "Precocene II Metabolism in Insects: Synthesis of Potential Metabolites and Identification of Initial In Vitro Biotransformation Products." J. Agric. Food Chem., 1980, 28:724-731.

Thummel, C., "Ecdysone-Regulated Puff Genes-2000." Insect Biochem. Mol. Biol., 2002, 32, 113-120.

Unger, E. et al, "A Chimeric Ecdysone Receptor Facilitates Methoxyfenozide-Dependant Restoration of Male Fertility in Ms45 Maize." Transgenic Res., 2002, 11:455-465.

Urizar, N. et al., "A Natural Product that Lowers Cholesterol as an Antagonist Ligand for FXR." Science, 2002, 296:1703-1706.

Vogtli, M. et al., "High Levels Transactivation by the Ecdysone Receptor Complex at the Core Recognition Motif." Nuc. Acids Res., 1998, vol. 26, No. 10, 2407-2414.

Wachs, H. "Synergistic Insecticides." Science, 1947, vol. 105, No. 2733, 530-531.

Weinberger, C. "A Model for Farnesoid Feedback Control in the Mevalonate Pathway." TEM, 1996, vol. 7, No. 1, 1-6.

Weusten-Van Der Wouw, M. et al., "Identity of the Cholesterol-Raising Factor from Boiled Coffee and its Effects on Liver Function Enzymes." J. Lipid Res., 1994, 35:721-735.

Wigglesworth, V., "The Juvenile Hormone." Nature, 1965, 208:522-524.

Wiseman, R. et al., "Structure-Activity Studies of the Hepatocarcinogenicities of Alkenylbenzene Derivatives Related to Estragole and Safrole on Administration to Preweanling Male C57BL/6J + C3H/HeJ F1 Mice." Cancer Res., 1987, 47:2275-2283.

Wolfgang, W., "Larval Cuticular Morphogenesis in the Tobacco Hornworm, Manduca Sexta, and its Hormonal Regulation." Dev. Biol., 1986, 113:305-316.

Wu, J. et al., "The Hypolipidemic Natural Product Guggulsterone Acts as an Antagonist of the Bile Acid Receptor." Mol. Endocrinol., 2002, vol. 16, No. 7, 1590-1597.

Wyatt, G. et al., "Cellular and Molecular Actions of Juvenile Hormone. II. Roles of Juvenile Hormone in Adult Insects." Adv. Insect Physiol., 1996, 26, 1-155.

Xu, Y. et al., "Activation of Transcription Through the Ligand-Binding Pocket of the Orphan Nuclear Receptor Ultraspiracle." Eur. J. Biochem., 2002, 269:6026-6036.

Yao, T. et al., "*Drosophila* Ultraspiracle Modulates Ecdysone Receptor Function Via Heterodimer Formation." Cell, 1992, 71:63-72.

Yao, T. et al., "Functional Ecdysone Receptor is the Product of EcR and Ultraspiracle Genes." Nature, 1993, 366: 476-479.

Zhou, X. et al., "Broad Specifies Pupal Development and Mediates the 'Status Quo' Action of Juvenile Hormone on the Pupal-Adult Transformation in *Drosophila* and *Manduca*." Development, 2002, 1290: 2259-2269.

Zi, X. et al., "Silibinin Decreases Prostate-Specific Antigen with Cell Growth Inhibition Via $G_1$ Arrest, Leading to Differentiation of Prostate Carcinoma Cells: Implications for Prostate Cancer Intervention." Proc. Natl. Acad. Sci. USA, 1999, vol. 96, No. 13, 7490-7495.

NCBI Sequence, Accession No. S63761, "EcR=EcR-A {EcR-A specific region, alternatively spliced} [*Drosophila melanogaster*, Genomic/mRNA, 1070 nt]." Cell 1993, 73:1323-1337.

NCBI Sequence, Accession No. S63762, "EcR=Ecdysone Receptor {5' region, EcR-B specific region} [*Drosophila melanogaster*, Genomic, 282 nt]." Cell 1993, 73:1323-1337.

NCBI Sequence, Accession No. AF045891, "Chironomus Tentans Ultraspiracle (USP-1) mRNA, Complete Cds." Insect Biochem. Mol. Biol., 1999, 29:931-942.

NCBI Sequence, Accession No. M74078, "*Drosophila melanogaster* Ecdysone Receptor (EcR) mRNA, Complete Cds." Cell, 1991, 67:59-77.

NCBI Sequence, Accession No. RNU18374, "Rattus Norvegicus Farnesoid X Activated Receptor mRNA, Complete Cds." Cell, 1995, 81:687-693.

Arbeitman, et al., "Molecular Chaperones Activate the *Drosophila* Ecdysone Receptor, an RXR Heterodimer." Cell, vol. 101, No. 1,pp. 67-77, 2000.

Dela-Cruz, et al., "*Drosophila* Ecdysone Receptor Functions as a Constitutive Activator in Yeast." J. Steroid Biochem. Molec. Biol., vol. 62, No. 4, pp. 353-359, 1997.

Dinan, et al., "Cucurbitacins are Insect Steroid Hormone Antagonists acting at the Ecdysteroid Receptor." Biochemical J., vol. 327, No. 3, pp. 643-650, 1997.

Henrich, et al., "Juvenile Hormone Potentiates Ecdysone Receptor-Dependent Transcription in a Mammalian Cell Culture System." Insect Biochemistry and Molecular Biology, vol. 33, No. 12, pp. 1239-1247, 2003.

Martinez, et al., "Transcriptional Activation of the Cloned *Heliothis virescens* (Lepidoptera) Ecdysone Receptor (HvEcR) by Muristerone A." Insect Biochemistry and Molecular Biology. vol. 29. No. 10, pp. 915-930, 1999.

Saez, et al., "Identification of Ligands and Coligands for the Ecdysone-Regulated Gene Switch." Proceedings of the National Academy of Sciences of the United States of America, vol. 97, No. 26, pp. 14512-14517. 2000.

Zhang, at al., "Natural Structural Variants of the Nuclear Receptor Fernesoid X Receptor affect Transcriptional Activation." Journal Of Biological Chemistry, vol. 278. No. 1, pp. 104-110, 2003.

Patent Cooperation Treaty, International Search Report, International Application No. PCT/US2004/028113, mailed on Mar. 7, 2005, 8 pages.

Feyereisen, R., "Juvenile Hormone Resistance: no. PASaran," Proc. Natl. Acad. Sci., vol. 95, pp. 2725-2726, 1998.

Wurtz, J. et al., A Canonical Structure for the Ligand-Binding Domain of Nuclear Receptors, Nature Structural Biology, vol. 3, No. 1, pp. 87-94, 1996.

Wurtz, J. et al., A Canonical Structure for the Ligand-Binding Domain of Nuclear Receptors, Nature Structural Biology, vol. 3, No. 2, pp. 206, 1996.

Billas, I. et al., Structural Adaptability in the Ligand-Binding Pocket of the Ecdysone Hormone Receptor, Nature, vol. 426, pp. 91-96, 2003.

Tobe, S. et al., Juvenile Hormone Titre and Regulation in the Cockroach *Diploperapunctata*, Experientia, vol. 41, pp. 1028-1034, 1985.

Roller, H. et al., The Chemistry and Biology of Juvenile Hormone, Recent Prog. Horm. Res., vol. 24, pp. 651-680, 1968.

NCBI Accession No. U18374, Identification of a Nuclear Receptor that is Activated by Farnesol Metabolites, Cell, vol. 81, No. 5, pp. 687-693, 1995.

Schooley, D. et al., Juvenile hormone biosynthesis. In: *Comprehensive Insect Physiology, Biochemistry, and Pharmacology* Edited by GA Kerkut, LI Gilbert, vol. 7. pp. 363-389. Oxford: Pergamon Press; 1985: 363-389.

Crowell, P. et al., Chemoprevention and Therapy of Cancer by d-Limonene, Critical Reviews in Oncogenesis, vol. 5, No. 1, pp. 1-22, 1994.

Machicao, F. et al., Mechanism of the Stimulation of RNA Synthesis in Rat Liver Nuclei by Silybin, Hoppe-Seyler's Z Physiol. Chem., vol. 358, pp. 141-147, 1977.

Krecman, V. et al., Silymarin Inhibits the Development of Diet-Induced Hypercholersterolemia in Rats, Planta Med., vol. 64, pp. 138-142, 1998.

Bowers, W., Toxicology of the Precocenes. In: *Insecticide Mode of Action* Edited by JR Coats. New York: Academic Press; 1982.

Isoform and Interspecies Comparision of Ecdysteroid Receptor in a Cell Culture System, XVI International Ecdysone Workshop, Jul. 13, 2006, Ghent, Belgium.

The *Drosophilia ecdysteroid* Receptor: Not a Trigger for Developmental Processes, Endocrinology Workshop, Oct. 6, 2005, University of Ulm, Germany.

Olson, R., Biosynthesis of Ubiquinones in Animals, Vitam. Horm., vol. 24, pp. 551-574, 1966.

Li, T. et al., A Conditional Rescue System reveals Essential Functions for the Ecdysone Receptor (EcR) Gene during Molting and Metamorphosis in *Drosophila*, Development, vol. 127, pp. 2897-2905, 2000.

Hu, X. et al., Transcription Activation by the Ecdysone Receptor (EcR/USP): identification of Activation Functions, Molecular Endocrinology, vol. 17, No. 4, pp. 716-731, 2003.

Gilbert, L. et al., The Juvenile Hormones: Historical Facts and Speculations on Future Research Directions, Insect Biochemistry and Molecular Biology, vol. 30, pp. 617-644, 2000.

Hall, B. et al., The RXR Homolog Ultraspiracle is an Essential Component of the *Drosophila* Ecdysone Receptor, Development, vol. 125, pp. 4709-4717, 1998.

Riddiford, L. et al., Ecdysone Receptors and Their Biological Actions, Vitamins and Hormones, vol. 60, pp. 1-73, 2000.

Sung, C. et al., Characterization of the Regulatory Elements Controlling Neuronal Expression of the A-Isoform of the Ecdysone Recepor Gene of *Drosophila melanogaster*, Mechanisms of Development, vol. 91, pp. 237-248, 2000.

Schubiger, M. et al., *Drosophila* EcR-B Ecdysone Receptor Isoforms are Required for Larval Molting and for Neuron Remodeling during Metamorphosis, Development, vol. 125, pp. 2053-2062, 1998.

Antoniewski, C. et al., Structural Features Critical to the Activity of an Ecdysone Receptor Binding Site, Insect Biochem. Mol. Biol., vol. 23, pp. 105-114, 1993.

Bowers, W. et al., Discovery of Insect Anti-Juvenile Hormones in Plants, Science, vol. 193, pp. 542-547, 1976.

Li, S. et al., Developmental Changes in the Ability to Synthesize Juvenile Hormone In-Vitro by Corpora Allata from the Eri Silkworm, Samia Cynthia Ricini (Lepidoptera: Saturnidea) (citation), Euro. J. Entomol., 2002, vol. 99, No. 4, 413-419.

Meyer, A. et al., A Highly Purified Preparation of Juvenile Hormone from the Silk Moth Hyalophora Cecropia L., nature, vol. 206, pp. 272-275, 1965.

Wurtz, J. et al., Structure-Based Analysis of the Ultraspiracle Protein and Docking Studies of Putatiive :Ligands, J. of Insect. Sci., vol. 2, pp. 1-11, 2002.

United States Patent and Trademark Office, Office Action, U.S. Appl. No. 11/543,682, mailed Jan. 26, 2009.

Carney, G. et al., Creation of EcR Isoform-Specific Mutations in *Drosophila melanogaster* via local P Element Transposition, Imprecise P Element Excision, and Male Recombination, Mol. Genet. Genomics, vol. 271, pp. 282-290, 2004.

Przibilla, S. et al., Functional Studies on the Ligand-Binding Domain of Ultraspiracle from *Drosophila melanogaster*, Biol. Chem., vol. 358, pp. 21-30, 2004.

Schubiger, M. et al., Isoform Specific Control of Gene Activity In-Vivo by the *Drosophila* Ecdysone Receptor, Mech. Dev., vol. 120, pp. 909-918, 2003.

Clayton, G. et al., The Structure of the Ultraspiracle Ligand-Binding Domain Reveals a Nuclear Receptor locked in an Inactive Conformation, Proc. Natl., Acad. Sci. USA, vol. 98, pp. 1549-1554, 2001.

Oro, A. et al., The *Drosophila* Retinoid X Receptor Homolog Ultraspiracle Functions in Both Female Reproduction and Eye Morphogenesis, Development, vol. 115, pp. 449-462, 1992.

Perrimon, N. et al., Developmental Genetics of the 2C-D Region of the *Drosophila* X Chromosome, Genetics, vol. 111, pp. 23-41, 1985.

Truman, J. et al., Ecdysone Receptor Expression in the CNS Correlates with Stage-Specific Responses to Ecydsteroids during *Drosophila* and Manduca Development, Development, vol. 120, pp. 219-234, 1994.

Giguere, V. et al., "Identification of a Receptor for the Morphogen Retinoic Acid." Nature, 1987, 330:624-629.

Grober, et al., "Identification of a Bile Acid-responsive Element in the Human Ileal Bile Acid-Binding Protein Gene: Involvement of the Farnesoid X Receptor/9-cis-Retinoic Acid Receptor Heterodimer." J. Biol. Chem., 1999, vol. 274, No. 42, 29749-29754.

Guzelian, P. et al., "Drug Metabolism in Adult Rat Hepatocytes in Primary Monolayer Culture." Gastroenterology, 1977, 72:1232-1239.

Hall, B. et al., "Nuclear Receptors and the Hormonal Regulation of *Drosophila metamorphosis*." Amer. Zoologist, 1999, 39:714-721.

Haller, H. et al., "The Synergisict Action of Sesamin with Pyrethrum Insecticides." J. Org. Chem., 1942, 7:183-184.

Hanley, K. et al., "Activators of the Nuclear Hormone Receptors PPARα and FXR Accelerate the Development of the Fetal Epidermal Permeability Barrier." J. Clin. Invest., 1997, vol. 100, No. 3, 705-712.

Harmon, M. et al., "Activation of Mammalian Retonid X Receptors by the Insect Growth Regulator Methoprene." Proc. Natl. Acad. Sci. USA, 1995, vol. 92, No. 13, 6157-6160.

He, L. et al., "Isoprenoids Suppress the Growth of Murine B16 Melanomas In Vitro and in Vivo." J. Nutr., 1997, 127:668-674.

Henrich, V. et al., "A Steroid/Thyroid Hormone Receptor Superfamily Member in *Drosophila melanogaster* that Shares Extensive Sequence Similarity with a Mammalian Homologue." Nucl. Acids Res., vol. 18, No. 14, 4143-4148, 1990.

Henrich, V. et al., "Expression and Function of the Ultraspiracle (usp) Gene during Development of *Drosophila melanogaster*." Dev. Biol., 1994, 165:38-52.

Henrich, V. et al. "Effect of FXR Activators on Ecdysteroid Receptor Activity (abstract)" Proceedings of the International Ecdysone Workshop 2000, Rapperswil, Switzerland.

Henrich, V. "Strategies for Identifying Molecular Targets to Insect Ecdysteroid Receptors (Abstract)." Agric, University of North Carolina, Biology (Award Type-NRI Competitive Grant .C C), printed Aug. 12, 2003.

Soderlund, D., "Pyrethroid-Receptor Interactions: Stereospecific Binding and Effects on Sodium Channels in Mouse Brain Preparations." Neurotoxicology, 1985, vol. 6, No. 2, 35-46.

Soderlund, D. et al., "Mechanisms of Pyrethroid Neurotoxicity: Implications for Cumulative Risk Assessment." Toxicology, 2002, 171:3-59.

Sugano, S. et al., "Identification of Intermediates in the Conversion of Cholesterol to Pregnenolone with a Reconstituted Cytochrome P-450$_{SCC}$ System: Accumulation of the Intermediate Modulated by the Adrenodoxin Level." J. Biochem., 1996, 120:780-787.

Suhr, S. et al., "High Level Transactivation by a Modified Bombyx Ecdysone Receptor in Mammalian Cells without Exogenous Retinoid X Receptor." Proc. Natl. Acad. Sci. USA, 1998, vol. 95, No. 14, 7999-8004.

Sun, X. et al., "Effect of Ecdysone Agonists on Vitellogenesis and the Expression of EcR and USP in Codling Moth (*Cydia pomonella*)." Arch. Insect Biochem. Physiol., 2003, 52:115-129.

Talbot, W. et al. "*Drosophila* Tissues with Different Metamorphic Responses to Ecdysone Express Different Ecdysone Receptor Isoforms." Cell, 73:1323-1337, 1993.

Terpstra, A. et al., "The Hypercholesterolemic Effect of Cafestol in Coffee Oil in Gerbils and Rats." J. Nutr. Biochem., 2000, 11:311-317.

Thelle, D. et al., "The Tromso Heart Study. Does Coffee Raise Serum Cholesterol?" N. Engl. J. Med., 1983, 308:1454-1457.

Theriault, A. et al., "Modulation of Hepatic Lipoprotein Synthesis and Secretion by Taxifolin, A Plant Flavonoid." J. Lipid Res., 2000, 41:1969-1979.

Thomas, H. et al., "Heterodimerization of the *Drosophila* Ecdysone Receptor with Retinoid X Receptor and Ultraspiracle." Nature,1993, 362: 471-475.

Robinow, S. et al., Programmed Cell Death in the *Drosophilia* CNS is Ecdysone-Regulated and Coupled with a Specific Ecdysone Receptor Isoform, Development, vol. 119, pp. 1251-1259, 1993.

Schubiger, M. et al., The RXR Ortholog USP Suppresses Early Metamorphic Processes in *Drosophila* in the Absence of Ecdysteroids, Development, vol. 127, pp. 1151-1159, 2000.

Ghbeish, N. et al., The Dual Role of Ultraspiracle, the *Drosophila* Retinoid X Receptor, in the Ecdysone Response, PNAS, vol. 98, No. 7, pp. 3867-3872, 2001.

Ghbeish, N. et al., Analyzing the Repressive Function of Untraspiracle, the *Drosophila* RXR, in *Drosophila* Eye Development, Mechanisms of Development, vol. 111, pp. 89-98, 2002.

Needleman, S. et al., A General Method Applicable to the Search for Similarities in the Amino Acid Sequence of Two Proteins, J. Mol. Biol., vol. 48, pp. 443-453, 1970.

Wisconsin Genetics Software Package Release 7.0, Genetics Computer Group, 575 Science Drive, Madison, WI, 2002.

Bergman, T. et al., Ligand Control of Interaction In Vivo Between Ecdysteroid Receptor and Ultraspiracle Ligand-Binding Domain, Biochem. Society, vol. 378, pp. 779-784, 2004.

Grebe, M. et al., Characterization of the Ligand-Binding Domain of the Ecdysteroid Receptor from *Drosophila melanogaster*, Biol. Chcm., vol. 384, pp. 105-116, 2003.

Characterization of *Drosophila* EcR and USP in a Mammalian Cell Culture System, National *Drosophila* Research Conference in San Diego (Mar. 30-Apr. 3, 2005).

Beatty, J. et al., Analysis of Transcriptional Activity mediated by the *Drosophila melanogaster* Ecdysone Receptor Isoforms in a Heterologous Cell Culture System, Insect Mol. Biol., vol. 15, pp. 785-795, 2006.

U.S. Appl. No. 12/731,810, filed Mar. 25, 2010, Henrich, III.

* cited by examiner

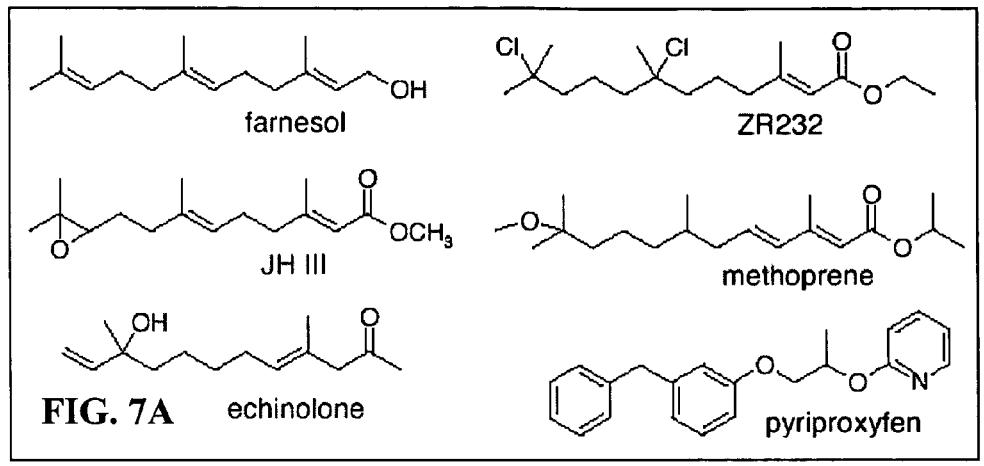
FIG. 7A
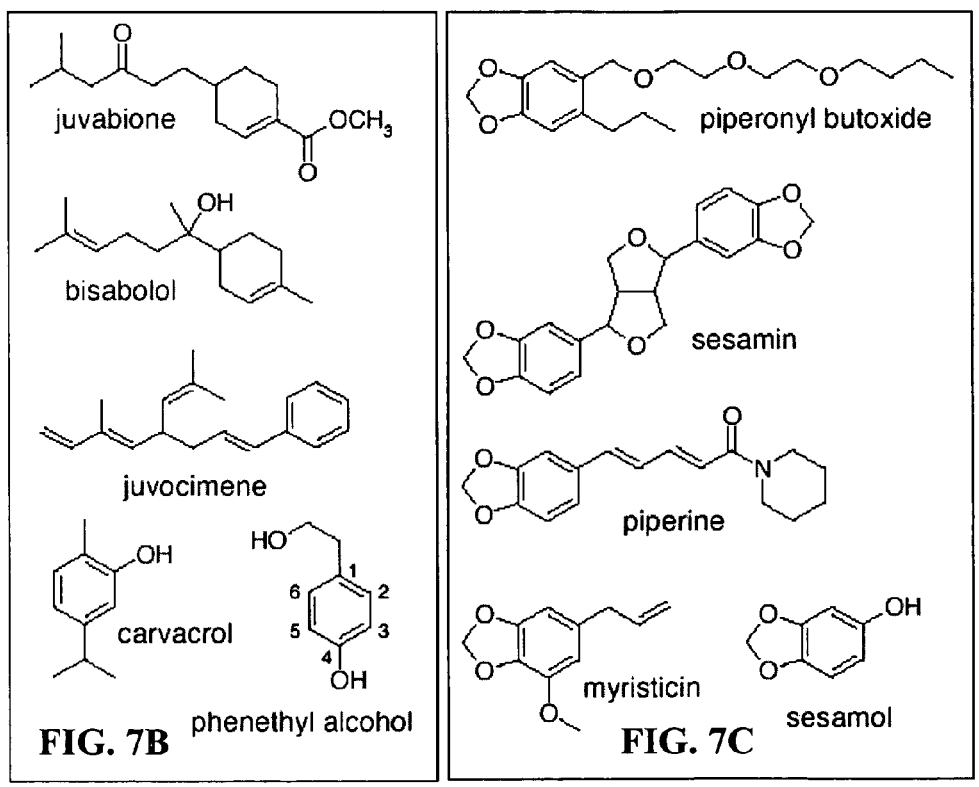
FIG. 7B     FIG. 7C

JH 0

JH I

JH II

JH III

ZR354 ously. Others such as pyrethrins and organophosphates are neurotoxic (Soderlund, D. M., et al., 2002, *Toxicology*, 171:3-59; Johnson, M. K.,. 1975, *Arch. Toxicol.*, 34:259-288).

SEQUENCE LISTING

<160> NUMBER OF SEQ ID NOS: 17

<210> SEQ ID NO 1
<211> LENGTH: 28
<212> TYPE: DNA
<213> ORGANISM: Artificial Sequence
<220> FEATURE:
<223> OTHER INFORMATION: Synthetic

```
<400> SEQUENCE: 1
ggaatgattg catcatcgat aaaattcg                                      28

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
gaggtctcga gtgagactcc tgta                                          24

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
ctcgagtgta tgtatacagg tttgttaact gaa                                33

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
aacaaacctg tatacataca ctcga                                         25

<210> SEQ ID NO 5
<211> LENGTH: 40
<212> TYPE: PRT
<213> ORGANISM: Artificial Sequence
<220> FEATURE:
<223> OTHER INFORMATION: Synthetic

<400> SEQUENCE: 5

Gly Met Asn Leu Glu Ala Arg Lys Thr Lys Lys Ile Lys Gly Ile
1               5                   10                  15

Gln Gln Ala Thr Thr Gly Val Ser Gln Glu Cys Met Tyr Thr Gly Leu
            20                  25                  30

Leu Thr Glu Ile Gln Cys Lys Ser
        35                  40

<210> SEQ ID NO 6
<211> LENGTH: 33
<212> TYPE: DNA
<213> ORGANISM: Artificial Sequence
<220> FEATURE:
<223> OTHER INFORMATION: Synthetic

<400> SEQUENCE: 6
cctgcgccac ggcggccgcc ggagctgtgc ctg                                33

<210> SEQ ID NO 7
<211> LENGTH: 29
<212> TYPE: DNA
<213> ORGANISM: Artificial Sequence
<220> FEATURE:
<223> OTHER INFORMATION: Synthetic
```

<400> SEQUENCE: 7
gtgggtatgc gcctcgagtg cgtcgtccc                                    29

<210> SEQ ID NO 8
<211> LENGTH: 29
<212> TYPE: DNA
<213> ORGANISM: Artificial Sequence
<220> FEATURE:
<223> OTHER INFORMATION: Synthetic

<400> SEQUENCE: 8
gatccgacaa gggttcaatg cacttgtca                                    29

<210> SEQ ID NO 9
<211> LENGTH: 35
<212> TYPE: DNA
<213> ORGANISM: Artificial Sequence
<220> FEATURE:
<223> OTHER INFORMATION: Synthetic

<400> SEQUENCE: 9
cacccggatc caccatgttg acgacgagtg gacaa                             35

<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
acctctctag actatgcagt cgtcgagtgg tc                                32

<210> SEQ ID NO 11
<211> LENGTH: 35
<212> TYPE: DNA
<213> ORGANISM: Artificial Sequence
<220> FEATURE:
<223> OTHER INFORMATION: Synthetic

<400> SEQUENCE: 11
cacccggatc caccatgaag cggcgctggt cgaac                             35

<210> SEQ ID NO 12
<211> LENGTH: 35
<212> TYPE: DNA
<213> ORGANISM: Artificial Sequence
<220> FEATURE:
<223> OTHER INFORMATION: Synthetic

<400> SEQUENCE: 12
cacccggatc caccatggat acttgtggat tagta                             35

<210> SEQ ID NO 13
<211> LENGTH: 35
<212> TYPE: DNA
<213> ORGANISM: Artificial Sequence
<220> FEATURE:
<223> OTHER INFORMATION: Synthetic

<400> SEQUENCE: 13
cacccggatc caccatgaag aagggacctg cgcca                             35

<210> SEQ ID NO 14
<211> LENGTH: 31

-continued

```
<212> TYPE: DNA
<213> ORGANISM: Artificial Sequence
<220> FEATURE:
<223> OTHER INFORMATION: Synthetic

<400> SEQUENCE: 14
ttttgaattc agcggcagca agcacctctg c                                     31

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
ttttaagctt tagagtcggg accctactcc                                       30

<210> SEQ ID NO 16
<211> LENGTH: 31
<212> TYPE: DNA
<213> ORGANISM: Artificial Sequence
<220> FEATURE:
<223> OTHER INFORMATION: Synthetic

<400> SEQUENCE: 16
ttttgaattc tgctctattt gcggggatcg g                                     31

<210> SEQ ID NO 17
<211> LENGTH: 31
<212> TYPE: DNA
<213> ORGANISM: Artificial Sequence
<220> FEATURE:
<223> OTHER INFORMATION: Synthetic

<400> SEQUENCE: 17
ttttgaattc aagcgcgaag cggtccagga g                                     31
```

COMPOUNDS THAT ACT TO MODULATE INSECT GROWTH AND METHODS AND SYSTEMS FOR IDENTIFYING SUCH COMPOUNDS

STATEMENT OF RELATED APPLICATIONS

The present application claims priority under 35 USC 119 from the following U.S. Provisional Patent Application: Serial No. 60/498,847, filed Aug. 29, 2003, entitled "Methods and Systems for Identification of Insecticides and Hormone Receptor Activators"; the entirety of which is herein incorporated by reference.

FEDERAL SUPPORT

The work described herein was supported at least in part by Federal grants from the U.S. Department of Agriculture Competitive Grants program (00-35302-9327 and 03-35302-13474) and the National Institute of Environmental Health Sciences. Thus, the Federal government may have rights in this invention.

FIELD OF THE INVENTION

The present invention relates to compounds that act to modulate insect growth and methods and systems for identifying such compounds.

BACKGROUND

A vast collection of man-made and plant-derived chemicals that function as insecticides has been amassed over the past sixty years. Concerns over the use of these insecticides, the development of insect resistance, and the possible risk of long-term use for human health have fueled efforts to understand the mechanism by which such compounds act. Some, like the organo-chlorine DTT, inhibit ATP production (Sacklin, J. A. et al., 1955, *Science*, 122:377-378). Others such as pyrethrins and organophosphates are neurotoxic (Soderlund, D. M., et al., 2002, *Toxicology*, 171:3-59; Johnson, M. K.,. 1975, *Arch. Toxicol.*, 34:259-288).

Insect development appears to be driven by the action of at least two hormone classes, the ecdysteroids and the juvenile hormones (JHs, juvenoids) (Riddiford, L. M., 1994, *Adv. Insect Physiol.*, 24:213-274; Gilbert, L. I., et al., 2000, *Insect Biochem. Mol. Biol.*, 30:617-644; Thummel, C. S., 2002, *Insect Biochem. Mol. Biol.*, 32:113-120). It appears that ecdysteroids are responsible for initiating metamorphosis, and in some insects, regulating adult fertility. In contrast, JH appears to be required for reproductive processes such as adult female vitellogenesis (Wyatt, G. R., and K. G. Davey, 1996, *Adv. Insect Physiol.*, 26:1-15). Also, the simultaneous presence of ecdysteroids and juvenile hormone (JH) leads to larval-larval molting.

There are two heterodimeric partners that comprise the functional insect ecdysteroid receptor complex: the ecdysone receptor (EcR) (Koelle et al, 1991, *Cell*, 67:59-77) and Ultraspiracle (USP) (Oro, A. E., et al., 1990, *Nature*, 347:298-301; Henrich, V. C., et al., 1994, *Dev. Biol.*, 165:38-52). Both EcR and USP belong to the nuclear receptor superfamily, which includes receptors for steroid and thryroid hormones, retinoic acid, and fatty acids (Mangelsdorf et al., 1995, *Cell*, 83:835-839). Also, recently, a second receptor, DHR38, as a heterodimeric partner of USP has been shown to mediate ecdysteroid responses, but the mode of action is not classical, in that it does not involve direct binding of the ecdysteroid to either DHR38 or USP (Baker et al, 2003, *Cell* 113:731-742).

There may also be mammalian counterparts to the insect receptor for ectdysteroids. Thus, EcR structurally resembles the vertebrate farnesoid X-activated receptor (FXR) (Forman, B. M., et al., 1995, *Cell* 81:687-695). FXR is a member of the steroid receptor family that includes receptors for glucocorticoids, estrogen, vitamins A and D, thyroid hormones, and fatty acids. Also, there is evidence to suggest that USP may be the insect orthologue of the vertebrate retinoid X receptor (RXR) (Oro, A. E., et al., 1990, *Nature* 347:298-301). Comparisons of amino acids in the FXR and EcR DNA-binding domains reveal 60% identity, and the ligand binding domains (LBD) regions of these two receptors share about 45% identity. Nevertheless, the possible functional analogy between FXR/RXR and EcR/USP has yet to be resolved. For example, it has been shown that the vertebrate RXR is activated by methoprene acid but not JHIII or methoprene (Harmon, M. A., et al., 1995, *Proc. Natl. Acad. Sci. USA*, 92:6157-6160). In contrast, the insect USP complexes with JHIII and methoprene but not their acid metabolites (Jones, G. et al., 1997, *Proc. Natl. Acad. Sci. USA*, 94:13499-13503).

Due to concerns about possible toxicity of man-made insecticides, there is a need to identify natural compounds that have the ability to modulate insect survival and development. Understanding the basis by which compounds interact with the insect EcR and/or FXR to interfere with insect development may provide a rational basis for the isolation of safe, but effective insecticides.

SUMMARY OF THE INVENTION

Embodiments of the present invention provide compounds that act to modulate insect growth and methods and systems for identifying such compounds. The present invention may be embodied in a variety of ways.

In one embodiment, the present invention comprises a method for testing the ability of a compound to act as a modulator of insect growth comprising determining whether the compound increases FXR-mediated transcription and/or EcR-mediated transcription.

In one embodiment, the method comprises a cell based assay. For example, in one embodiment, the method may comprise transfecting a cell with DNA comprising a functional isoform of the ecdysone receptor (EcR) or the farnesoid X-activated receptor (FXR). In one embodiment, a cell that does not include EcR, FXR, or a binding partner for EcR or FXR is used for the assay so that there may be minimal background due to endogenous activation via EcR or FXR. The method may further comprise cotransfecting the cell with a DNA construct comprising a functional heterologous binding partner for either the EcR or FXR.

Increases in EcR-mediated transcription or FXR-mediated transcription may be measured in a variety of ways. In one example embodiment, DNA comprising a gene linked to a hormone response element (HRE) that recognizes an activated EcR complex or an activated FXR complex may be transfected into the cell. The gene linked to the HRE may be a reporter gene that is easily measured, as for example, the chloramphenicol acetyltransferace (CAT) gene. Once the individual components required for EcR-mediated transcription or FXR-mediated transcription are present in the cell, the compound to be tested for potential ability to increase FXR-mediated transcription or EcR-mediated transcription may be added, and activation of the gene that is linked to the HRE measured to quantify transcription mediated by either FXR or EcR. In one embodiment, the increase in reporter gene activity may be used to quantify the activity of the test compound as a potential insecticide, where the ability of a compound to act as an insecticide is positively correlated with activation of HRE mediated transcription of the reporter gene.

The present invention also comprises a method that may be used to screen for insecticides in the environment. Thus, in an embodiment, the present invention comprises a method for in situ testing for the presence of compound having the ability to modulate insect growth comprising transfecting a cell in an organism with DNA that encodes a functional isoform of the farnesoid X-activated receptor (FXR) and/or the ecdysone receptor (EcR). In one embodiment, the cell may also be transfected with a DNA encoding a functional RXR or USP isoform. Also, the cell may comprise a DNA comprising a hormone response element (HRE) linked to a reporter gene. In one example embodiment, the cell may be exposed to an ecdysteroid. The organism may then be exposed to the compound to be tested to determine the effect of the compound on FXR-activated transcription and/or EcR-activated transcription.

The present invention further comprises assay systems. In one embodiment, the present invention may comprise an assay system for the identification of compounds having the ability to act as a modulator of insect growth comprising a host cell transfected with an exogenous DNA construct comprising sequences encoding a functional isoform of the ecdysone receptor (EcR) or the farnesoid receptor (FXR); an exogenous DNA construct comprising sequences encoding a functional heterologous binding partner for EcR or FXR, wherein the heterologous binding partner forms a complex with either EcR or FXR, and wherein the complex binds to a hormone responsive element (HRE) on DNA to activate gene transcription; and DNA comprising a reporter construct comprising an EcR or FXR activated hormone response element (HRE) linked to a gene.

The present invention also comprises compounds that act as insecticides by their ability to inhibit insect growth, reproduction, and/or morphogenesis. Thus, in another embodiment, the present invention comprises a composition for use as an insecticide comprising a compound that increases FXR-mediated transcription and/or EcR-mediated transcription mixed with a suitable carrier for application to plants.

In yet another embodiment, the present invention may comprise a use for compounds identified using the methods and systems of the invention as insecticides and/or modulators of insect growth.

Certain embodiments of the present invention may comprise various advantages. For example, the present invention comprises methods and systems to identify natural compounds derived from plants that have the ability to increase FXR-mediated transcription and/or EcR-mediated transcription and thus, may be potential insecticides. Such natural compounds are potentially non-toxic insecticides; some of the compounds may even form part of the human diet.

The present invention may also provide for the discovery and/or refinement of ecdysteroid agonists and antagonists which exhibit a high potency for a targeted pest species, while exerting little impact on colocalized nonpest insects. A baseline of structural and mechanistic information about the insect ecdysteroid receptor and potential ligands already exists that may serve as a foundation for "rational design" approaches. The diversity of chemical structures associated with ecdysteroid agonist and antagonist activity indicates that there may be numerous potential agents having insecticidal or growth modifying activities that may be characterized using the systems and methods of the present invention. Because many of the compounds of the present invention are present in human dietary sources, they may be particularly useful for the control of insects that act as vectors or predators of animal and human populations. Thus, using the compounds, methods, and systems of the present invention, it may be possible to develop strategies for refining the effectiveness of existing insecticides as well as discovering new ones.

Additionally, as plants produce phytoecdysteroids and nonsteroidal agonists/antagonists, the possibility exists for genetic engineering to maximize and/or enhance the ability of plants to synthesize insecticides that impair insect receptor activity; the compounds produced by such engineered plants may be evaluated using the methods and systems of the present invention.

Also, ecdysteroids and their receptor may be implicated in adult insect reproductive development and physiological processes. Thus, the compounds of the present invention may be potentially useful for controlling adult stage as well as developing pests.

Additional features of the present invention will be described hereinafter. It is to be understood that the invention is not limited in its application to the details set forth in the foregoing or following description but is capable of other embodiments and of being practiced or carried out in various ways.

BRIEF DESCRIPTION OF THE FIGURES

FIG. 7 shows molecular structures of natural and synthetic juvenile hormone agonists with FXR effector activities in accordance with example embodiments of the present invention including: (7A) farnesol-like activators; (7B) juvenile hormone agonists from plants; and (7C) methylenedioxyphenyl-like chemicals with JH activity.

DETAILED DESCRIPTION

Figure 1A:
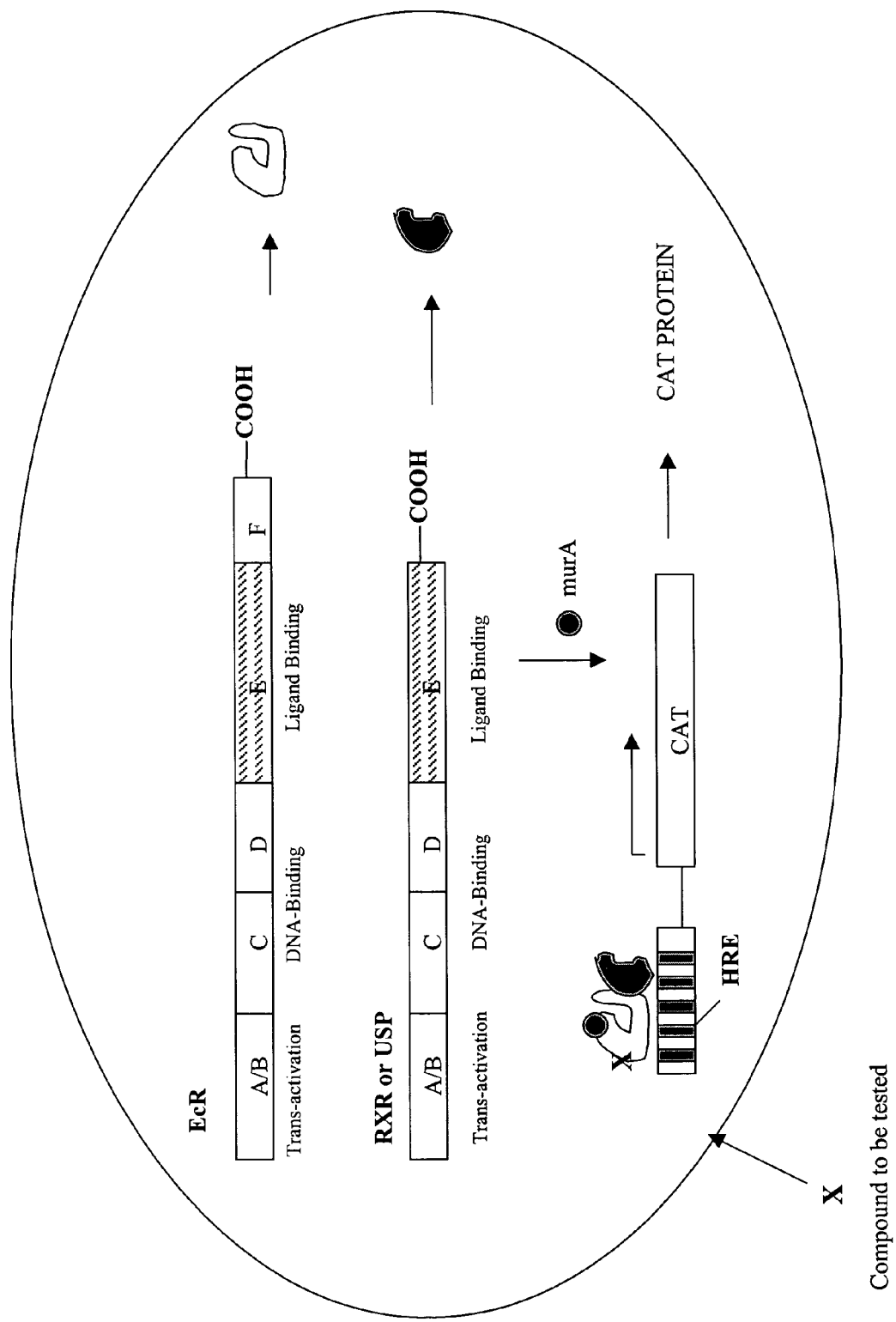
FIG. 1 shows a schematic diagrams of cell-based assay systems for detecting insecticides in accordance with example embodiments of the present invention where (1A) shown activation of EcR-mediated transcription potentiated by an ecdysteroid by compound X, and (1B) shows activation of FXR-mediated transcription by compound X.

Embodiments of the present invention provide compounds that function as insect growth modulators and/or insecticides. The present invention recognizes that there are nuclear receptor-gated signaling pathways in insects and mammals that may uniformly respond to a broad range of natural and synthetic insecticides. For example, the compounds of the present invention may target the ecdysone receptor (EcR) and/or the farnesoid X-activated receptor (FXR) to act as insect growth regulators and/or to interfere with insect development.

In additional embodiments, the present invention provides and methods and systems for the identification of compounds that act as insecticides or modulators of insect growth and/or development. Bioassays assembled using these receptors may be employed to guide the rational design of novel chemicals that specifically target insect pests.

Also described are compositions comprising compounds that function as insect growth regulators for the control of pests. The compounds used as growth regulators may be natural compounds, isolated from everyday plants such as sesame seeds, hops, coffee, and bergamot oil found in tea.

The present invention may be embodied in a variety of ways. In one embodiment, the present invention comprises a method for testing the ability of a compound to act as a modulator of insect growth comprising determining whether the compound increases farnesoid X-activated receptor (FXR)-mediated transcription and/or ecdysone receptor (EcR)-mediated transcription. In one embodiment, an increase in transcription comprises an increase from a measurable basal level to a higher level. Alternatively, an increase in transcription may comprise an increase from an undetectable level to a measurable level.

In one embodiment, an increase in EcR mediated transcription comprises potentiation of hormone activated EcR mediated transcription. The hormone may comprise an ecdysteroid. For example, in alternate embodiments, the hormone may comprise muristerone A (murA) or 20-hydroxyecdysone (20E).

The method may comprise a cell based assay. In one example embodiment, the method may comprise the steps of: (a) transfecting isolated cells with DNA comprising sequences that encode a functional isoform of the ecdysone receptor (EcR) or the farnesoid receptor (FXR); (b) cotransfecting the cell with: (i) DNA comprising sequences that encode a functional heterologous binding partner for (a), wherein said heterologous binding partner complexes with either EcR or FXR, and wherein the complex binds to a hormone responsive element (HRE) on DNA to activate gene transcription; and (ii) DNA comprising the reporter construct comprising a hormone response element (HRE) linked to a gene; (c) adding the compound to be tested; and (d) measuring an increase in the synthesis of the reporter gene protein. In one embodiment, an EcR modulator may be added to the cell such that potentiation of EcR activity may be measured.

The present invention further comprises assay systems. In one embodiment, the present invention may comprise an assay system for the identification of compounds having the ability to act as a modulator of insect growth comprising a host cell transfected with an exogenous DNA construct comprising sequences encoding a functional isoform of the ecdysone receptor (EcR) or the farnesoid receptor (FXR); an exogenous DNA construct comprising sequences encoding a functional heterologous binding partner for EcR or FXR, wherein the heterologous binding partner forms a complex with either EcR or FXR, and wherein the complex binds to a hormone responsive element (HRE) on DNA to activate gene transcription; and DNA comprising a reporter construct comprising an EcR or FXR activated hormone response element (HRE) linked to a gene.

In one embodiment, the increase in reporter gene activity may be used to quantify the ability of the test compound to increase EcR-mediated transcription or FXR-mediated transcription. In one example embodiment, the ability of the test compound to increase EcR-mediated transcription or FXR-mediated transcription may correlated to the potential insecticidal activity of the test compound.

In other embodiments of the present invention, transcription of a gene that is downstream of a hormone response element (HRE) that is activated by FXR and/or EcR may be measured directly. In an embodiment, a reporter gene comprising an HRE may be exogenous to the cell and added by transfection. Alternatively, transcriptional levels of an endogenous gene known to be activated by FXR or EcR may be measured. For example, in one embodiment, transcription may be measured by quantifying mRNA specific to a gene that comprises a promoter that includes an FXR HRE. Alternatively, transcription may be measured by quantifying enzyme activity specific to a protein encoded by a gene that comprises a promoter that includes an EcR HRE. Or, the actual amount of protein translated from a gene comprising a HRE may be measured by techniques known in the art such as sodium dodecyl sufate polyacrylamide gel electrophoresis (SDS-PAGE), or binding of an antibody specific for the translated gene product. Other methods to quantify gene transcription (e.g., quantitative PCR amplification of cDNA, RNA hybridization, and the like) may also be used.

The heterologous binding partner may vary depending upon the DNA-receptor (e.g., FXR or EcR) being used. In one embodiment, the heterologous binding partner may comprise Ultraspiracle (USP). Alternatively, the heterologous binding partner may comprise vertebrate retinoid X receptor (RXR).

The EcR modulator may be one of several compounds known to interact with EcR and its heterologous binding partner. In one embodiment, the EcR modulator may bind to the ligand binding domain (LBD) of EcR. Or, the EcR modulator may bind to other portions of the EcR polypeptide. For example, the EcR modulator may comprise an ecdysteroid. Thus, in an embodiment, the EcR modulator may comprise muristerone A (murA). Alternatively, the EcR modulator may comprise 20-hydroxyecdysone (20E). The modulator may be added to the assay system as a polypeptide. In additional and/or alternative embodiments, the modulator may comprise ponasterone A, 3-dehydro-20-hydroxyecdysone, ecdysone, makisterone A, nonsteroidal agonist including RH5849, RH59992, and the like. In another embodiment, the EcR modulator may be transfected into the cell as a DNA construct.

The methods and assay systems of the present invention may be designed to quantify and/or optimize the ability of compounds to interact with various isoforms of the nuclear receptor system. For example, in an embodiment, the isoforms of EcR comprise the *Drosophila* EcRA, EcRB1, or EcRB2 isoforms.

In one embodiment, the methods and assay systems of the present invention may employ a cell-based assay that is designed to have minimal background due to endogenous ecdysteroids. Thus, in one embodiment, the isolated cells used for transfection may comprise mammalian cells. Or, the isolated cells may comprise insect cells that do not have a EcR or that contain a non-functional EcR. For example, in one embodiment, insect cells that comprise EcR "knock-outs," in that the gene for EcR has been mutated to silence expression, may be used.

Various reporter systems may be used. The reporter construct may comprise a promoter having multiple hormone response elements (HREs) linked to a gene encoding a detectable gene product. The hormone response elements may recognize activated FXR and/or activated EcR. The response elements that may be used include the heat shock protein 27 (hsp 27) EcRE (Riddihough and Pelham, 1987, *EMBO J,* 6:3729-3734) or other elements such as a palindromic sequence separated by a single nucleotide (PAL1) or a direct repeat separated by four nucleotides (DR4) or five nucleotides (DR5) (e.g., Vogtli et al., 1998, *Nuc. Acids Res.,* 10: 2407-2414). In a further embodiment, the reporter gene may comprise chloramphenicol acetyltransferase (CAT). Alternatively, the reporter gene may comprise luciferase (LUC). Alternatively, the reporter gene may comprise green fluorescent protein (GFP).

The methods and assay systems of the present invention may comprise chimeric molecular substrates that allow for the analysis of structural and functional aspects of proteins involved in the modulation of insect growth and/or development. By using such chimeric molecular substrates, compounds that are targeted to specific portions of the receptor and/or its binding partner may be developed. Also, in an embodiment, different hormone response elements may be employed. For example, in one embodiment, the hormone response element may comprise an EcR response element, such as one found in the gene that encodes heat shock protein 27 (hsp27). Alternatively, the hormone response element may comprise a FXR response element such as that found in the ileal bile acid binding protein gene (Grober, et al., 1999, *J.*

Biol. Chem., 274:29749-29754). In an embodiment, the response element may be any nucleic acid sequence that responds to FXR or EcR to stimulate gene transcription.

Also, in an embodiment, site-directed mutagenesis or randomly generated mutations within the EcR or FXR LBD may be recovered. Such mutations may include sequences that enhance the induced responsiveness of the cell culture system, and/or reduce non-induced transcription levels while maintaining or increasing induced transcriptional activity, and/or change the specificity or induction properties of the receptor for the purposes of screening a subclass or potential insecticide compounds.

Also, the methods and assay systems of the present invention may use DNA constructs isolated from various species to develop species-specific insecticides. For example, it is known that USP or EcR from various species may have different activities. In one example embodiment, the FXR or EcR constructs and/or their respective heterologous binding partners may comprise species-specific constructs. Thus, the DNA encoding the ecdysone receptor (EcR) or the farnesoid X-activated receptor (FXR) may comprise a chimera of DNA from different insect or vertebrate sources. For example, the chimera may comprise a mammalian activating domain. Additionally and/or alternatively, the chimera may comprise a mammalian DNA binding domain (DBD) and/or a mammalian ligand binding domain (LBD). In alternate example embodiments, the mammalian receptor domains (e.g., activating, DBD, or LBD) may be derived from a mammalian glucocorticoid receptor (GR) or the farnesoid X-activated receptor. In another embodiment, the chimera may comprise an EcR-activating domain. Or, the chimera comprises an EcR DNA binding domain (DBD) and/or an EcR ligand binding domain (LBD). In one example embodiment, the EcR sequences may be derived from an arthropod. In an embodiment, the EcR sequences may be derived from *Drosophila melanogaster*. In yet another embodiment, the chimera may comprise a viral protein-16 (VP16) activating domain from pseudorabies virus. Or, the chimera may comprise *Chironomus tentans* (lower *Diptera*) (Cf) USP LBD, such as utilized in the VP16CfUSP construct. In other embodiments, portions of the activating domain, DNA-binding domain, and hinge region may be deleted from either the natural EcR or USP receptor. Or, one of three characterized mammalian (e.g., mouse, rat, or human) RXRs may be used as the heterologous binding partner. Domains (e.g., LBDs) from other insect species including *Manduca sexta* (Lepidoptera), *Locusta migratoria* (Orthoptera), *Heliothis virescens* (Leptidoptera), *Apis mellifera* (Hymenoptera), *Aedes aegypti* (lower Diptera), and *Tenebrio molitor* (Coleoptera) may also be employed.

The present invention also comprises a method that may be used to screen for insecticides in the environment. Thus, in an embodiment, the present invention comprises a method for in situ testing for the presence of compound having the ability to modulate insect growth comprising the steps of:

(a) transfecting a cell in an organism with DNA comprising sequences that encode a functional isoform of the farnesoid receptor (FXR) and/or the ecdysone receptor (EcR);

(b) cotransfecting the cell with: (i) DNA comprising sequences that encode a functional RXR or USP isoform; and (ii) DNA comprising a hormone response element (HRE) linked to a reporter gene;

(c) optionally, adding an ecdysteroid;

(d) exposing the organism to the compound to be tested; and (e) measuring an increase in the protein encoded by the reporter gene.

In an embodiment, the organism comprises an insect. For example, in an embodiment, the organism may comprise a transgenic *Drosophila* engineered to express heterologous EcR/USP peptides.

A variety of reporter constructs may be used. In an embodiment, the reporter construct may comprise a promoter comprising multiple hormone response elements (HRES) linked to a gene encoding a detectable gene product. For example, the reporter gene may comprise luciferase (LUC) or green fluorescent protein (GFP).

Also, in an embodiment, different hormone response elements may be employed. For example, in an embodiment, the hormone response element comprises an EcR response element. Alternatively, the hormone response element may comprise a FXR response element.

The heterologous binding partner may vary depending upon the DNA-receptor (e.g., FXR or EcR) being used. In one embodiment, the heterologous binding partner may comprise Ultraspiracle (USP). Alternatively, the heterologous binding partner may comprise vertebrate retinoid X receptor (RXR).

The EcR modulator may be one of several compounds known to interact with EcR and its heterologous binding partner. In one embodiment, the EcR modulator may bind to the ligand binding domain (LBD) of EcR. Or, the EcR modulator may bind to other portions of the EcR polypeptide. For example, the EcR modulator may comprise an ecdysteroid. Thus, in an embodiment, the EcR modulator may comprise muristerone A (murA). Alternatively, the EcR modulator may comprise or 20-hydroxyecdysone (20E). In additional and/or alternative embodiments, the modulator may comprise ponasterone A, 3-dehydro-20-hydroxyecdysone, ecdysone, makisterone A, nonsteroidal agonist including RH5849, RH59992, and the like. The modulator may be added to the assay system as a polypeptide. In another embodiment, the EcR modulator may be transfected into the cell as a DNA construct.

The assay system may be designed to quantify and/or optimize the ability of compounds to interact with various isoforms of the nuclear receptor system. For example, in an embodiment, the isoforms of EcR comprise the *Drosophila* EcRA, EcRB1, or EcRB2 isoforms.

Also, as described for the cell-based assay, site-directed mutagenesis or randomly generated mutations within the EcR or FXR (e.g., such as LBD mutants) may be recovered. Such mutations may include sequences that enhance the induced responsiveness of the cell culture system, and/or reduce non-induced transcription levels while maintaining or increasing induced transcriptional activity, and/or change the specificity or induction properties of the receptor for the purposes of screening a subclass or potential insecticide compounds.

Also, the assay may use DNA constructs isolated from various species to develop species-specific insecticides. For example, it is known that USP or EcR from various species may have different activities. In one example embodiment, the FXR or EcR constructs and/or their respective heterologous binding partners may comprise species-specific constructs. Thus, the DNA encoding the ecdysone receptor (EcR) or the farnesoid X-activated receptor (FXR) may comprise a chimera of DNA from different insect or vertebrate sources. For example, the chimera may comprise a mammalian activating domain. Additionally and/or alternatively, the chimera may comprise a mammalian DNA binding domain (DBD) and/or a mammalian ligand binding domain (LBD). In alternate example embodiments, the mammalian receptor domains (e.g., activating, DBD, or LBD) may be derived from a mammalian glucocorticoid receptor (GR) or the farnesoid X-activated receptor. In another embodiment, the chimera may comprise an EcR-activating domain. Or, the chimera comprises an EcR DNA binding domain (DBD) and/or an EcR ligand binding domain (LBD). In one example embodiment, the EcR sequences may be derived from an arthropod. In an embodiment, the EcR sequences may be derived from *Drosophila melanogaster*. In yet another embodiment, the chimera may comprise a viral protein-16 (VP16) activating domain from pseudorabies virus. Or, the chimera may comprise *Chironomus tentans* (lower Diptera) (Cf) USP LBD, such as utilized in the VP16CfUSP construct. In other embodiments, portions of the activating domain, DNA-binding domain, and hinge region may be deleted from either the natural EcR or USP receptor. Or, one of the three characterized mammalian (e.g., mouse, rat, or human) RXRs may be used as the heterologous binding partner. Domains (e.g., LBDs) from other insect species including *Manduca Sexta* (Lepidoptera), *Locusta migratoria* (Orthoptera), *Heliothis virescens* (Leptidoptera), *Apis mellifera* (Hymenoptera), *Aedes aegypti* (lower Diptera), and *Tenebrio molitor* (Coleoptera) may also be employed.

The present invention also comprises compounds that act as insecticides by their ability to inhibit insect growth. Also, the present invention may comprise a use for compounds identified using the methods and systems of the invention as insecticides and/or modulators of insect growth.

Thus, in another embodiment, the present invention comprises a composition for use as an insecticide comprising a compound that activates FXR-mediated transcription or EcR-mediated transcription mixed with a suitable carrier for application to plants.

In an embodiment, an increase of EcR-mediated transcription by the compound may comprise potentiation of hormone induced EcR transcription. Preferably, the hormone comprises an ecdysteroid. For example, the hormone may comprise murA or 20-hydroxyecdysone (20E).

Various natural compounds may be used as insect growth regulators and/or insecticides according to embodiments of the present invention. For example, in an embodiment, the compound that increases FXR-mediated transcription or EcR-mediated transcription may comprise farnesol or a farnesol metabolite. Also, the compound that increases FXR-mediated transcription or EcR-mediated transcription may comprise a juvenile hormone mimetic. Also, the compound that increases FXR-mediated transcription or EcR-mediated transcription may comprise a plant-derived JH agonist. In yet another embodiment, the compound that increases FXR-mediated transcription or EcR-mediated transcription may comprise an insecticide synergist. The compound that increases FXR-mediated transcription or EcR-mediated transcription may also comprise a monoterpene. In another embodiment, the compound that increases FXR-mediated transcription or EcR-mediated transcription comprises a diterpene. Or, the compound that increases FXR-mediated transcription or EcR-mediated transcription may comprise a triterpene. The compound that increases FXR-mediated transcription or EcR-mediated transcription may also comprise a furocoumarin. Or the compound that increases FXR-mediated transcription or EcR-mediated transcription may also comprise a phenylpropanoid. In another embodiment, the compound that increases FXR-mediated transcription or EcR-mediated transcription comprises a coumarin. Or the compound that increases FXR-mediated transcription or EcR-mediated transcription may comprise a flavonoid. Also, the compound that increases FXR-mediated transcription or EcR-mediated transcription may comprises a linoleic acid metabolite. Alternatively, the compound that increases FXR-mediated transcription or EcR-mediated transcription may comprise a polyketide. In yet another embodiment, the compound that increases FXR-mediated transcription or EcR-mediated transcription comprises a xanthine.

Also, compounds that increase FXR-mediated transcription or EcR-mediated transcription may comprise man-made compounds. For example, the compound that increases FXR-mediated transcription or EcR-mediated transcription may comprise an organochlorine.

A. Definitions

The following definitions may be used to understand the description herein. Unless defined otherwise, all technical and scientific terms used herein have the same meaning as commonly understood by one of ordinary skin in the art.

The term "a" or "an" as used herein may refer to more than one object unless the context clearly indicates otherwise. The term "or" is used interchangeably with the term "and/or" unless the context clearly indicates otherwise.

As used herein, a "ligand" is a molecule that interact either directly or indirectly with a receptor to form a complex.

An "agonist" comprises a compound that binds to a receptor to form a complex that elicits a pharmacological response specific to the receptor involved.

An "antagonist" comprises a compound that binds to an agonist or a receptor to form a complex that does not give rise to a substantial pharmacological response and can inhibit the biological response induced by an agonist.

"Polypeptide" and "protein" are used interchangeably herein to describe protein molecules that may comprise either partial or full-length proteins.

As used herein, a "polypeptide domain" comprises a region along a polypeptide that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

The term "vector" refers to a nucleic acid molecule that may be used to transport a second nucleic acid molecule into a cell. In one embodiment, the vector allows for replication of DNA sequences inserted into the vector. The vector may comprise a promoter to enhance expression of the nucleic acid molecule in at least some host cells. Vectors may replicate autonomously (extrachromasomal) or may be integrated into a host cell chromosome. In one embodiment, the vector may comprise an expression vector capable of producing a protein derived from at least part of a nucleic acid sequence inserted into the vector.

The term "fusion protein" may refer to a protein or polypeptide that has an amino acid sequence derived from two or more proteins. The fusion protein may also include linking regions of amino acids between amino acids portions derived from separate proteins. Unless specifically stated, there is no required order of linking polypeptides to form a fusion protein.

The term "percent identical" or "percent identity" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, *Adv. Appl. Math.*, 1981, 2:482; Needleman and Wunsch, 1970, *J. Mol. Biol.*, 48:443); Pearson and Lipman, 1988, *Proc. Natl. Acad. Sci. USA*, 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, percent identity of two sequences may be determined using GCG with a gap weight of 1, such that each amino acid gap is weighted as if it were a single amino acid or nucleotide mismatch between the two sequences.

An "effective amount" as used herein means the amount of an agent that is effective for producing a desired effect. Where the agent is being used to achieve a insecticidal effect, the actual dose which comprises the effective amount may depend upon the route of administration, and the formulation being used.

As used herein, "modulation of insect growth" includes the modulation of the growth of an individual insect or an insect population and includes modulation of insect reproduction, morphogenesis, and survival.

As used herein, "insect growth" comprises growth and development of an individual insect and/or an insect population and thus, refers to the growth, morphogenesis, and survival of an individual insect, or an insect population.

As used herein, an "increase in transcription" comprises an increase from a measurable basal level to a higher level. Alternatively, an "increase in transcription" may comprise an increase from an undetectable level to a measurable level.

As used herein, "activation of FXR" or "activation of EcR" describes increasing FXR-mediated transcription or EcR-mediated transcription, respectively.

As used herein, "FXR-mediated transcription" comprises a gene transcription event that requires binding of the activated farnesoid-X-receptor to a promoter upstream of the gene being transcribed.

As used herein, "EcR-mediated transcription" comprises a gene transcription event that requires binding of the activated ecdysone receptor to a promoter upstream of the gene being transcribed.

As used herein, "potentiation" of hormone activated transcription comprises an increase in transcription induced by hormones that bind to hormone response elements upstream of the gene being transcribed.

A "hormone response element" comprises a nucleotide region upstream of a gene that mediates the effect of a steroid hormone.

An "isoform" is a variant form of a protein that has the same general function as another protein but which may have small differences in its sequence either because it is encoded by a different gene, is expressed by a different promoter in the same gene, or is derived by alternative splicing of the same pre-mRNA. For example, EcR may exists in at least three versions having trans-activating regions that differ in sequence to provide isoforms EcRA, EcRB, and EcRB2, each of which can activate transcription of a gene having an EcR HRE in its promoter. EcRA is derived from a different promoter of the EcR gene, and B1 and B2 are derived from alternative splicing of a pre-mRNA.

A "ligand binding domain" is that portion of a protein or polypeptide involved in binding of a ligand.

A "juvenile hormone mimetic" is a compound that functions like any one of the natural juvenile hormones such as JHI, JH II, or JH III. The normal physiological functions of the naturally-occurring compounds are compromised by ectopic or exogenous administration of any number of juvenile hormone mimetic compounds.

An "insecticide synergist" is a compound that acts in synergy with an insecticide to provide a response that is greater than additive.

A "monoterpene" is an acyclic or cyclic $C_{10}$ hydrocarbon composed of two isoprene units and their oxygenated derivatives. Common monoterpenes include geraniol, limonene, α-pinene, camphor.

A "sesquiterpene" is an acyclic or cyclic $C_{15}$ hydrocarbon and their oxidized derivatives composed of three isoprene units.

A "diterpene" is a acyclic or cyclic $C_{20}$ hydrocarbon and their oxidized derivatives composed of four isoprene units.

A "triterpene" is a acyclic or cyclic $C_{30}$ hydrocarbon and their oxidized derivatives composed of six isoprene units.

As used herein "coumarin" is 2H-1-Benzopyran-2-one. A "furocoumarin" is a psoralen derivative of coumarin such as bergamotin.

As used herein "phenylpropanoid" is a compound derived from phenylalanine and cinnamic acid.

A "flavonoid" is a phenolic compound build up of two aromatic rings and held together by a C3 unite. Flavonoids include chalcones, isoflavanoids (rotenone), flavolignans (silybin).

As used herein, a "polyketide" included molecules synthesized form acetyl CoA, propionyl CoA, butyryl CoA, malonyl CoA, methylmalonyl CoA, and ehtylmalonyl CaA intermediates.

B. Juvenoids Potentiate Ecdysone Receptor-Dependent Transcription in a Mammalian Culture System The present invention recognizes that a variety of natural and synthetic insecticides can act to modulate transcriptional activity programmed by FXR. These putative insecticides may also potentiate *Drosophila* EcR-mediated transcription in the presence of limiting amounts of an ecdysone, thereby providing an assay system for the development of new insecticides. Thus, the present invention describes compounds that activate FXR and/or EcR as potential insecticides. The present invention also describes the use of such FXR-activating and EcR-activating and/or potentiating compounds isolated from plants or plant metabolites as environmentally friendly insecticides.

It has been shown that JH may act upon transcriptional activity, and may modulate the transcriptional regulation of ecdysteroids (Cherbas, L., et al., 1989, *Dev. Genet.*, 10:177-188; Farkas, R., and J. Knopp, 1997, *Arch. Insect Biochem. Physiol.*, 35, 71-83; Hiruma, K., et al., 1999, *Dev. Genes*

*Evol.*, 209, 18-30; Zhou, X., and L. M. Riddiford, 2002, *Development*, 1290: 2259-2269). Despite its apparent importance for insect processes, a single receptor for JH has not been definitively demonstrated in any insect or developmental period (Wyatt, G. R., and K. G. Davey, 1996, *Adv. Insect Physiol.*, 26, 1-155; Dubrovsky, E., et al., 2002, *Insect Biochem. Mol. Biol.* 32:1555-1565).

Although a receptor that activates transcription in response to ecdysones (EcR) has been reported (Koelle, M. R., et al., 1991, *Cell* 67:59-77), one that mediates the transcriptional effects of JHs still has not been defined. The ability of FXR to induce transcription in response to farnesol and metabolites such as JH III indicates that this nuclear receptor homolog of EcR may exhibit pharmacologic features expected of an insect JH receptor (Forman, B. M. et al., *Cell* 1995, 81:687-693).

It appears that both FXR and EcR may interact with a heterologous binding partner as a prerequisite to activating transcription of developmental genes. Ultraspiracle (USP), is a nuclear receptor that may dimerize with the ecdysone receptor (EcR) to form the functional ecdysteroid receptor complex (Thomas, H. E., et al., 1993, *Nature*, 362:471-475; Yao, T. P, et al., 1993, *Nature*, 366:476-479; Riddiford, L. M, et al., 2000, *Vitam. Horm.*, 60: 1-73). USP is an insect orthologue of the vertebrate retinoid X receptor (RXR) (Oro, A. E., et al., 1990, *Nature*, 347:298-301), which itself is responsive to the JH agonist, methoprene acid, but not to methoprene itself (Harmon, M. A., et al., 1995, *Proc. Natl. Acad. Sci., USA* 92:6157-6160). USP has been implicated as a JH receptor based on its ability to mediate a transcriptional response to methyl epoxyfarnesoate (JHIII) via a direct repeat (DR12) response element in insect cells (Jones, G., et al., 2001, *Insect Biochem. Mol. Biol.*, 32: 33-49; Xu., Y., et al., 2002, *Eur. J. Biochem.*, 269, 6026-6036).

Whereas USP has garnered considerable attention for its possible mediation of JH effects, little note has been paid to the similarity of USP's partner, the ecdysone receptor (EcR), with the vertebrate farnesoid-activated X receptor (FXR). FXR is a nuclear receptor that strongly activates transcription (e.g., by about 10-fold to 20-fold) by JHIII when assayed in a mammalian cell culture system (Forman, B. M., et al., 1995, *Cell*, 81:687-695). FXR induces transcription from a promoter containing the heat shock protein 27 (hsp27) ecdysone response element (EcRE) (Riddihough, G., and H. R. Pelham, 1987, *EMBO J.*, 6:3729-3734). The ligand-binding domain (LBD) of rat FXR shows about 40% amino acid identity with *Drosophila* EcR.

The present invention recognizes that there may be overlap between the mammalian FXR/RXR system and the insect EcR/USP systems, and provides numerous plant-derived and man-made JHs that have the ability to increase transcriptional activity programmed by FXR and/or EcR. Thus, in various embodiments, the present invention comprises assay systems and methods to test various EcR isoforms and chimeras as having the ability mediate a transcriptional response to ecdysteroids and JHs. The ability to reconstitute ecdysteroid responsive transcriptional effects in an otherwise non-responsive mammalian cell culture (Christopherson, K. S., et al., 1992, *Proc. Natl. Acad. Sci. USA*, 89:6314-6318) by transfection with EcR may offer a strategy for testing compounds for FXR or EcR induced transcriptional activity as well as any possible effects of juvenoids. Because the assay is performed in mammalian cells which normally lack endogenous FXR and EcR activity, components required for activity may be controlled.

Figure 1B:
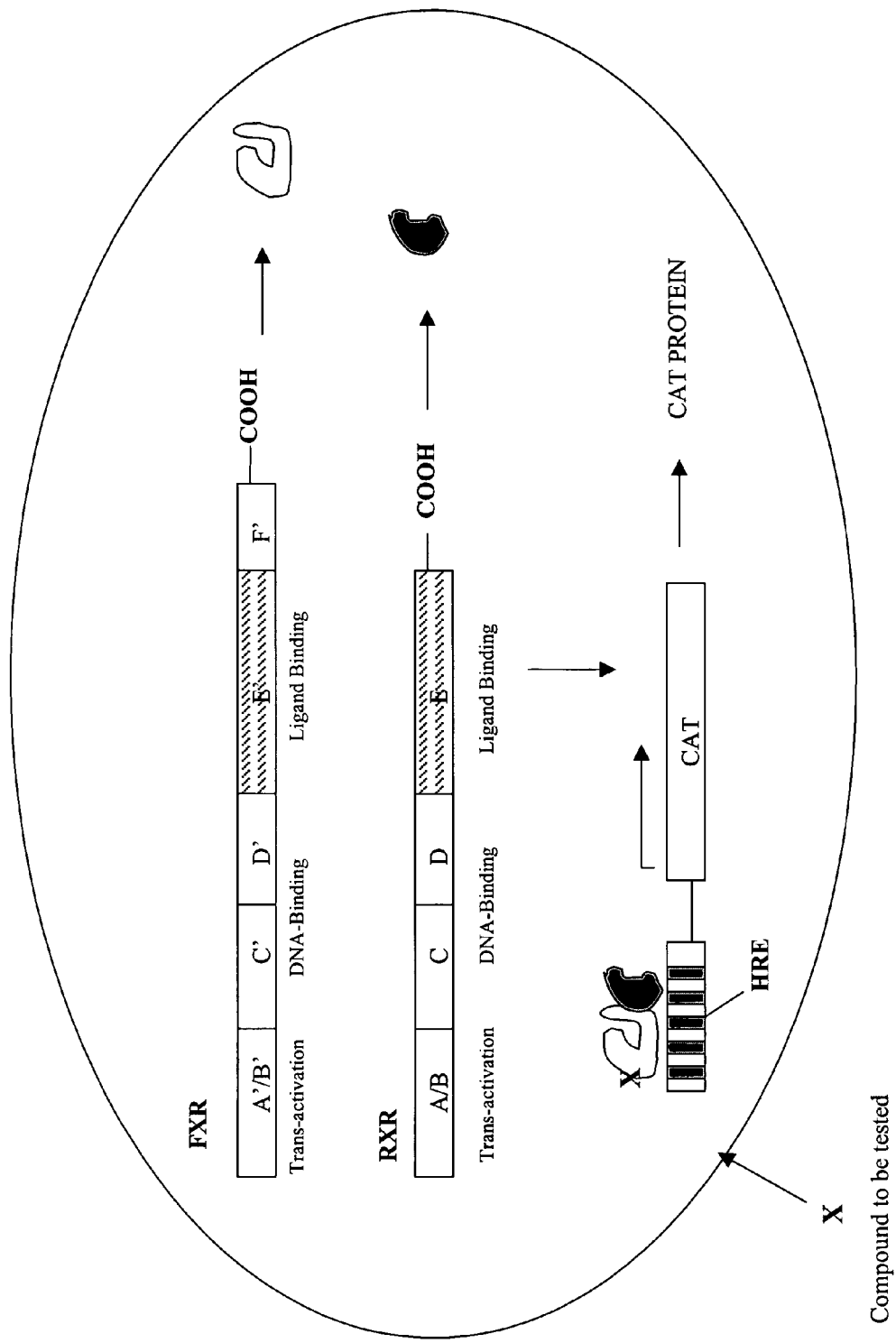

Thus, the present invention comprises methods and systems to evaluate the ability of specific compounds to activate either FXR or EcR mediated transcription, wherein compounds exhibiting the ability to activate EcR or FXR mediated transcription comprise potential modulators of insect growth and/or insecticides. Example embodiments of assay systems of the present invention are depicted schematically in FIGS. 1A and 1B. The assay systems as depicted in FIGS. 1A and 1B are non-limiting in that the mechanism of interaction of the various assay components may vary from that depicted in the drawing, while still providing a functional assay system. For example, in one embodiment, the compound to be tested, (X), may bind directly to FXR or EcR protein as indicated schematically in FIG. 1. Alternatively, compound (X) may modify FXR (or EcR) activity without directly binding to the protein, but indirectly in some manner.

As shown in FIG. 1A, the assay system may comprise four components. The first component may comprise a DNA construct that encodes a functional EcR. For example, in one embodiment, a cell (shown as the large oval in FIG. 1) may be transfected with a plasmid comprising sequences that encode an EcR polypeptide. In one embodiment, the EcR polypeptide may comprise an EcR chimera comprising a mammalian (e.g., human) glucocorticoid receptor (GR or hGR) transactivation domain (A/B) attached to an insect (e.g., *Drosophila*) EcR DNA binding domain and hinge (DBD) (C/D) and ligand binding domain (LBD) (E). Also, in some cases the construct may contain a region (F) that may function as a transactivation domain (Palli, S. R. et al., 2003, *Eur. J. Biochem.*, 270:1308-1315) The second component of the assay may comprise the binding partner needed for EcR (or FXR) activity. In one embodiment, a cell may therefore be co-transfected with a second expression plasmid comprising sequences that encode a mammalian RXR (e.g., mouse, rat, or human RXRα) or an insect USP. These proteins may also comprise a trans-activating domain (A/B) and a DNA binding domain (C) and hinge (D), and a ligand binding domain (E). In an embodiment, RXR and/or USP may not necessarily comprise an (F) domain. The plasmids may be co-transfected into a mammalian cell, such as a Chinese Hamster Ovary (CHO) cell, so that there is no endogenous EcR or ecdysteroid present. The third component of the assay system may be an exogenous ecdysteroid such as muristerone A (murA), that may act to induce EcR dependent transcription. Finally, the assay system may comprise a means to measure EcR- or FXR-mediated transcription. The response of transfected cells to a compound (X) that is able to increase FXR-mediated transcription or EcR-mediated transcription may be measured using a reporter plasmid bearing a EcR (or FXR) hormone responsive element (HRE). In one embodiment, the reporter plasmid may comprise a construct having multiple copies of the hormone-responsive element inserted upstream of a gene having a measurable gene product. In one example embodiment, multiple copies of an ecdysone-responsive element, hsp27 EcRE, are inserted into the mouse mammary tumor virus (MTV) promoter positioned upstream of the bacterial chloramphenical acetyltransferase gene to generate an $(EcRE)_5$-ΔMTV-CAT reporter plasmid. The compound to be tested (X) may then added to the cells, and the effect on FXR or EcR activated transcription of the CAT gene is determined.

In an alternative embodiment, the reporter gene may comprise the luciferase gene (LUC) or a green fluorescent protein (GFP). For example, in an embodiment, the reporter plasmid comprises an $(EcRE)_5$-ΔMTV-LUC construct produced as described herein. Using the luciferase gene may allow for FXR or EcR activated transcription to be measured in-situ by monitoring the luminescence of the cells or organism being used in the assay.

FIG. 1B shows a non-limiting example embodiment of an assay system for FXR-mediated transcription and measurement of the ability of a compound, (X), to modulate FXR-mediated transcription. In this assay system, a hormone, such as murA, may not be required. Thus, in the assay system shown in FIG. 1B, compound (X) may modify transcription of the reporter gene that is mediated by FXR, but that does not require or employ murA. As described for FIG. 1A, the compound to be tested, (X), may bind directly to FXR or EcR protein, or it may modify FXR (or EcR) activity without directly binding to the protein, but indirectly in some manner.

Figure 2:
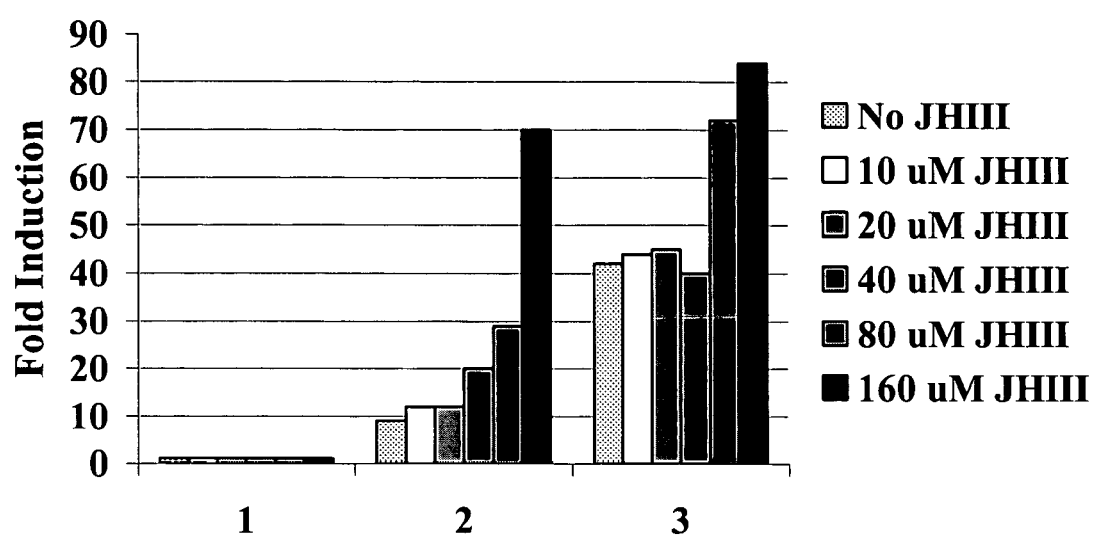
FIG. 2 shows the potentiating effects of juvenile hormone III (JHIII) dosage on the muristerone-A (murA) induced response mediated by a GRdEcR chimera and mouse RXR (mRXR) using a chloramphenical acetyltransferease (CAT) reporter construct (EcRE)$_5$-ΔMTV-CAT in mammalian Chinese Hamster Ovary (CHO) cells in accordance with example embodiments of the present invention. Sets 1, 2 and 3 correspond to 0, 0.01 and 0.1 μM murA.

For example, cells may be transfected with plasmids comprising a GRdEcR chimera that consists of the rat glucocorticoid receptor (GR) activation domain (A/B) attached to the *Drosophila melanogaster* (d or Dm) EcR DNA binding domain (DBD) (C/D) and ligand binding domain (LBD) (E), and a second plasmid comprising mouse RXR (mRXRα). The response of transfected cells to the ecdysteroid, murA, may be measured using a (EcRE)$_5$-ΔMTV-CAT reporter plasmid that carries five tandem repeats of the hsp27 EcRE linked to the MTV promoter and the chloramphenicol acetyltransferase (CAT) gene. For example, using the assay system of the present invention, a response (an increase in CAT activity) is detected upon addition of the EcR ligand, muristerone A (murA), at doses as low as 0.1 μM (FIG. 2). For FIG. 2, sets 1, 2 and 3 correspond to 0 mur A, 0.01 μM murA and 0.1 μM murA. In an embodiment, only amounts of hormone (e.g., muristerone A) that comprise submaximal levels of induction of EcR transcription are added to the assay system to detect signals from test compounds. Thus, in alternate embodiments, the dose of hormone may range from 0.001 μM to 5.0 μM, or from 0.005 μM to 0.5 μM, or from 0.01 μM to 0.1 μM.

In an embodiment, the transfected cells comprise mammalian cells. By using mammalian cells as the host, cofactors and transcription factors are present, but there may be minimal background activity due to endogenous ecdysone receptor and/or ligands. Any cell type that does not normally respond to ecdysteroids, but having the required transcription factors is a potentially suitable cell type for the assay.

Various combinations of the steroid activation pathway may be employed in the assay of the present invention. Thus, in one embodiment, the present invention comprises the use of specific receptor isotypes to evaluate potential insecticides. For example, in an embodiment, the assay may use an arthropod (e.g., insect) ecdysone receptor (EcR), an insect USP, and a suitable reporter gene construct (e.g., CAT or luciferase linked to a HRE specific to FXR or EcR). Alternatively, the assay may comprise using an insect EcR with a mammalian RXR, and a suitable reporter gene construct. In yet another embodiment, the assay may comprise use of an FXR construct in combination with a mammalian RXR construct. Or, the assay may comprise using FXR in combination with USP. Several non-limiting example embodiments for assay systems of the present invention are summarized in Table 1.

TABLE 1

| Ligand binding | Heterologue | Reporter construct | Hormone | Assay System | Application |
| --- | --- | --- | --- | --- | --- |
| GCdEcR | USP | (EcRE)$_5$-ΔMTV-LUC/CAT | Yes | Mammalian | Cell-based assay for insecticides |
| VP16-EcR | USP | (EcRE)$_5$-ΔMTV-LUC/CAT | Yes | Mammalian | Cell-based assay for insecticides |
| GCdEcR | RxR | (EcRE)$_5$-ΔMTV-LUC/CAT | Yes | Mammalian | Cell-based assay for insecticides |
| VP16EcR | RxR | (EcRE)$_5$-ΔMTV-LUC/CAT | Yes | Mammalian | Cell-based assay for insecticides |
| FXR | RxR | (EcRE)$_5$-ΔMTV-LUC | No | Mammalian | Environmental Screening |
| FXR | RxR | (EcRE)$_5$-ΔMTV-CAT/LUC | No | Mammalian | Cell based assay for insecticide |
| EcRA | USP | (EcRE)$_5$-ΔMTV-LUC/CAT | Yes | Mammalians | Cell-based assay for insecticides |
| EcRB1 | USP | (EcRE)$_5$-ΔMTV-LUC/CAT | Yes | Mammalians | Cell-based assay for insecticides |
| EcRB2 | USP | (EcRE)$_5$-ΔMTV-LUC/CAT | Yes | Mammalians | Cell-based assay for insecticides |

As indicated in Table 1, the DNA constructs used for the present invention may be chimeras. Nuclear receptors, such as EcR and FXR, may comprise three general domains structural domains: (1) a transcriptional activating domain—A/B; (2) a DNA binding (DBD)—C; and (3) a hinge (D) and ligand binding domain (LBD) (E) (FIG. 1). As used herein, the hinge (D) may be considered as part of the DBD (C) or the LBD (E) when describing various nuclear receptor protein constructs. Also, for some receptors, a C-terminal (F) domain may comprise trans-activation characteristics. For example, in one example embodiment, the EcR construct, GCdEcR, may comprise the human glucocorticoid receptor (GC) or (hGC) activating domain (e.g., A/B) and the *Drosophila* (d or Dm) EcR DNA binding domain (C) and the *Drosophila* hinge-ligand binding domain (D/E). Or, a VP16EcR construct comprising the VP16 activating domain (VP16) in combination with *Drosophila* EcR DBD and LBD domains (EcR) may be used. The assay may also comprise a construct, GGEc, comprising the human glucocorticoid receptor (G) trans-activating domain and DBD with the *Drosophila* EcR (Ec) LBD. The assay may also comprise a construct, GEcEc, comprising the human glucocorticoid receptor (G) activating domain and the *Drosophila* (Ec) DBD and LBD. In yet another embodiment, the assay may comprise a construct, GGF, comprising the human glucocorticoid receptor (G) activating domain and DBD with the FXR (F) LBD derived from vertebrate species (avian, rodent, human). In yet another embodiment, the assay comprises a construct, VP16CfUSP, comprising the VP16 activation domain directly linked to the LBD (i.e., D/E domains) of *Choristoneura fumerifana* (Cf) (spruce budworm) USP. In another embodiment, the VP16 trans-activating domain may be linked to the *Drosophila* USP protein DBD and LBD to generate the contruct, VP16-DmUSPDBD-DmUSPLBD. Or, natural isoforms of Dm EcR with A/B domains A, B1 or B2 with the F domain deleted (Mouillet etla., 2001) may be used. Table 2 provides several non-limiting constructs that may be used with the methods and systems of the present invention, utilizing nomenclature that is standard in the art.

TABLE 2

Receptor Domain Composition of Plasmid Expression Vectors

| Construct | A/B-Trans-Activation | C-DNA Binding Domain (DBD) | D/E-Hinge-Ligand Binding Domain (LBD) |
|---|---|---|---|
| GCdEcR or GEcEc or GRdEcR* | hGR | Dm EcR | Dm EcR |
| GGEc | hGR | hGR | Dm EcR |
| GGF | hGR | hGR | FXR |
| VP16EcR | VP16 | Dm EcR | Dm EcR |
| VP16CfUSP | VP16 | — | Cf USP |
| VP16DmUSPDmUSP | VP16 | Dm USP | Dm USP |
| EcRA | EcRA | Dm EcR | Dm EcR |
| EcRB1 | EcRB1 | Dm EcR | Dm EcR |
| EcRB2 | EcRB2 | Dm EcR | Dm EcR |
| VP16USPF1 | VP16/DmA/B fusion | Dm USP | Dm USP |
| VP16USPF2 | VP16 | Dm USP | Dm USP |
| VP16USPF3 | VP16 | — | Dm USP |
| mRXRα | Mouse RXR | Mouse RXR | Mouse RXR |

*As used herein, glucocorticoid receptor elements may be designated as G, GC, or GR.

Also, standard RXR and USP expression plasmids may be used in the assay of the present invention. As is known in the art, expression plasmids may have promoter elements and polyadenylation signals between which nucleic acid sequences encoding the amino acids of interest are positioned. For RXR and USP expression plasmids, the plasmids produce RXR or USP proteins in the presence of the appropriate transcription factors. Promoter elements for the RXR and USP proteins may be such as to drive transcription in a constitutive fashion. These typically include those from Rous sarcoma virus or cytomegalovirus.

The use of chimeric DNA constructs allows for the construction of nuclear receptors which interact with mammalian transcriptional factors to induce or repress transcription mediated by the DBD and/or LBD of the insect receptor, EcR, and its partner, USP. Because the mammalian cells do not contain endogenous EcR or USP, there is little or no endogenous response to the experimental ligand.

The A/B domain of EcR may be responsible for modifying transcriptional activity of the receptor. In one embodiment, various isoforms of the EcR A/B domain (e.g., A, B1, or B2) may be used for the EcR construct (Tables 1 and 2 and described herein). In one embodiment, the system may display specificity between a particular EcR isoform and the heterodimeric partner or the ability of the EcR to respond to the test agent (X). Conversely, different EcR/USP and EcR/RXR heterodimeric combinations display different responsiveness to the test agent (X).

In an embodiment, juvenile hormones (JHs) can potentiate the effect of EcR ligands. For example, a GRdEcR chimera, that consists of the human glucocorticoid receptor activation domain (GR) attached to the *Drosophila melanogaster* (d) EcR DBD and LBD was cotransfected with mouse RXR (mRXR) into CHO cells. Using an $(EcRE)_5$-ΔMTV-CAT reporter gene, it was found that juvenile hormone III (JHIII) may potentiate the response of murA in a dose-dependent manner (using 20, 40, 80, and 160 μM JHIII) at submaximal ecdysteroid dosages (0.1 μM and 1 μM murA) (FIG. 2, sets 2 and 3, respectively). Also, although JHs can potentiate the effects of ecdysteroid ligands, JHIII may not increase the response above the maximal response seen with high concentrations of the ecdysteroid. Thus, using the assay described for FIG. 2, JHIII does not evoke a response that is greater than the maximal level induced by 10 μM murA.

The use of a mammalian cell-based assay system allows for controlled addition of the components required for activity. Thus, in one embodiment, juvenile hormones do not interact with unbound EcR, but require addition of submaximal levels of exogenous hormone for activity. For example, despite the structural resemblance between the LBDs of EcR and the vertebrate FXR, which is highly responsive to JHIII alone (Forman et al., 1995, *Cell*, 81:687-693), JHIII alone shows no effect on transcription mediated by the GRdEcR chimera with RXR (FIG. 2, set 1).

Using the assay system of the present invention, the interaction between various molecular components of the insect developmental pathway may be optimized. For example, ecdysteroid responsiveness and JHIII potentiation in EcR chimeras may depend, at least in part, upon the activating ligand being used. Ecdysteroid responsiveness and JHIII potentiation in EcR chimeras may also depend upon and the heterodimeric partner used in the assay system. For example, transfection of mammalian CHO cells with the VP16 activation domain linked to the DBD and LBD of *Drosophila melanogaster* (Dm or d) EcR, may result in a sensitive and robust ecdysteroid response to muristerone A.

Figure 3:
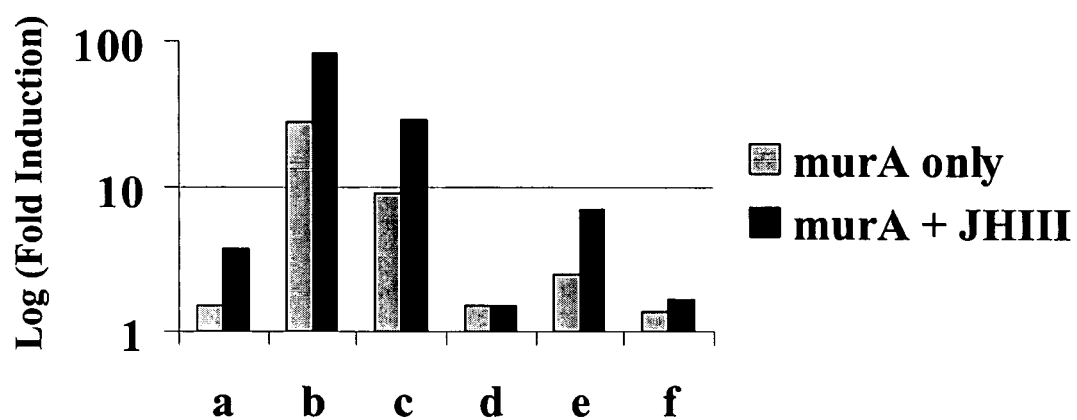
FIG. 3 shows the ecdysteroid response and potentiation effects of JHIII (log fold induction based on normalized activity in relative light units (RLUs)) using a luciferase reporter gene (EcRE)$_5$-ΔMTV-LUC in CHO cells, and measured for various EcR combinations and mouse RXR (mRXR) in accordance with example embodiments of the present invention, wherein the constructs used were as follows: (3A) VP16dEcR/mRXR at 0.01 μM murA; (3B) VP16dEcR/mRXR at 0.1 μM murA; (3C) VP16dEcR/VP16CfUSP at 0.1 μM murA, (3D) EcRA/mRXR at 1 μM murA; (3E) EcRB1/mRXR at 0.1 μM; (3F) EcRB2/mRXR at 0.1 μM murA.

FIG. 3 shows the ecdysteroid response and potentiation effects of JHIII measured for various EcR combinations and mouse RXR in accordance with an embodiment of the present invention. As shown in FIG. 3, mouse RXR was used as the heterologous dimer and a luciferase construct, $(EcRE)_5$-ΔMTV-LUC, was used as the reporter gene. Shown in FIG. 3 are: VP16dEcR/mRXR at 0.01 μM murA (3*a*); VP16dEcR/mRXR at 0.1 uM murA (3*b*); VP16dEcR/VP16CfUSP at 0.1 μM murA (3*c*); EcRA/mRXR at 1 μM murA (3*d*); EcRB1/mRXR at 0.1 μM (3*e*); and EcRB2/mRXR at 0.1 μM murA (3*f*), each in the presence, or absence, of 80 μM JHIII.

It may be seen that the various constructs may display differing activity profiles. For example, VP16dEcR (viral transactivation A/B domain linked to *Drosophila* (EcR) LBD and DBD) partnered with mouse RXR may respond to 0.01 μM and 0.1 μM murA (FIGS. 3*a* and 3*b*). The response of the VP16dEcR/mRXR system is generally strong and robust as compared to other combinations of binding and transcriptional activation units. Also, the response of the VP16dEcR/mRXR system may be further potentiated by JHIII. The VP16dEcR chimera may also display a discernible response to 20E at 10 μM (e.g., over 20-fold) using RXR. VP16dEcR/20E activity is not, however, necessarily potentiated by JHIII. In one embodiment, VP16dEcR/RXR in the presence of 20E is only minimally affected by the additional presence of JHIII (not shown).

As described herein, the assay of the present invention may allow for the mixing of different molecular constructs as a means to better understand the molecular nature of insect development and insecticide structure and function. In one embodiment, the VP16dEcR construct may also be tested with VP16CfUSP (Table 2) (FIG. 3*c*). Using this system, the same degree of potentiation may occur for murA using the VP16EcR/USP combination as with the VP16dEcR/RXR complex, except that a higher murA dose may be required to achieve the same efficacy. Although the normalized level of JHIII-mediated potentiation of the murA response is similar with either RXR or VP16CfUSP, the combination of VP16dEcR with VP16CfUSP may shows little to no response to 10 μM 20E and is not affected by the additional presence of JHIII (not shown).

The assay of the present invention provides for the use of different ecdysone receptor isoforms, either natural or generated by mutagenesis, as a means to evaluate the activity of various test compounds. In an alternate embodiment, the assay may comprise the use of various FXR isoforms, either natural or generated by mutagenesis (Zhang, Y, et al., 2003, *J. Biol. Chem.* 278: 104-110). To evaluate the activity of the various EcR isoforms, selected EcR isoforms, such as the three natural *Drosophila melanogaster* EcR isoforms, EcRA, EcRB1, and EcRB2, may be cotransfected into CHO cells with either USP or RXR expression plasmids such as, but not limited to, the VP16CfUSP and/or VP16CRXR fusion proteins. The different EcR isoforms (e.g., *Drosophila* A, B1, and B2) may be selected to differ at the N-terminal region of the protein, which is the part of the protein involved in dimerization of EcR with either USP, RXR or other appropriate partners. In an embodiment of the assay of the present invention, the isoforms (e.g., A, B1, and B2) may display unique expression profiles among each other and as compared to VP16dEcR/RXR (not shown).

The activity observed among the three EcR isoforms may depend, at least in part, upon the identity of the heterologous partner used. For example, when tested in the absence of hormone, the EcRB1/VP16CfUSP combination shows a relatively high level of ligand-independent transcription, with between 10 and 20-fold higher basal levels than other EcR constructs. Also, the EcRA isoform in combination with VP16CfUSP may also show a basal level of transcription that is 2 to 3 fold higher than the basal level of transcription obtained with EcRB2 isoform. In contrast, the basal activity of the EcRB2/VP16CfUSP dimer may be about the same as the basal activities produced by VP16dEcR/RXR and GREcR/RXR (not shown).

Figure 4:
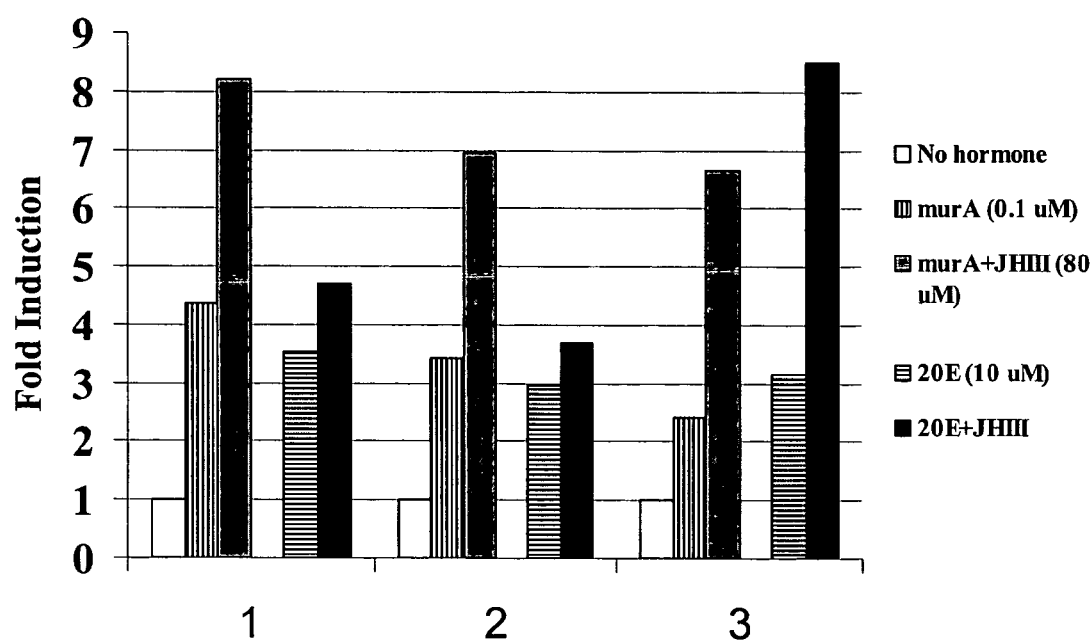
FIG. 4 shows the effects of murA, 20E, and JHIII on RLU activity induced by (EcRE)$_5$-ΔMTV-LUC in CHO cells cotransfected with *Drosophila* EcR isoforms and VP16CfUSP in accordance with example embodiments of the present invention where sets 1, 2, and 3 in the figure correspond to EcRA, EcRB1 and EcRB2, respectively.

In an embodiment, with VP16CfUSP, all three *Drosophila* isoforms (A, B1 and B2) may be induced by about 30-40 fold at 1 μM murA. Also in an embodiment, the response of all EcR isoforms in the presence of VP16CfUSP is potentiated by the presence of 80 μM JHIII in the presence of 0.1 μM murA. Data showing induction of isoforms A (set 1), B1 (set 2) and B2 (set 3) by murA, and potentiation by JHIII is shown in FIG. 4. In a further embodiment, the JH potentiation is dose-dependent, similar to the results seen with GrdEcR.

Responsiveness of the natural EcR isoforms to the ecdysteroid 20E may require USP (rather than RXR) as a dimeric partner. In yet a further embodiment, among the three isoforms (EcRA, EcRB1, and EcRB2), JHIII potentiation in the presence of 20E may occur only with EcRB2 isoform and USP. For example, at a dosage of 10 μM 20E, all three *Drosophila* EcR isoforms and VP16CfUSP generate a consistent and discernible transcriptional response. Only the EcRB2/VP16CfUSP dimer (FIG. 4, set 3) is potentiated significantly by the additional presence of JHIII, however. That only the B2 EcR isoform is potentiated by JHIII in the presence of 20E indicates that activation by JHIII may depend upon both the N-terminal domain of EcR and the activating ecdysteroid.

Specific combinations of the EcR N-terminal domain and the heterodimeric partner (e.g. VP16 and RXR, B2 and USP) may therefore result in a functional receptor that is capable of showing an ecdysteroid response and/or JHIII potentiation. Also, in one embodiment of the assay system, the potentiation by JHs is not due to the activation of RXR by either JHIII or a JHIII metabolite, as JHIII by itself shows no potentiation of transcriptional activity.

The differential ecdysteroid- and JHIII-dependent transcriptional activities noted among the EcR isoforms may offer insights concerning the lack of correspondence between cellular isoform titers and developmental effects in *Drosophila* tissues. The B isoforms may be functionally distinguished from the EcRA isoform (Bender, M., et al., *Genetics* 91:777-788), and recent studies have distinguished biological roles for B1 and B2 (Cherbas, L., et al., 2003, *Development* 130:271-284). Also, the B2 N-terminal domain is shorter than the B1 N-terminal domain, and is capped with an amphipathic helix (Talbot, W. S., et al., 1993, *Cell* 73: 1323-1337; Hu et al, 2003). Interestingly, alternative isoforms in the rat FXR also differ greatly in their ability to mediate ligand-dependent transcriptional activity (Zhang, Y, et al., 2003, *J. Biol. Chem.* 278: 104-110).

Figure 5:
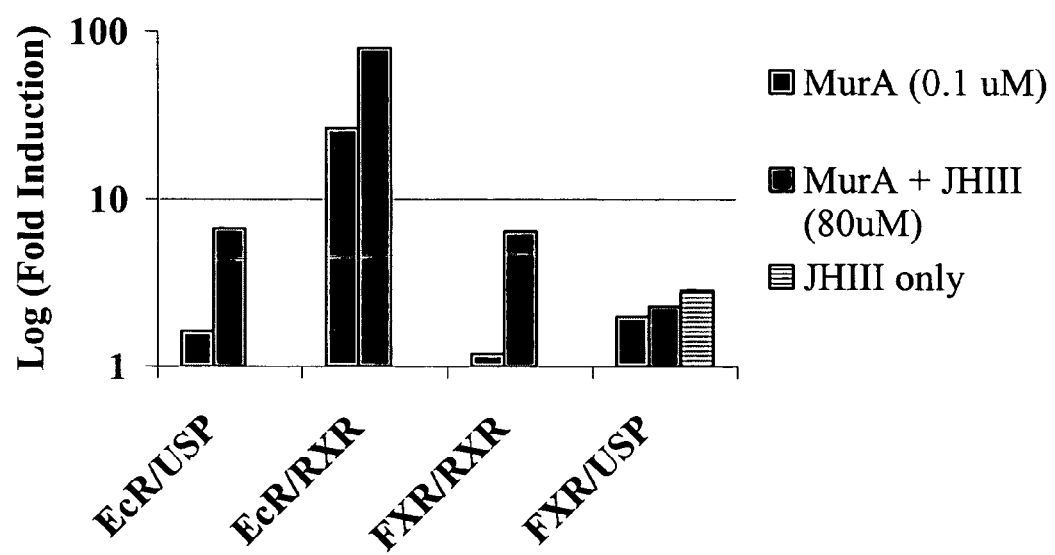
FIG. 5 shows the response of various combinations of nuclear receptors and their binding partners to muristerone A and JHIII in CHO cells in accordance with example embodiments of the present invention, where EcR refers to VP16dEcR, USP refers to VP16CfUSP, and FXR and RXR refer to natural mammalian forms.

In selected embodiments of the present invention, combinations of EcR/USP, EcR/RXR, and FXR/RXR show a response to murA that may be potentiated by JH (FIG. 5). In contrast, the combination of FXR with USP may not respond to JHIII. Thus, whereas the FXR activator JHIII can potentiate the transcriptional response of EcR induced by ecdysteroids, it appears that in at least some embodiments, the JHIII response exhibited by FXR may require RXR, and not USP, as a heterodimeric partner. Thus, in at least some systems, USP and RXR may not be interchangeable. Also, the presence of a ligand-bound EcR may be a prerequisite for observing the potentiative effects of JHIII on EcR. Assays using the various EcR forms indicate that multiple factors may influence receptor activity, including the activating ecdysteroid, the N-terminal domain of EcR, and the heterodimeric partner.

In one embodiment, the combination of FXR and USP may evoke a low level response in CHO cells to JHIII (FIG. 5) attributable to endogenous expression of low levels of RXR in these cells, where the addition of ecdysteroids (murA or 20E)

with JHIII induces no further elevation of FXR/USP-mediated activity (FIG. 5). Also, EcR and USP may be unable to potentiate a response to 20 µM chenodeoxycholic acid (CDCA), the most efficacious naturally-occurring activator of FXR known to date.

A summary of ecdysteroid responsiveness and JHIII potentiation among various combinations of EcR with either RXR or USP proteins (Table 3) shows that murA may exhibit activity with a wider range of ecdysteroid receptor heterodimers and may be more potent than 20E. Further, the EcR combination may influence responsiveness. For example, all three isoforms (EcRA, EcRB1, and EcRB2) may be potentiated by JHIII when murA is the activating ligand. In contrast, for 20E, only the B2/USP may be substantially potentiated by JHIII. Also, in an embodiment, of the three isoforms, only EcRB1 acts with RXR. In contrast to the activity seen with murA, the three isoforms may respond to 20E only in conjunction with their natural partner, USP. Thus, it appears that 20E responsiveness may involve a compatibility between the N-terminal domain of EcR and the heterodimeric partner. In one embodiment, the high level of B1 basal activity may relate to a cell-specific aspect of CHO cultures, as this effect has not been seen in HeLa cells. The selectivity of the 20E responsiveness may be further substantiated by the ability of the VP16dEcR/VP16CfUSP combination to respond only to murA, but not to 20E.

TABLE 3

A summary of ecdysteroid responsiveness and JHIII potentiation among various combinations of EcR with either RXR or USP proteins

| Ecdysone Receptor | MurA | | MurA + JHIII | | 20E | | 20E + JHIII | |
|---|---|---|---|---|---|---|---|---|
| Description | RXR | USP | RXR | USP | RXR | USP | RXR | USP |
| GRdEcR | + | n.d | + | n.d | − | n.d. | − | n.d. |
| VP16dEcR | ++ | + | + | + | + | − | − | − |
| EcRA | − | + | − | + | − | + | − | − |
| EcRB1 | + | + | + | + | − | + | − | − |
| EcRB2 | − | + | − | + | − | + | − | + |

Proteins are described in Examples 1 and 2.
+ designates a change in transcriptional level that exceeds 2.5-fold,
++ indicates a response at a lower dosage than other EcR forms.
Responses are based on dosages of 0.1 µM murA, 10 µM 20E, and 80 µM JHIII.
For murA and 20E, (+) indicates inducibility; for columns involving JHIII, (+) indicates observed potentiation that exceeds 2-fold above the levels observed with ecdysteroid alone.

The activating ecdysteroid may also determine the ability of JHIII to potentiate a response in other EcR dimers. For instance, the VP16dEcR/RXR combination is responsive to both 20E and murA; but when 20E is used, JHIII may not be capable of potentiating the response, whereas JHIII strongly potentiates the murA response.

In an embodiment, EcR, bound to its cognate ligand, may acquire a conformation that allows further activation by JHIII either directly or via an indirect interaction. Also, the amount of ligand-bound EcR may be limiting factor in the cell-based assay of the present invention. For example, while the amount of potentiation JHIII potentiation may remain constant over a range of submaximal murA doses, the absolute transcriptional activity attributable to a fixed JHIII dose may increase as ecdysteroid molarity increases, indicating that the number of ligand-activated EcR proteins may be a rate-limiting factor.

The mechanism of JHIII potentiation for EcR/USP may be different from effects of JH analogues on RXR. RXR may be activated through its LBD by methoprene acid, a metabolite of methoprene, and with the retinoic acid receptor (RAR) generates a response to the ligand through a direct repeat element (Harmon et al., 1995). Known RXR ligands may also increase the responsiveness of VP16dEcR to murA via the hsp27 response element (Saez, E., et al., 2000, *Proc. Natl. Acad. Sci. USA*, 97:14512-14517) to supra-maximal levels. In contrast, potentiation of EcR by JHIII occurs at a submaximal hormone response through already activated EcR molecules. Also, RXR ligands activate the VP16EcR/RXR complex even when ecdysteroids are not bound to the EcR partner (Saez et al., 2000). By contrast, the effects of JHIII in the assay of the present invention may require the simultaneous presence of ecdysteroids for any response to be observed.

B. The Farnesoid X-activated Receptor (FXR) and Ecdysone Receptor (EcR) as Strategic Targets For the Development of Compounds that Modulate Insect Growth Farnesol was the first molecule to be recognized as a juvenoid (P Schmialek, 1961, *Z. Naturf.*, 16b: 461-464). For example, the most widely distributed juvenile hormone (JH) in the arthropod world, JH III, was synthesized via bioassay-guided structural optimization based upon farnesol (Bowers, W. S., et al., 1965, *Life Sci.*, 4:2323-2331) prior to its identification from insect extracts (Roller, H., et al., 1967, *Angew. Chem. Int. Ed.*, 6:179-180). The use of rational design has provided a platform for the development of numerous drugs and vaccines important for human and veterinary health, and provides a conceptual basis for the future design of more effective insecticides. In rational design, biologically important molecules are characterized by comparing structure with activity in order to identify functional groups that either enhance, alter, or block activity. Farnesol is metabolized from farnesyl diphosphate, a precursor to cholesterol, ubiquinones, dolichols, and other growth-requiring isoprenoids (Goldstein, J. L., and M. S. Brown, 1990, *Nature* 1990, 343:425-430). Using the methods and assay systems of the present invention, it has been determined that compounds derived from everyday plants, such as farnesol and other juvenoids, and including those that may constitute a portion of the human diet, may comprise the ability to activate FXR and/or EcR (i.e., to increase FXR-mediated transcription or EcR-mediated transcription, repectively) and thus, may function as insecticides and/or insect growth regulators.

Figure 6:
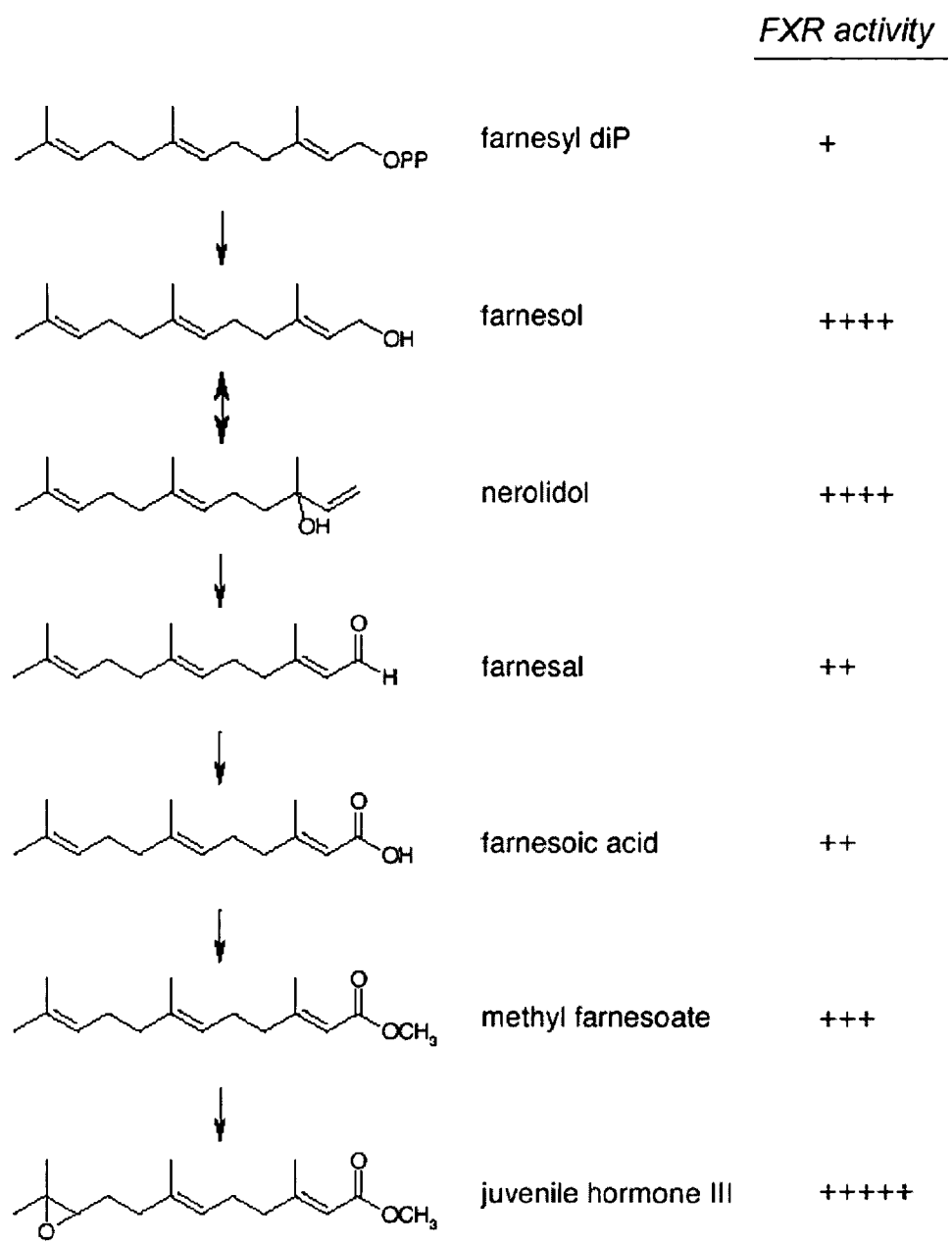
FIG. 6 shows that FXR may be activated by sesquiterpene metabolites of farnesyl diphosphate in accordance with example embodiments of the present invention wherein the relative efficacy of each isoprenoid as an inducer of FXR-dependent transcription is displayed.

In one embodiment, the compounds that increase FXR and/or increase or potentiate EcR-mediated transcription comprise farnesol metabolites. As shown in FIG. 6, farnesyl diphosphate is metabolized to juvenile hormone III (FIG. 6), and at least some of the intermediate metabolites may interact with FXR to induce RXR mediated transcription. For example, farnesol, nerolidol, and JHIII may induce FXR greater than 10-fold. Also, in an embodiment, farnesal, farnesoic acid, and methyl farnesoate, also interact with FXR to induce RXR mediated transcription.

Also, the compounds that increase FXR-mediated transcription, and/or increase or potentiate EcR-mediated transcription, may comprise juvenile hormone mimetics. For example, FXR-activating famesoids have been described as JH agonists in insect bioassays (Schneiderman, H. A., and L. I. Gilbert, 1964, *Science*, 1964, 143:325-333). Thus, in one example embodiment, the JH mimetics comprise farnesol, neorlidol, and phytol (Table 4), as well as the synthetic juvenoids methoprene, pyriproxyfen, and the ethyl ester of 7,11-dicholoro-2-ene farnesoic acid (FIG. 7A).

TABLE 4

JH and FXR Activities of Isoprenoids and Chemicals

| ISOPRENOID | JH ACTIVITY a (units/g) | FXR ACTIVITY (fold-induction) |
| --- | --- | --- |
| cecropia oil | 1000 | N.T. |
| phytol | 32 | 3 |
| isophytol | 0 | N.T. |
| all-trans farnesol | 140 | 9 |
| farnesal | 32 | 2 |
| farnesyl acetate | 5.4 | 12 |
| farnesenic [farnesoic] acid | 7.8 | 3 |
| hexahydrofarnesol | 0 | N.T. |
| nerolidol | 8.9 | 9 |
| linalool | 0.08 | 1 |
| geraniol | 0 | 1 |
| geranyl linalool | 0.14 | N.T. |
| solanesol | 0.05 | N.T. |
| juvenile hormone III | — | 20 |
| methoprene | — | 15 |
| pyriproxyfen | — | 9 |
| fenvalerate | — | 12 | a From Schneiderman and Gilbert, Science 143: 325–329 (1964).
N.T. = not tested;
FXR activity of "1" indicates that the FXR-dependent transcriptional induction was less than 2-fold when tested at doses below cytotoxicity. Chemicals were tested at a final dose of 50 ∝M.

In another embodiment, the compounds that increase FXR-mediated transcription, and/or increase or potentiate EcR-mediated transcription, comprise plant-derived JH agonists. In one example embodiment, the plant derived JH agonists that increase FXR-dependent transcription, and/or increase or potentiate EcR-mediated transcription, comprise echinacea oil, echinolone, juvocimene, juvabione, α-bisabolol, olive oil, 2-hydroxyphenethlyl alcohol, 3-hydroxyphenethlyl alcohol, or 4-hydroxyphenethlyl alcohol (FIG. 7B).

In another embodiment, the compounds that increase FXR-mediated transcription and/or increase or potentiate EcR-mediated transcription comprise insecticide synergists. In a further embodiment, the insecticide synergists that increase FXR-dependent transcription, and/or increase or potentiate EcR-mediated transcription, comprise piperonyl butoxide (PB), seasamin, sesame oil, piperine, myristicin, or apiole (FIG. 7C).

In an embodiment, the compounds that increase FXR-mediated transcription, and/or increase or potentiate EcR-mediated transcription, comprise monoterpenes. In a further embodiment, the monoterpenes that increase FXR-dependent transcription, and/or increase or potentiate EcR-mediated transcription, comprise tea tree oil (terpenen-4-ol, 1,8-cineole, and α-terpineol), carvacrol, thymol, perillyl alcohol, fenchyl alcohol, or pinane diol (Table 4 and FIGS. 8A and 8B).

The compounds that increase FXR-mediated transcription, and/or increase or potentiate EcR-mediated transcription, may also comprise diterpenes. In a further embodiment, the diterpenes that increase FXR-dependent transcription, and/or increase or potentiate EcR-mediated transcription, comprise forskolin, 1-trans-$\Delta^9$-tetrahydrocannabinol (THC), abietic acid, croton oil, and other phorbol-like diterpenes such as phorbol 12,13-dibutyrate, mezerein, and also ingenol 3,20-dibenzoate, cafestol, kahweol, or their acetate derivatives.

Also, the compounds that increase FXR-mediated transcription, and/or increase or potentiate EcR-mediated transcription, may comprise triterpenes. In yet a further embodiment, the triterpenes that increase FXR-dependent transcription, and/or increase or potentiate EcR-mediated transcription, comprise essential oils from myrrh and frankincense, β-boswellic acid, oleanolic acid, rosemary oil, or 20α- or 20R-hydroxycholesterol.

Figure 8A:
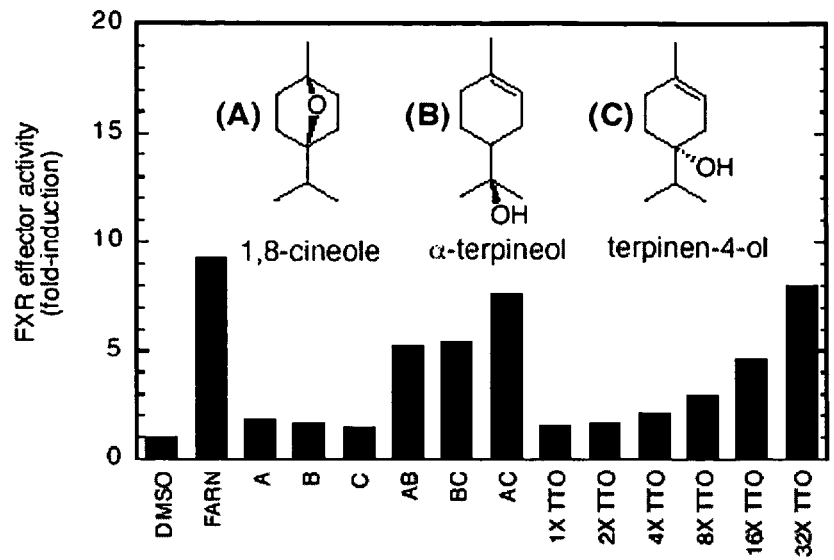
FIG. 8 shows FXR activation profiles for plant secondary metabolites and congeners in accordance with example embodiments of the present invention, wherein the following compounds were tested for FXR activation: (8A) tea tree oil and constituents α-terpineol, 1,8-cineole, and terpinen-4-ol (added individually at 800 µM or together at 400 µM and compared with increasing amounts of tea tree oil (TTO)); (8B) coffee diterpenes cafestol acetate and kahweol acetate; (8C) cucurbitacin D (cuc D) (1 µM) added to cells with, or without, farnesol (45 µM) or chenodeoxycholic acid (CDCA) (40 µM); (8D) bergamot ingredients bergamotin, 5-methoxypsoralen, and 8-methoxypsoralen; (8E) methylenedioxyphenyl compounds myristicin, methyleugenol, and safrole; (8F) rotenone and rotenonic acid with a cleaved furan ring; (8G) hops ingredients isoxanthohumol (IX); xanthohumol (XN); and 8-prenylnaringenin (8PN); and (8H) xanthines caffeine (CF), theophylline (TP), xanthine (XT), hypoxanthine, and theobromine (TB) (not shown).
Figure 8B:
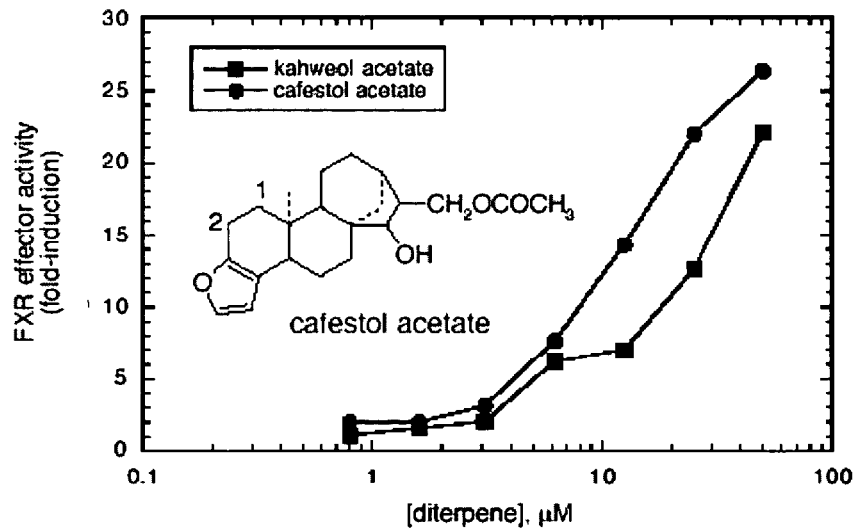
Figure 8C:
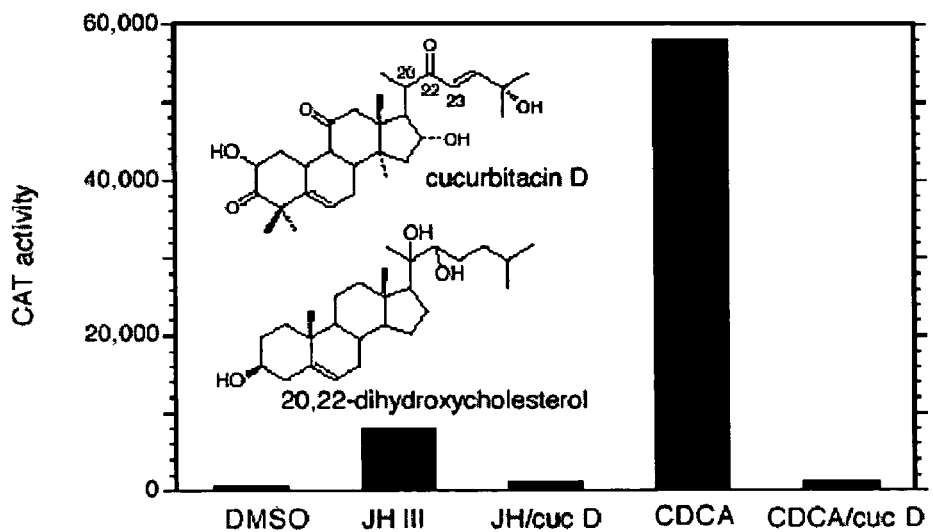

The present invention also comprises compound that can suppress the activity of FXR or EcR. Compounds that inhibit the ecdysone receptor (EcR) may suppress FXR activity. Also, the compounds that inhibit FXR activity may suppress FXR activity promoted by FXR modulators. In one example embodiment, 1 μM cucurbitacin D (cuc D) may suppress FXR-dependent activity promoted by JH III and chenodeoxycholate (CDCA) (40 μM each), 7-fold and 58-fold, respectively (FIG. 8C). Also, the $\Delta^1$-unsaturated congener cucurbitacin I may inhibit farnesol-induced activity with an IC$_{50}$ ~50 nM (data not shown).

Figure 8D:
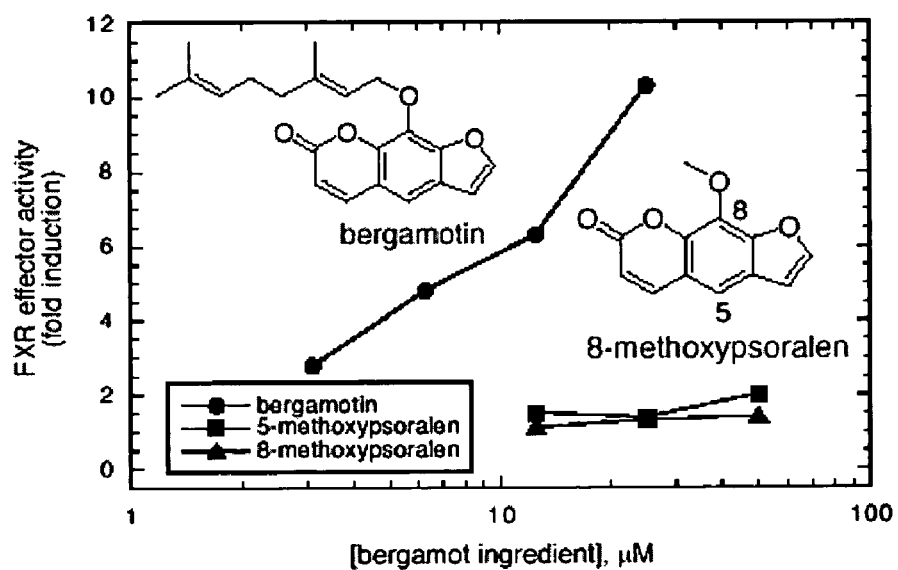
Figure 8E:
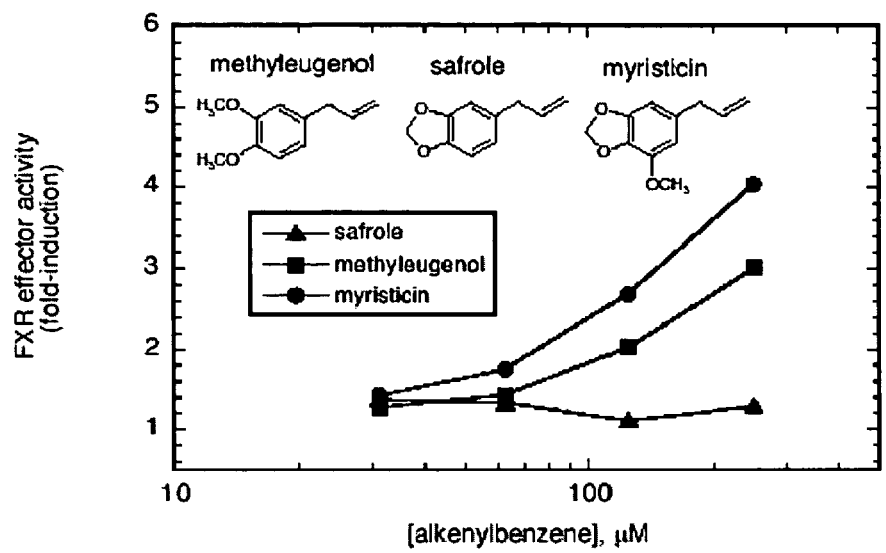

The compounds that increase FXR-mediated transcription, and/or increase or potentiate EcR-mediated transcription, may also comprise furocoumarins or phenylpropanoids. In one example embodiment, the fucocoumarins and phenylpropanoids that increase FXR-dependent transcription, and/or increase or potentiate EcR-mediated transcription, comprise the furocoumarins, bergamot oil and bergamotin (from Earl Grey tea) (FIG. 8D), myristicin, or apiole, or the phenylpropanoid, methyleugenol (FIG. 8E).

In other embodiments of the present invention, the compounds that increase FXR-mediated transcription and/or increase or potentiate EcR-mediated transcription may comprise coumarins and flavanoids. The coumarins and flavanoids that increase FXR-dependent transcription may, for example, comprise silybin, tangeretin or a rotenonic acid (FIG. 8F) or 8-prenylnaringenin and isozantholhumol from hops.

The compounds that increase FXR-mediated transcription, and/or increase or potentiate EcR-mediated transcription, may also comprise linoleic acid metabolites. In yet a further embodiment, the linoleic acid metabolites that increase FXR-dependent transcription, and/or increase or potentiate EcR-mediated transcription, comprise cis-jasmone or methyl jasmonate.

Figure 8F:
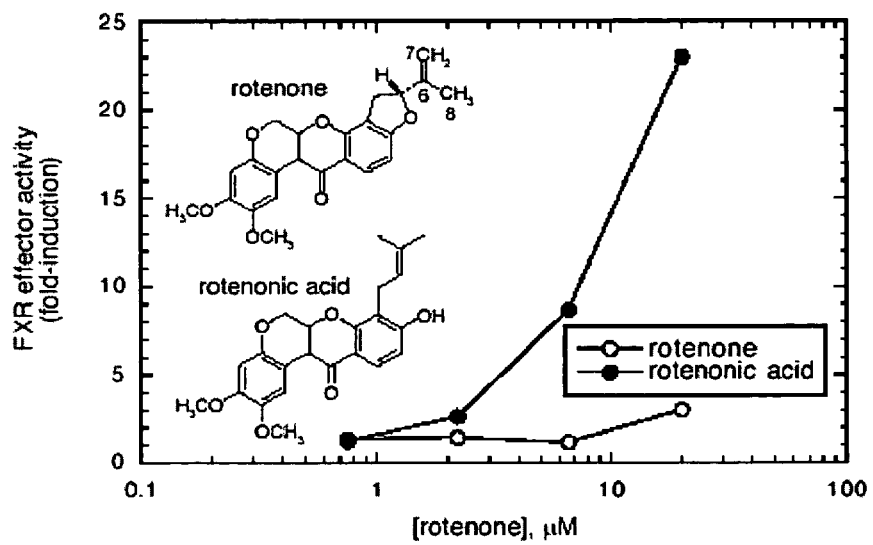
Figure 8G:
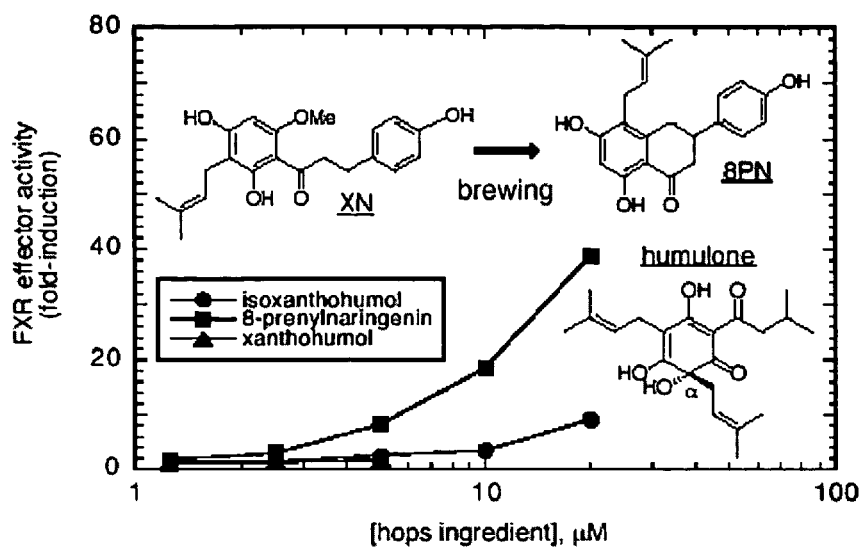

Also, in an embodiment, the compounds that increase FXR-mediated transcription and/or increase or potentiate EcR-mediated transcription comprise polyketides from hops. In yet a further embodiment, the polyketides that increase FXR-dependent transcription, and/or increase or potentiate EcR-mediated transcription, comprise humulone (FIG. 8G).

Figure 8H:
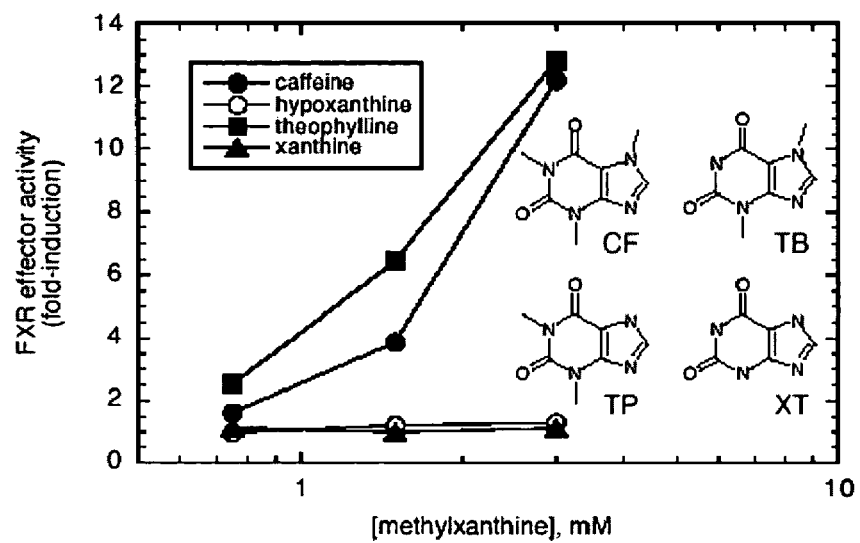

Also, in an embodiment, the compounds that increase FXR-mediated transcription and/or increase or potentiate EcR-mediated transcription comprise xanthines. In yet a further embodiment, the xanthines that increase FXR-dependent transcription, and/or increase or potentiate EcR-mediated transcription, comprise theophylline, caffeine, 8-Br-cAMP, dibutyryl cAMP, or 8-Br-cAMP in combination with theophylline (FIG. 8H).

In an embodiment, man-made insecticides may increase FXR-mediated transcription and/or increase or potentiate EcR-mediated transcription. For example, in an embodiment, man-made insecticides that increase FXR-mediated transcription, and/or increase or potentiate EcR-mediated transcription, comprise cinerins, pyrethrins, jasmolins, synthetic pyrethroids including cypermethrin, permethrin, phenothrin, and bioallethrin (Table 5).

TABLE 5

FXR Activation by Plant Essential Oils and Ingredients

| PLANT OIL | FXR ACTIVITY | INGREDIENT | DOSE (µM) | FXR ACTIVITY* (fold-induction) |
|---|---|---|---|---|
| allspice | 7 | | | |
| balm | 4 | | | |
| balsam fir | 3 | juvabione | | |
| basil | 10 | juvocimene | 25 | 9 |
| bergamot | 10 | bergamotin | 25 | 10 |
| | | bergapten | 100 | 1 |
| black pepper | N.T | piperine | 50 | 4 |
| cardomom | 3 | | | |
| cassia bark | 1 | | | |
| cedarwood | 9 | α-ionone, β-ionone | 150 | 10 |
| clove | 3 | eugenol | 200 | 1 |
| coffee | N.T | caffeine | 3000 | 12 |
| | | theophylline | 3000 | 12 |
| | | caffeic acid | 100 | 1 |
| | | cafestol | 20 | 12 |
| | | kahweol | 20 | 10 |
| *coleus forskholi* | N.T | forskolin | 10 | >100 |
| cottonseed | 1 | | | |
| croton | 3 | ingenol-3,20-dibenzoate | 10 | 5 |
| derris | N.T | rotenone | 20 | 1 |
| | | rotenonic acid | 20 | 20 |
| *Echinacea* | 7 | echinolone | | N.T. |
| Fennel | 7 | | | |
| Frankincense | 30 | β-boswellic acid | 25 | 11 |
| Ginger | 4 | | | |
| Hops | 18 | 8-prenylnaringenin | 20 | 38 |
| | | Humulone | 20 | 8 |
| | | Xanthohumol | | 1 |
| | | Isoxanthohumol | 20 | 9 |
| | | Lupulone | 20 | 1 |
| milk thistle | 4 | silybin | 100 | 10 |
| myrrh | 22 | | | |
| nutmeg | N.T. | methyleugenol | 250 | 4 |
| olive oil | 4 | phenethyl alcohols | 400 | 4 |
| orange | N.T. | limonene | 300 | 1 |
| | | perillyl alchol | 300 | 4 |
| *origanum* | 6 | carvacrol | 300 | 6 |
| | | thymol | 300 | 6 |
| parsley | N.T. | myristicin | 250 | 4 |
| | | safrole | 250 | 1 |
| pyrethrum | 10 | pyrethrin | | N.T. |
| | | cinerin | | N.T. |
| | | jasmolin | | N.T. |
| rice | N.T. | γ-tocotrienol | 20 | 1 |
| sage | 8 | | | |
| sesame | 3 | sesamin | 100 | 12 |
| | | sesamol | | 1 |
| spruce | N.T. | abietic acid | 50 | 23 |
| tea tree | 8 | 1,8-cineole | 400 | 2 |
| | | α-terpineol | 402 | |
| | | terpinen-4-ol | 400 | 2 |
| thyme | 13 | | | |
| vetiver | 24 | | | |
| ylang ylang | 17 | cis-jasmone | 1000 | 6 |
| | | methyl jasmonate | 1000 | 18 |

*FXR activity is defined as the ratio of FXR-dependent CAT activity attained in appropriately transfected cells at maximal doses of plant oil (or indicated doses of ingredients) over that for the vehicle. Activity level of "1" indicates no increase in activity over vehicle.

Figure 9:
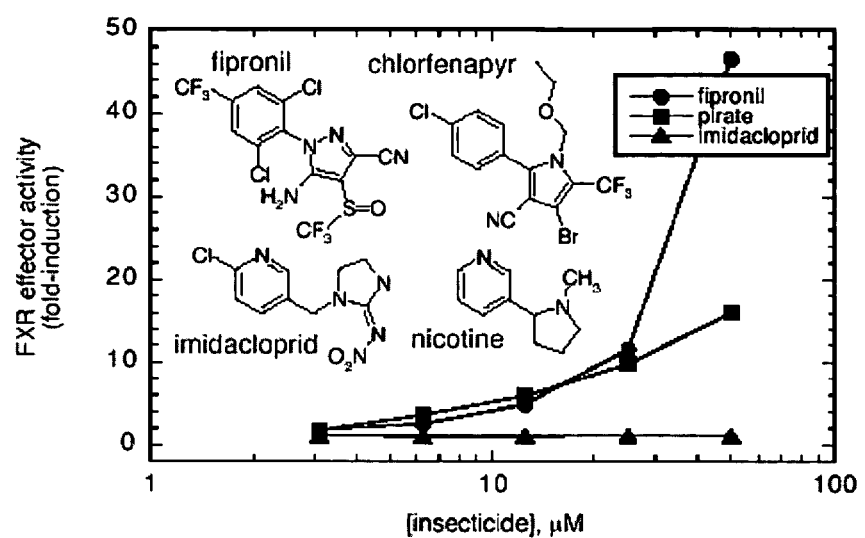
FIG. 9 shows FXR-mediated transcription may be increased by phenylpyrazole insecticides in accordance with an example embodiment of the present invention, wherein increasing doses of fipronil, chlorfenapyr (pirate), and imidacloprid were tested as indicated for the ability to increase FXR-mediated transcription.

Also, insecticides such as o,p-DDT (but not p,p-DDT), chlordane, kepone, lindane, dieldrin, toxaphenes, aroclor 1254, 2,3,7,8-tetrachlorodibenzo-p-dioxin, malathion, diazinon, chlorpyrifos, parathion, ethion, chlorfenapyr, pyrethrin, permethrin, fenvalerate, or fipronil may increase FXR-mediated transcription and/or increase or potentiate EcR-mediated transcription in an embodiment of the present invention (Table 6; FIG. 9).

TABLE 6

FXR Is Activated by Synthetic Insecticides

| COMPOUND | STRUCTURE | DOSE (µM) | FXR ACTIVITY (fold-induction) |
|---|---|---|---|
| chlordane | 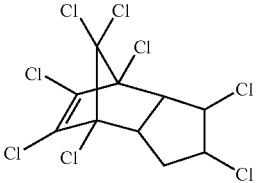 | 5 | 7 |
| o,p-DDT | 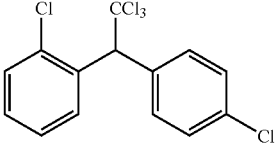 | 5 | 3.5 |
| dieldrin | 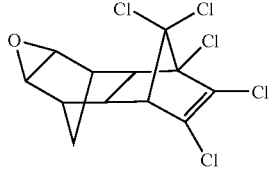 | 5 | 17 |
| tetrachlorodibenzo-p-dioxin | 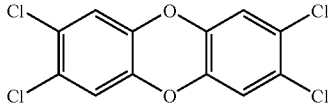 | 0.1 | 15 |
| malathion | 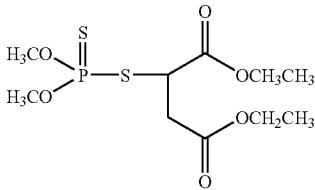 | 50 | 13 |
| diazinon | 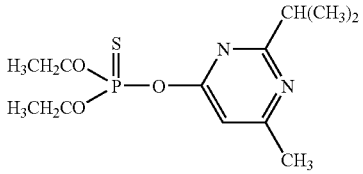 | 50 | 33 |
| phosdrin | 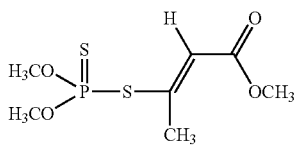 | 100 | 1 |

TABLE 6-continued

FXR Is Activated by Synthetic Insecticides

| COMPOUND | STRUCTURE | DOSE (μM) | FXR ACTIVITY (fold-induction) |
|---|---|---|---|
| pyrethrin I (pyrethrum extract) | 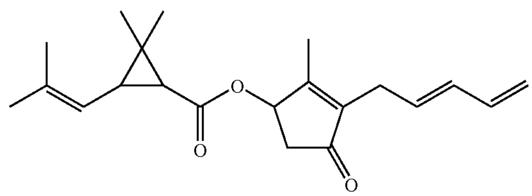 | Maximum | 10 |
| permethrin | 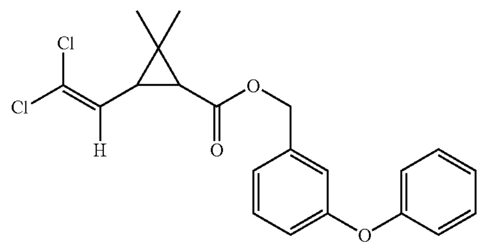 | 25 | 5 |
| fenvalerate | 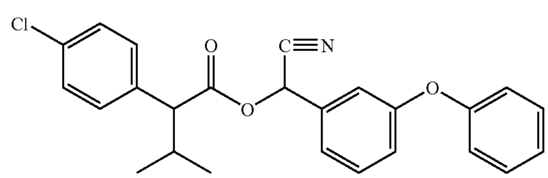 | 25 | 9 |

The present invention recognizes that small doses of ecdysone may prime the EcR-dependent transcriptional response provoked by JHs. Ecdysones may stabilize a conformation of EcR that permits JHs to bind more effectively. Since JH potentiators may affect the maximal transcriptional response elicited by ecdysone, this may be similar to allosteric enzymes whose effectors alter the apparent $V_{max}$ without changing the $K_m$ value. Thus, the variable cytotoxicities provoked by dietary or ectopically-applied ecdysones, JHs, or insecticides in different insects may be uniquely imparted by their pharmacologically-distinguishable EcR/USP complexes.

In one embodiment, the present invention describes the use of JH antagonists as compound that may be used to modulate insect growth. In one embodiment, the JH antagonists may increase FXR-mediated transcription. Alternatively, the JH antagonists may inhibit FXR-mediated transcription.

Figure 10A:
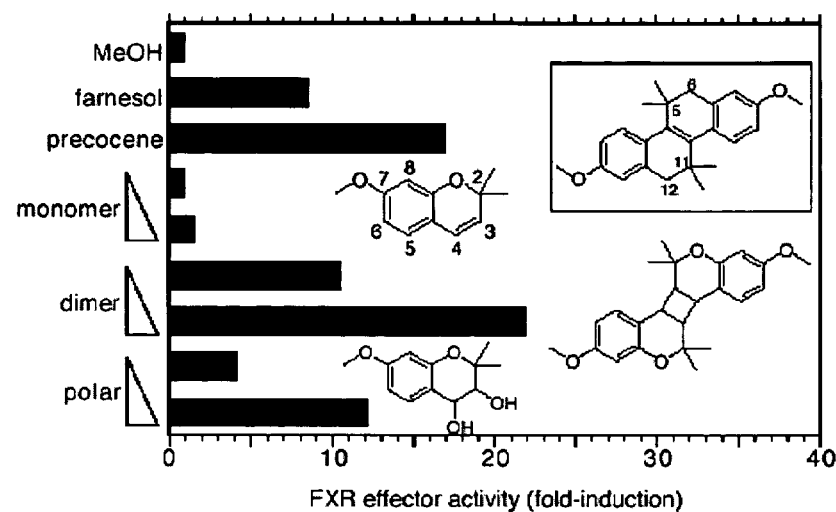
FIG. 10 shows that FXR-mediated transcription may be inhibited or stimulated by metabolites or analogues of the JH antagonist precocene in accordance with example embodiments of the present invention wherein: (10A) shows TLC separation of precocene isoforms and comparison of FXR effector activities; (10B) shows that microsome-treated precocene I generates FXR antagonists; (10C) shows molecular structures of precocene-like analogs that increase or inhibit FXR-dependent activity; (10D) inhibition of farnesoid (F)-induced FXR-dependent transcription mediated by esculetin (E); (10E) shows that FXR-mediated transcription is inhibited by ubiquinone-1, wherein the indicated doses of ubiquinone-1 were added to CHO cells transfected with plasmid DNAs to measure agonist activity and identical doses were added with 30 µM farnesol (F) to measure antagonist activity; and (10F) shows that FXR-mediated transcription is increased by ubiquinone-2, wherein indicated doses of ubiquinone-2 were tested for ability to increase FXR-mediated transcription and compared with farnesol (45 µM).
Figure 10B:
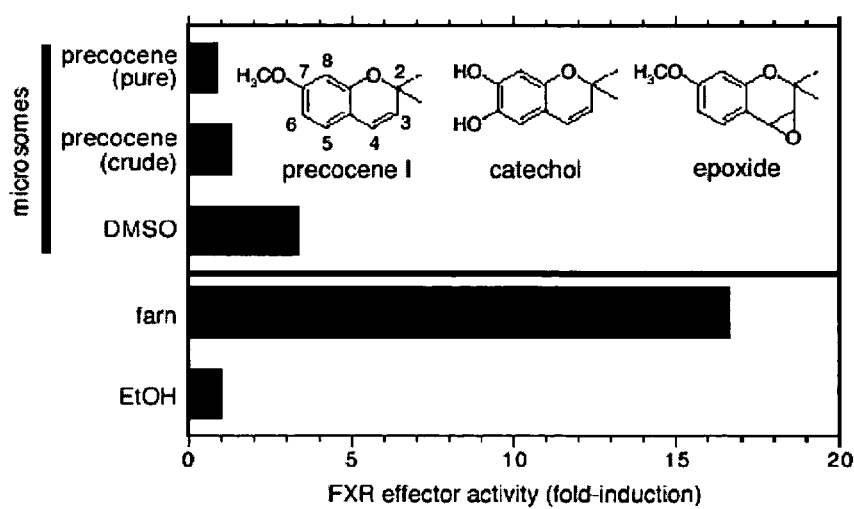
Figure 10C:
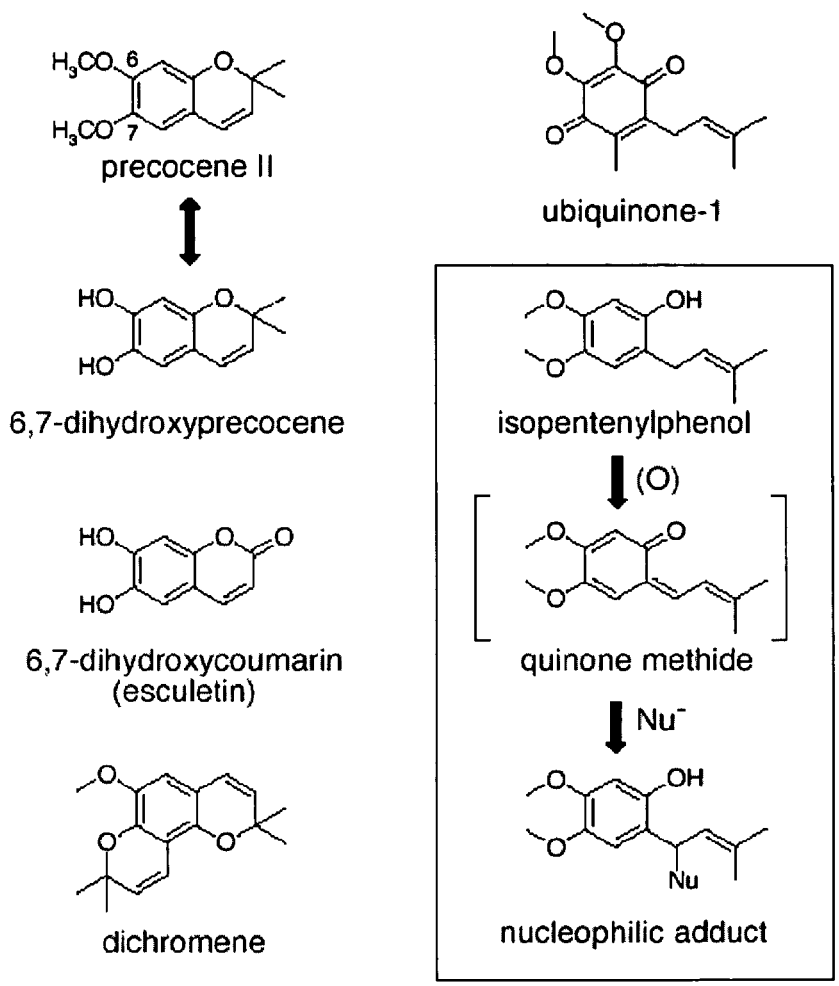
Figure 10D:
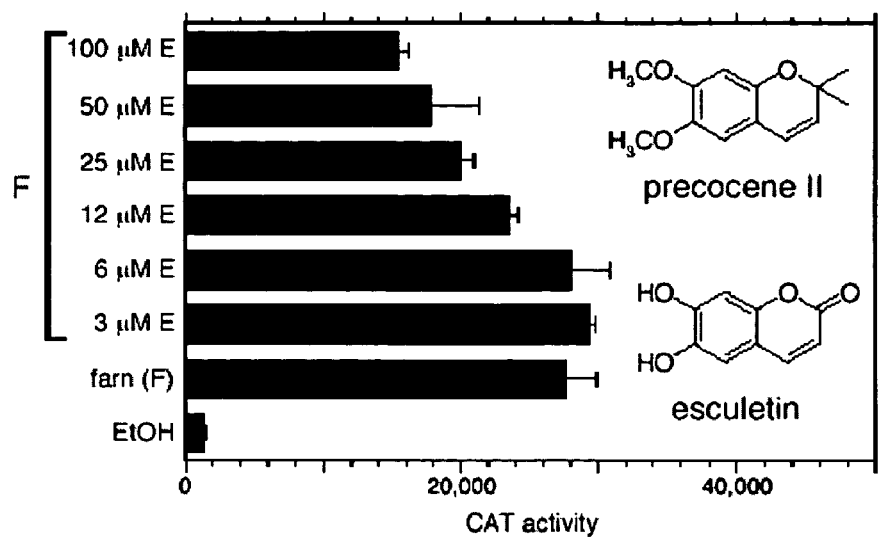
Figure 10E:
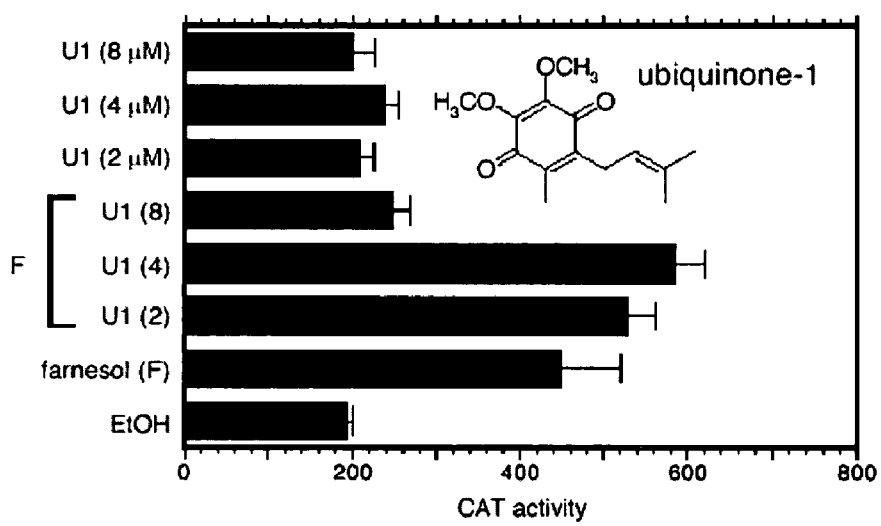
Figure 10F:
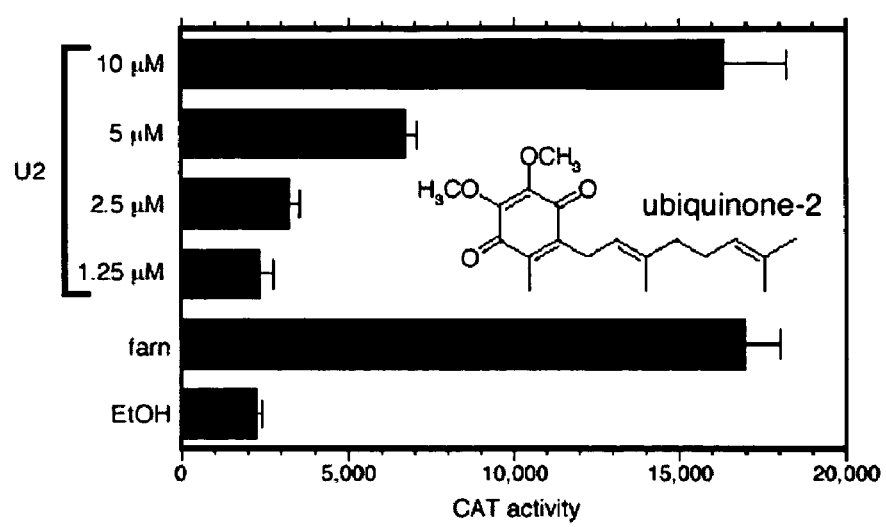

For example, instead of acting as an antagonist, precocene I, a polar dimer of precocene (Rf=0.27; m/z=380)(FIG. 10A), and its 6,7-dimethoxy congener precocene II (both from Sigma-Aldrich), and a polar dimer of precocene (FIG. 10A), may induce FXR-dependent activity, but with reduced potencies ($EC_{50}$=150 μM) compared to farnesol. Precocene I can be inactive in RAR, RXR, PPAR, or GR-based transcriptional assays, which suggests that it may be relatively specific for FXR (data not shown). Also, FXR may be activated by other precocene-like JH antagonists (FIG. 10C) including 3,4-dimethoxy-6-isopentenylphenol (3-fold induction at 100 μM) and a tricyclic dichromene (29-fold induction at 25 μM), di-, tri-, and tetraprenylated ubiquinones (U2, U3, and U4) (FIG. 10F).

In contrast, FXR may be inhibited by precocene metabolites and derivatives, such as 6,7-dihydroxy precocene and 6,7-dihydroxy coumarin (esculetin), and ubiquinone-1 (10B, 10C, and 10D).

Thus, in one embodiment, transcriptional activity programmed by muristerone-primed ecdysone receptors may be potentiated by juvenile hormones, compounds derived from food sources, and insecticides (FIG. 11). The transcriptional effects may, in some embodiments, require ligand binding domain sequences of the EcR or FXR (FIG. 12). In an embodiment, mutations in the LBD of FXR or EcR may be utilized to prepare constructs specific to various types of potential insecticide compounds.

Figure 13:
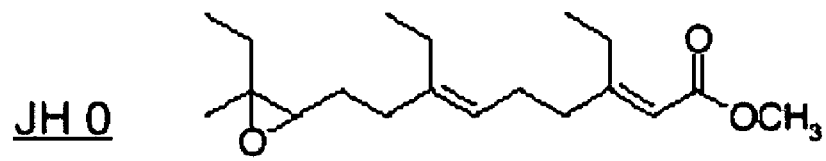
FIG. 13 shows the molecular structures of juvenile hormones isolated from insects, where the chemical formulas for the "naturally-occurring" juvenile hormones JH 0, JH I, JH II, and JH III are compared with the synthetic juvenoid ZR354, in accordance with an example embodiment of the present invention.
Figure 13:
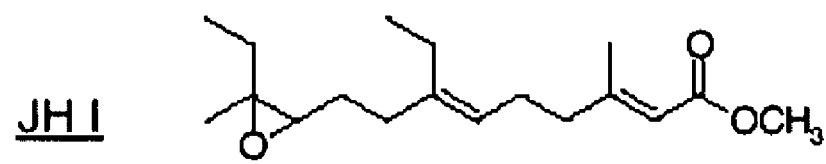
Figure 13:
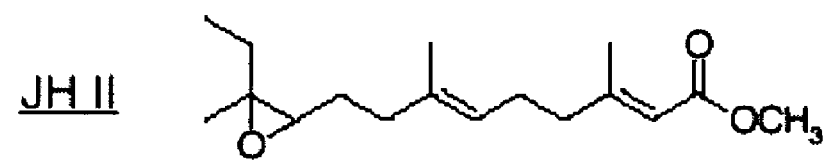
Figure 13:
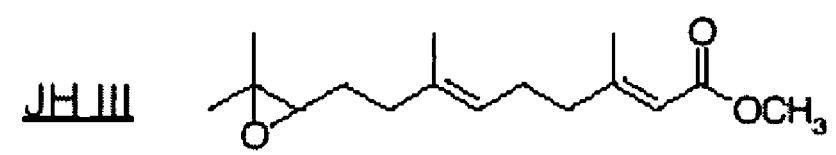
Figure 13:

Also, natural JH's may increase FXR-mediated transcription, and/or increase or potentiate EcR-mediated transcription. For example, FXR may respond to the JH I analog ZR354 in which the ethyl groups of JH I ethyl are replaced by similarly bulky dimethyl groups. In one embodiment, the natural JH's that increase FXR-mediated transcription, and/or increase or potentiate EcR-mediated transcription, comprise all "natural" JHs, e.g., JH 0, JH1, and JH II (where ethyl groups are substituted for JH III methyl groups) (FIG. 13).

D. Compositions for Use as Insecticides

Compounds of the present invention may be used in the form of compositions and can be applied to the crop and/or plant to be treated, simultaneously with, or in succession with, other compounds such as fertilizers, micronutrient donors or other preparations which influence the growth of plants. The compounds can also be selectively combined with herbicides, as well as, other insecticides, fungicides, bactericides, nematocides, molluscicides or mixtures of several of these preparations and, if desired together with further carriers, surfactants or application promoting adjuvants employed in the art of formulation, and as described in U.S. Pat. Nos. 6,737,383, 6,630,465, 6,586,470, 6,603,044, 6,617,341, 5,942,542, and 5,849,320.

For example, when applying the compound of the present invention, the compound may be applied in a form as it is without adding other active components. When the compound of the present invention is applied for plant protection purpose, the compound can be prepared into general types of formulations for plant protection use, such as wettable powder, granules, dust, emulsifiable concentrate, water soluble powder, suspension concentrate, flowable liquid, and the like.

The inert carrier used in this invention may be either solid or liquid. Where the compound of the present invention is prepared into a solid formulation, appropriate additives and carriers may be incorporated with the compound. The solid carrier may be a solid such as soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

Where the compound of the present invention is prepared into a liquid formulation, an appropriate solvent may be used for dissolving or dispersing the compound in the liquid type formulation. The liquid carrier is that which itself has solubility or which is without such solubility but is capable of dispersing an active ingredient with the aid of an adjuvant. The following are typical examples of the liquid carrier and can be used alone or as a mixture thereof: water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide. In one embodiment, the composition of the invention may also applied to the plant foliage or plant stem or insect habitat as a dilute spray prepared from any of the above-said formulations.

Also, to provide uniformity and stability to the compound in the prepared compositions, it is possible to add surface active agents into each formulation upon necessity. To emulsify, disperse, dissolve and/or wet an active ingredient, a surfactant is used. There is no limitation for the surface active agent, and examples of the surface active agent that can be added to the above-mentioned formulations include nonionic surface active agents, such as polyoxyethylene-added alkyl ether, polyoxyethylene-added higher fatty acid ester, polyoxyethylene-added sorbitan higher fatty acid ester and polyoxyethylene-added tristyryl phenyl ether, a sulfate ester of polyoxyethylene-added alkyl phenyl ether, an alkyl benzene sulfonate, a polycarbonate, a lignin sulfonate, a formaldehyde condensate of alkyl naphthalene sulfonate, and a copolymer of isobutylene and maleic anhydride.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates. Also, to improve the flowabililty of a solid product, there may be used adjuvants such as waxes, stearates and alkyl phosphates. Adjuvants such as naphthalenesulfonic acid condensation products and polycondensates of phosphates may be used as a peptizer for dispersible products. Adjuvants such as silicon oils may also be used as a defoaming agent. For example, adjuvants such as those described in U.S. Pat. No. 5,942,542 may be used.

While the compound of the present invention may be used alone, it can be combined for the use with one or more of various types of other plant protection chemicals, for example, fungicides, insecticides, acaricides and synergists. Also, in one embodiment, the composition may comprise a seed coating, formulated as described in U.S. Pat. No. 5,849,320.

The insecticide compounds of the present invention may be used in admixture with other agricultural and horticultural disease or pest controllers, acaricides, nematicides, bioagrochemicals, etc.; and herbicides, plant growth regulators, manures, etc. depending upon scenes using the present agricultural and horticultural insecticides, in order to expand both spectrum of controllable diseases and insect pest species and the period of time when effective applications are possible or to reduce the dosage.

The insecticide compounds of the present invention may be applied using a variety of protocols. Thus, the composition may be applied to a crop on which the insect pests are expected to appear, or to a site where the appearance of the insect pests is undesirable. The insecticide compositions of the present invention may also be applied to the plant seeds or the cultivation mediums for seeding such as soil to be seeded, the mat for raising seedlings, water, and the like, by the method of application to a nursery box, seed powdering, etc. or by the method of seed disinfection. For controlling the pest insects generated on fruit trees, cereals, upland field for vegetables, etc., it is also possible to make a plant absorb the compounds of the present invention by a seed treatment such as powder coating, dipping, etc., irrigation into seedling-raising carrier such as seedling-raising vessel, or planting hole, or by treatment of the culture solution for water culture.

The applied dosage of the insecticide compounds of the present invention may be varied depending upon various factors such as the insect pests to be controlled, the growth state of a plant, weather, environmental conditions, the preparation form, application method, application site and application time. In one example embodiment, the does may comprise a range of 0.1 g to 10 kg (in terms of the active ingredient) per 10 acres depending upon purposes. Thus, the amount of an active ingredient in each of the composition may be in a range of from 0.01 to 90% by weight, or preferably from 0.05 to 85% by weight based on the total weight of the formulation. In dusts, granules, or emulsifiable concentrates, the suitable content thereof is from 0.01 to 50% by weight. Each of the prepared formulations, such as wettable powder, emulsifiable concentrate, suspension concentrate and flowable solution, may be diluted with water or other solvent to be prepared and adjusted into the suspension or emulsion with a desired concentration to be applied to crop plants. For the formulations, such as granular and dust formulations, the formulation itself is directly applied to the target crop plants or soil.

The compositions of the present invention comprise compounds that increase FXR-mediated transcription and/or increase or potentiate EcR-mediated transcription present as non-toxic doses. JH levels in the insect support the use of FXR and EcR-activating compounds as insecticides. Thus, in alternate embodiments of the present invention, the compounds may comprise a dosage ranging from 0.01 µM to about 10 mM, or from about 0.1 µM to about 1 mM, or from about 0.5 µM to about 50 µM.

For example, JH III circulates in honeybee hemolymph at 0.5 µM (Elekonich, M. M. et al., 2001, *J. Insect Physiol.*, 47:1119-1125), which matches the concentration of the JH III precursor farnesyl diphosphate found in the rat liver (Bruenger, E. and H. C. Rilling, 1988, *Anal. Biochem.*, 173: 321-327). Also, JH III titers in *Diploptera* hemolymph are 6 mM during the middle of the gonotrophic cycle and 10-fold lower at other times (To be, S. S., et al., 1985, *Experientia*, 41:1028-1034). Purification of 1.6 mg of JH I ($M_r$=294) from 875 *Cecropia* abdomens (380 g) translates to 1.5 µM in the whole insect (Roller, H. and K. H. Dahm, 1968, *Recent Prog. Horm. Res.*, 1968, 24:651-80). These amounts are near the doses of JH III or farnesol (2 µM) that elicit FXR-dependent activity in the CHO assay of the present invention.

EXAMPLES

Example 1

Materials and Methods

A. Cell Growth Conditions

Chinese hamster ovary (CHO K1) cells were grown in Dulbecco's modified Eagle medium: nutrient mixture F-12 (1:1) containing 5% fetal bovine serum and supplemented with 50 u/ml penicillin, and 50 µg/ml streptomycin (Life Technologies) in a water-jacketed incubator held at 37° C. and maintained with a 5% $CO_2$ atmosphere.

B. Chemicals

Chemicals were purchased from Sigma-Aldrich Chemical Company (St. Louis, Mo.) unless noted. Plant oils were manufactured by Aura Cacia (Weaverville, Calif.). Juvocimene was synthesized as described (Mestres, R. and E. Munoz, 1996, *Synthetic Comm.*, 26:1309-1319). Myristicin, apiole, bergamotin, tangeretin, bisabolol, and cucurbitacin were obtained from Indofine Chemical Company (Somerville, N.J.). Methyleugenol was provided by the Batelle Chemical Company (Columbus, Ohio). Man-made insecticides were purchased from Chem Service (West Chester, Pa.). The precocene-like suicide substrate 3,4-dimethoxyisopentenylphenol was prepared as described Bowers, W. S., et al., 1976, *Science*, 217:647-648) except that a 3,4-dimethoxylated reactant was used.

C. Transfection Assay

The transcriptional assay utilized for the study of EcR potentiation by JH (FIGS. 2-5) was modified from the assay described by Forman et al., (Forman, B. M., et al., 1995, *Cell* 81, 687-695) as described below. Cells were seeded in 6-well polypropylene culture plates (Falcon) with $10^5$ cells per well on the day prior to transfection. Transfection was subsequently performed using either calcium phosphate (Kitareewan, S., et al., 1996, *Mol. Biol. Cell*, 7:1153-1196) or a GenePorter reagent (Gene Therapy Systems, Inc; San Diego, Calif.) following manufacturer's protocols. Each well received 1.25 µg of $(EcRE)_5$-ΔMTV-CAT (five copies of the hsp27 EcRE inserted into an mouse mammary tumor virus (MTV) promoter upstream of the chloramphenicol acetyltransferase (CAT) gene) or $(EcRE)_5$-ΔMTV-LUC (the same promoter attached to firefly luciferase), 1.25 µg of pCH 111 (SV40 early promoter linked to the β-galactosidase gene) to normalize CAT activity, and 0.25 µg of each expression plasmid (EcR, FXR, RXR, USP) that was tested. The cells were incubated with plasmid DNA for seven hours and then washed with 1×PBS. Muristerone A (murA; Alexis Biochemicals) or 20-hydroxyecdysone (20E; Sigma) dissolved in ethanol to a concentration of 10 mM was diluted as necessary to the final assay concentration (FAC) in 2 ml of fresh incubation medium that was then applied to the cells. Similarly, JHIII (Sigma) was dissolved in dimethyl sulfoxide (DMSO) to a concentration of 80 µM and diluted into the incubation medium to its final assay concentration (20, 40, 80, 160 µM). For experiments to test the effects of chenodeoxycholate (CDCA, Sigma) on FXR and EcR, CDCA was dissolved in DMSO at 20 mM and diluted in the culture medium to a final concentration of 20 µM. A corresponding volume of ethanol and DMSO were added to control cells for all experiments. For all experiments, the cells were allowed to incubate with the medium for 24 hours before collection and cell lysates were prepared by described methods (Kitareewan et al., 1996). Both β-galactosidase and CAT reporter activity were measured based on previously used methods (Kitareewan et al, 1996). Luciferase assays using luciferrin followed the specifications of the manufacturer.

Transcriptional activity, measured as $^{14}C$-chloramphenicol counts (for measuring CAT activity) or relative luciferase activity (RLU) was quantified for each cell lysate. The counts were then normalized by adjusting for differences in β-galactosidase activity, since β-galactosidase expression is controlled by a constitutive promoter and provides an estimate of cell mass. Data were normalized as fold-induction based on differences in reporter gene activity between hormonally treated and control cells For the analysis of the ability of various compounds to activate FXR (FIGS. 6-13), the same assay was used with the rat FXR and mouse RXRα. DNAs were added to cells for 7 hours and subsequently washed with PBS. Activators were then added in fresh DMEM-F12 media containing 5% charcoal-adsorbed FBS and incubated at 37° C. for 22 hours. CAT and β-galactosidase activities were measured from cell lysates prepared by three cycles of freeze-thawing as described (Kitareewan, S. et al., 1996, *Mol. Biol. Cell*, 7:1153-66).

D. Chromatographic Analysis of Compounds

Thin layer chromatography to analyze the chemical structure of the farnesoids and other compounds tested for their ability to activate FXR and/or activate or potentiate EcR was carried out using Whatman LK6D silica gel plates (60 Å, 250 µm). The mobile phase was 90% hexane/10% ethyl acetate. For the separation of precocene I, 10 milligrams of material was applied to a 20 cm ×20 cm plate. Ultraviolet light-absorbing material in three zones was scraped from the plate, eluted with chloroform:methanol (1:1), dried, and resuspended in methanol. A portion of the material was derivatized with trimethyl silyl chloride and subjected to gas chromatography-mass spectrometry as described (Kitareewan, S. et al., 1996, *Mol. Biol. Cell*, 7:1153-66). Samples were assayed for FXR-dependent transcriptional activity as outlined above.

Example 2

Description of Plasmid Vectors

Expression plasmids encoding *Drosophila* EcR (CMX-EcR), *Drosophila* USP (CMX-USP), rat FXR (CMX-FXR), human RXRα (CMX-hRXRα), glucocorticoid receptor (CMX-GR), and a glucocorticoid receptor trans-activating domain fused to an ecdysone DBD and LBD (CMX-GEcR) have been described (Yao et al., 1992, *Cell*, 71: 63-72; Yao et al., 1993, *Nature* 366:476-478; and Forman, B. M., 1995, *Cell*, 81: 687-693). The expression plasmids are constructed by inserting restriction fragments contining the appropriate coding sequence for the gene to be expressed into the CMXPL1 plasmid. For HRXRα, an EcoRI fragment of human RXR-α (hRXRα) was subcloned into the CMXPL1 plasmid.

The FXR expression vector (pRS-rFXR) contains DNA sequences encoding a constitutively active promoter derived from the Rous sarcoma virus long terminal repeat (LTR) fused to the complementary DNA sequence encoding the rat farnesoid-X-activated receptor (Forman et al., *Cell* 1995; NCBI Accession No. U18374) which is followed by a DNA sequence specifying the SV40 polyadenylation signal. Briefly, the expression plasmid pRS-rFXR was derived from pRS-hGR as follows: pRS-hGR was digested with Kpn I and Bam HI restriction endonucleases to release DNA sequences specifying the human glucocorticoid receptor (GR) and cDNA encoding rat FXR and its 5' and 3' untranslated sequences was then inserted into Kpn I and Bam HI digested pRS-hGR.

GGF, comprising the glucocorticoid (G) amino terminus and DBD linked to the LBD of FXR, was prepared following a strategy similar to that used to construct GGEc (KS Christopherson, et al., 1992, *Proc Natl Acad Sci USA*, 89:6314-6318), where the GR amino terminus and DBD (appending 23 amino acids downstream from the conserved gly-met) were fused to the FXR LBD. To construct GGF, the plasmid pRShGR$_{nx}$ (Giguere, V. et al., 1987, *Nature*, 330:624-9), with Not I and Xho I sites flanking the GR DBD, was first used as a template in a polymerase chain reaction (PCR) assembled with the forward primer 5'-GGAATGATTGCATC ATCGATAAAATTCG-3' (Cla I restriction site underlined) (SEQ ID NO: 1) and the reverse primer 5'-GAGGT CTCGAGTGAGACTCCTGTA-3' (Xho I site underlined) (SEQ ID NO: 2). Cla I- and Xho I-digested pRShGR$_{nx}$ was then ligated to the 132 bp PCR product. The resulting plasmid was digested with Xho I and Bam HI and the GR-containing DNA fragment was isolated and ligated to an Xho I-Bam HI LBD fragment from an FXR variant prepared by hybridizing the oligonucleotide 5'-CTCGAGTGTATGTATACAG-GTTTGTTAACTGAA-3' (SEQ ID NO: 3) to another oligonucleotide 5'-AACAAACCTGTATACATACACTCGA-3' (SEQ ID NO: 4) which was then ligated to a Hpa I-digested fragment from the pRSV-FXR expression vector. The DBD/LBD junction in GGF is 5'-GMNLEARKTKKKIKGIQQATTGVSQECMYTGL LTEIQCKS-3' (SEQ ID NO: 5) where the GR residues are underlined, amino acids GM are the last two residues of DNA binding domain and amino acids from FXR are in bold (not underlined).

The GGEc vector (Christopherson et al., 1992, *Proc. Natl. Acad. Sci., USA*, 89:6314) is derived from the rat GR expression vector pRSV.GGG (Miesfeld et al., 1986, *Cell*, 46:389) and contains the Rous sarcoma virus LTR fused to DNA encoding the rat glucocorticoid receptor (GR) amino terminus and DNA binding domain fused to a DNA sequence encoding the *Drosophila melanogaster* ecdysteroid receptor (EcR) (NCBI Assession No. M74078; Koelle, M. R., et al., 1991, *Cell* 67:59-77) ligand binding domain (LBD). In GGEc, rat GR LBD amino acids 528 to 795 were replaced by EcR LBD amino acids (EcR amino acids 329 to 878).

The GEcEc (i.e., GRdEcR) vector has been described previously (Yao, T. P, et al., 1993, *Nature* 366: 476-479; No, D.,
et al., 1996, *Proc. Natl. Acad. Sci USA*, 93:3346-3351). Briefly, GEcEc was constructed by ligation of a Not I-Bam HI fragment containing the DBD and LBD of a modified EcR cDNA, EcR$_{nx}$, in place of the DBD and LBD of the similarly modified GR expression vector construct pRShGR$_{nx}$ (Giguere et al., 1987, *Nature* 330: 624). The modified EcR cDNA was constructed using site-directed mutagenesis (Kunkel, 1985, Proc. Natl. Acad. Sci., USA, 82:488) to insert Not I (oligonucleotide template: 5'-CCTGCGCCACGGCG-GCCGCCGGAGCTGTGCCTG-3') (SEQ ID NO: 6) and Xho I (oligonucleotide template: 5'-GTGGGTATGCGC-CTCGAGTGCGTCGTCCC-3') (SEQ ID NO: 7) sites immediately flanking the DBD. This results in conversion of amino acids 259-261 from ValGlnGlu to ArgProPro and amino acid 331 from Pro to Leu.

Reporter plasmids EcR$_5$-ΔMTV-LUC, and MMTV-LUC have also been described (Yao et al., 1992, *Cell*, 71: 63-72; Yao et al., 1993, *Nature* 366:476-478; and Forman, B. M., 1995, *Cell*, 81: 687-693). The reporter plasmids may be constructed by inserting a ecdysone reponse element (e.g., 5'-GATCCGACAAGGGTTCAATGCACTTGTCA-3'; SEQ ID NO: 8) at position-77 of a mouse mammary tumor virus (MMTV or MTV) promoter-reporter gene construct, such as MTV-CAT, MTV-LUC, MTV-GFP (Christopherson, K. S., 1992, *Proc. Natl. Acad. Sci., USA*, 89: 6314-6318). The (EcRE)$_5$-ΔMTV-LUC construct was produced by subcloning the promoter region of MTV into the multiple cloning site of the p-LUC plasmid (Promega); this vector resembles the (EcRE)$_5$ ΔMTV-LUC described previously (No et al, *Proc. Natl. Acad. Sci, USA*, 93:3346-3351).

Construction of the three *Drosophila* EcR isoform vectors (EcRA, EcRB1, EcRB2) has been described (Mouillet, J-F, et al., 2001, *Eur. J. Biochem.* 268:1811-1819). To generate the vectors EcR-A, B1, and B2 sequences (Koelle et al., 1991, *Cell:* 67, 59-77; Talbot et al., 1993, *Cell:* 73:1323-1337; NCBI Accession Nos. S63761 and S63762) generated by PCR were cloned into the BamHI and XbaI sites of the pcDNA3 vector (InVitrogen). The EcRA DNA fragment was produced by using PCR amplification of EcRA DNA with the pWT57 vector as a template (Talbot et al, 1993). The forward primer, DEAf (5'-CACCCGGATCCACCATGTTGACGAC-GAGTGGACAA) (SEQ ID NO: 9) was used with the reverse primer, DEr (5'-ACCTCTCTAGACTATGCAGTCGTC-GAGTGGTC) (SEQ ID NO: 10) to produce a fragment that was subsequently digested with BamHI and XbaI and ligated into a pcDNA3 vector digested with BamHI and XbaI. The plasmid encodes a version of EcRA that includes 849 amino acids, and deletes the F domain. The EcRB1 DNA fragment was produced by using PCR amplification with the pMK1 vector (Koelle et al, 1991; Talbot et al, 1993) using the aforementioned DEr primer with the forward primer, DEB1f (5'-CACCCGGATCCACCATGAAGCGGCGCTG-
GTCGAAC) (SEQ ID NO: 11). The fragment was subsequently digested and cloned into the pcDNA3 vector as described for A. The plasmid encodes a version of EcRB1 that includes 878 amino acids, and deletes the F domain. The EcRB2 DNA fragment was produced by using PCR amplification with the pWT56 vector (Talbot et al, 1993) using the aforementioned DEr primer with the forward primer, DEB2f (5'-CACCCGGATCCACCATGGATACTTGTG-
GATTAGTA-3') (SEQ ID NO: 12). The fragment was subsequently digested and cloned into the pcDNA3 vector as described for A. The plasmid encodes a version of EcRB2 that includes 669 amino acids, and deletes the F domain.

The VP16dEcR vector has also been described previously (Yao, T. P, et al., 1993, *Nature* 366: 476-479; No, D., et al., 1996, *Proc. Natl. Acad. Sci USA*, 93:3346-3351; Mouillet et al., 2001; Henrich et al., 2003). The VP16 EcR vector was constructed using PCR amplification with pWT57 with the reverse primer, Der (described above), together with the forward primer Def (5'-CACCCGGATCCACCATGAA-GAAGGGACCTGCGCCA-3') (SEQ ID NO: 13). The fragment was subsequently digested with BamHI and XbaI and cloned in to the multiple cloning site of pVP16 (Clontech). The resulting vector encodes a protein consisting of the VP16 activation domain linked to the C-E domain of EcR and consisting of 626 amino acids.

The VP16CfUSP vector is also previously described (Palli, SR, et al., 2003, *Eur J. Biochem,* 270:1308-15). The USP vector contains the USP LBD of *Choristoneura fumeriferana* (NCBI Accession No. AF045891). Both VP16 chimeras contain an N-terminal domain that is active in mammalian cells (Louvion et al, 1993, *Gene:* 131:120-134). To generate VP16CfRSP, PCR amplification with a forward primer including an EcoRI site and a reverse primer including a BamHI site was used to produce a fragment that encodes the D-F domains of *Choristoneura fumiferana* USP (Accession #AAC31795). The resulting PCR product was digested with EcoRI and BamHI and cloned into the pVP16 vector (Clontech) to produce the fusion protein.

Other VP16-USP fusion vectors VP16-dUSPF1, F2, and F3, have been generated. These vectors were constructed using the pZ7-1 vector (Henrich et al, *Nucl. Acids Res,* 18:4143-4148, 1990) encoding *Drosophila melanogaster* USP. F1 was constructed with the forward primer 5'-TTTTGAATTCAGCGGCAGCAAGCACCTCTGC-3' (SEQ ID NO: 14) together with the reverse primer, 5'-TTT-TAAGCTTTAGAGTCGGGACCCTACTCC-3' (SEQ ID NO: 15). The resulting PCR product was digested with EcoRI and HindIII and cloned into pVP16 (Clontech) digested with EcoR1 and HindIII. The resulting protein encodes a VP16 activation domain fused to the last six amino acids of the A/B domain and the C-E domains of USP. F2 was constructed using the same pZ7-1 vector, reverse primer and the forward primer (5'-TTTTGAATTCTGCTCTATTTGCGGG-GATCGG-3') (SEQ ID NO: 16). The resulting PCR product was cloned into VP16 using the same approach described for F1. The resulting protein encodes a VP16 activation domain fused to the C-E domain of *Drosophila melanogaster* USP. F3 was constructed as both F1 and F2 except that the forward primer used was (5'-TTTTGAATTCAAGCGCGAAGCG-GTCCAGGAG'3') (SEQ ID NO: 17). The resulting protein encodes a VP16 activation domain fused to the D-E domain of *Drosophila melanogaster* USP.

Example 3

JHIII Potentiates Ecdysteroid-induced Transcriptional Activity in a Mammalian Cell Line Transfected With EcR In an initial series of studies, a GRdEcR chimera that consists of the rat glucocorticoid receptor (GR) activation domain attached to the EcR DBD and LBD (FIG. 1) was cotransfected along with mRXRα into CHO cells. The response of transfected cells to murA was measured using a (EcRE)$_5$-ΔMTV-CAT reporter plasmid that carries five tandem repeats of the hsp27 EcRE linked to the MTV (mouse mammary tumor virus) promoter and the chloramphenicol acetyltransferase gene (CAT).

Results of a typical experiment are shown in FIG. 2. Cotransfection with GrdEcR and RXR evoked a detectable response at dosages as low as 0.1 μM murA. It was found that juvenile hormone III (JHIII) potentiated the response of murA in a dose-dependent manner (using 20, 40, 80, and 160 μM JHIII) at submaximal murA dosages (0.1 μM and 1 μM murA) (FIG. 2, sets 2 and 3, respectively). JHIII did not display the ability to evoke a response that was greater than the maximal level induced by 10 μM murA. Despite the structural resemblance between the LBDs of EcR and the vertebrate FXR, which is highly responsive to JHIII alone (Forman et al., 1995), JHIII alone did not show an effect on transcription mediated by the GEcEc chimera (FIG. 2, set 1). Thus, this experiment shows that although JH by itself may not be able to evoke a EcR mediated response, JH can potentiate the effect of EcR ligands.

Example 4

Ecdysteroid Responsiveness and JHIII Potentiation in EcR Chimeras Depends Upon Activating Ligand and Heterodimeric Partner The potentiation experiments were repeated with a chimera encoding the VP16 activation domain connected to the DBD and LBD of *Drosophila* EcR to generate the construct VP16dEcR (FIG. 3). Luciferase was used as a reporter gene, (EcRE)$_5$-ΔMTV-LUC. All activities are normalized fold-inductions in relative light units from cells incubated with hormone for 20 hours compared to luciferase activity levels in cells incubated with solvents only. For all combinations, 80 μM JHIII was used. The dosage of muristerone A (murA) used was based upon preliminary experiments to determine a submaximal dosage wherein a JHIII effect, if any, was detectable. All data are based on the mean normalized fold-inductions from at least three replicates. The range (coefficient of variation) of fold-inductions was less than 15% among replicates.

VP16dEcR tested with muristerone A generated a sensitive and robust ecdysteroid response (based on normalized fold-induction). The VP16dEcR, partnered with mouse RXR (mRXR), showed a response to 0.01 μM and 0.1 μM muristerone A that was further potentiated by JHIII (FIGS. 3a and 3b, respectively). The VP16dEcR chimera also displayed a discernible response to 20E at 10 μM (over 20-fold) using RXR. The VP16dEcR/20E activity was only minimally affected by the additional presence of JHIII, however (not shown).

The VP16dEcR was also tested with VP16CfUSP as the heterologous binding partner. FIG. 3c shows results at 0.1 μM murA. The same degree of potentiation was observed using the VP16dEcR/USP combination as with the VP16dEcR/RXR when using murA, except that a higher murA dose was required to achieve the same efficacy. The normalized level of JHIII-mediated potentiation of the murA response with USP was similar to that seen for RXR. However, the combination of VP16dEcR with VP16CfUSP combination showed no response to 10 μM 20E and was not affected by the additional presence of JHIII (data not shown).

Example 5

*Drosophila* EcR Isoforms Display Different Capabilities in Mammalian Cells that Depend Upon Ligand and Heterodimeric Partner In order to evaluate the activity of the various EcR isoforms, each of the three natural *Drosophila melanogaster* EcR isoforms, (EcRA, EcRB1, and EcRB2) were cotransfected into CHO cells with the VP16CfUSP fusion protein.

Results are shown in FIG. 3, sets d-f. Again, for all combinations, 80 µM JHIII was used, and the dosage of muristerone A (murA) used was based upon preliminary experiments to determine a submaximal dosage wherein a JHIII effect, if any, was detectable. For the results shown in FIG. 3, all data are based on the mean normalized fold-inductions from at least three replicates, except for EcRA (two replicates). All activities are normalized fold-inductions from cells incubated with hormone for 20 hours compared to luciferase activity levels in cells incubated with solvents only. Each fold induction represents an average based on three or four replicates, and range was less than 15% mean fold-inductions for each data point. All combinations were also tested with JHIII alone (80 µM), which registered no significant effect on normalized RLU activity.

The different EcR isoforms are known to differ at the N-terminal region of the protein, which is the part of the protein involved in dimerization of EcR with either USP, RXR or other appropriate partners. All three isoforms showed some transcriptional capability in the mammalian cell culture system. Interestingly, however, none of the isoform constructs showed the same dosage sensitivity seen with VP16dEcR/RXR (direct comparison not shown).

For example, when tested in the absence of hormone, the EcRB1/VP16CfRSP combination showed a relatively high level of ligand-independent transcription. Thus, the EcRB1/VP16CfUSP had between 10 and 20-fold higher basal levels than any other EcR construct tested. The EcRA isoform in combination with VP16CfUSP also showed a level of basal level of transcription that was 2 to 3 fold higher than that observed for EcR-B2. In contrast, the basal activity of the B2/VP16CfUSP dimer was about the same as the basal activities produced by the VP16dEcR/RXR and GEcEc/RXR (i.e., GRdEcR/RXR).

FIG. 4 shows the effects of murA, 20E, and JHIII on RLU activity induced by $(EcRE)_5 \Delta MTV$-LUC in CHO cells cotransfected with a *Drosophila* EcR isoform and VP16CfUSP where sets 1, 2, and 3 in the figure correspond to EcRA, EcRB1 and EcRB2, respectively. When tested with VP16CfRSP, all three *Drosophila* isoforms were induced by about 30-40 fold at 1 µM murA. The response of all EcR isoforms in the presence of VP16CfUSP was potentiated by the presence of 80 µM JHIII in the presence of 0.1 µM murA (FIG. 4). It was found that the effect was dose-dependent (data not shown) similar to the results seen with GEcEc (i.e, GRdEcR). The range of the normalized fold inductions for each experiment was found to vary by less than 15% for each experiment.

The *Drosophila* EcR isoforms and VP16CfUSP were also tested with 20E (FIG. 4). At a dosage of 10 µM 20E, all three constructs generated a consistent and discernible transcriptional response. Only the EcRB2/VP16CfUSP dimer (FIG. 4, set 3) was potentiated significantly by the additional presence of JHIII, however. That only the B2 EcR isoform is potentiated by JHIII in the presence of 20E indicates that JHIII potentiation may depend upon both the N-terminal domain of EcR and the activating ecdysteroid.

The activity observed among the three EcR isoforms was dependent upon the identity of the heterologous partner used. For example, in contrast to the robust response observed when RXR was tested with VP16dEcR, RXR did not mediate a response to murA as a dimer with either EcRA or EcB2. Only EcRB1/RXR displayed a response to murA among the three isoforms (FIG. 3d, e, and f), but the levels of transcription were relatively low and dramatically reduced from those noted for the B1/USP combination. The murA response was further potentiated by JHIII with the B1/RXR combination, though JHIII by itself failed to evoke any response. Unlike the 20E response noted for all the isoforms with USP as a partner, none of the isoforms showed a 20E response with RXR as a heterodimeric partner. Absolute transcription levels were also relatively low with RXR.

The results indicate that ligand-independent and ligand-dependent transcription as well as JHIII potentiation may depend upon an interplay of the EcR N-terminal domain, the activating ecdysteroid, and the heterodimeric partner. Thus, it was found that responsiveness of the natural EcR isoforms to 20E requires USP (rather than RXR) as a dimeric partner. Also, among the three isoforms (EcRA, EcRB1, and EcRB2), JHIII potentiation in the presence of 20E occurred only with the EcRB2 isoform and USP. Specific combinations of the EcR N-terminal domain and the heterodimeric partner (e.g. VP16 and RXR, B2 and USP) result in a functional receptor that is capable of showing an ecdysteroid response and/or JHIII potentiation. Levels of ligand-independent transcription also depend upon both the EcR N-terminal domain and the heterodimeric partner. The potentiation observed in the experiments cannot be attributed to the activation of RXR by either JHIII or a JHIII metabolite, since JHIII showed no activity by itself on the assays (Harmon, M. A., et al., 1995, *Proc. Natl. Acad. Sci. USA,* 92:6157-6160; Saez, E., et al., 2000, *Proc. Natl. Acad. Sci. USA,* 97:14512-14517).

Example 6

Assay of FXR Interaction with USP

It is known that the FXR/RXR heterodimer may respond to JHIII. Thus, a series of experiments were carried out to determine the ability of insect USP to mediate an ecdysteroid and/or JHIII response in conjunction with FXR.

The combination of FXR and USP evoked a low level response in CHO cells to JHIII (FIG. 5). The response observed is attributable to endogenous expression of low levels of RXR in these cells (data not shown). The addition of ecdysteroids (murA or 20E) with JHIII induced no elevation of FXR-mediated activity (FIG. 5). Also, USP was unable to potentiate a response to 20 µM CDCA (Chiang et al, 2000, *J. Biol. Chem.,* 275:10918-10924), the strongest activator of FXR known to date. In addition, EcR was unresponsive to CDCA alone or as a potentiator of murA response (data not shown). These experiments indicate that whereas EcR is able to interact with USP or RXR, and FXR interacts with RXR, FXR does not interact with USP to induce transcription. For FIG. 5, all activities are normalized log (fold inductions) based on RLU activity from a simultaneous run that was repeated twice and generated similar trends, though dosage levels varied.

Example 7

Evaluation of Compounds for Activity at the Farnesoid Receptor (FXR)

In these experiments, candidate juvenoids were tested for their ability to activate FXR mediated transcription by transfecting Chinese hamster ovary (CHO) cells using the FXR plasmid, mouse RXRα, and the $\Delta MTV$-$(EcRE)_5$-CAT reporter as described herein. An RXR-dependent CRBPII-CAT reporter plasmid was employed in parallel assays to discern activators specific for this receptor.

A. FXR Responds to Endogenously-Produced Farnesol Metabolites

Farnesoid-like molecules define a metabolic pathway that begins with farnesyl diphosphate (Weinberger, C., 1996, TEM, 7:1-6). Thus, in these experiments, endogenously-produced metabolites of farnesol (FIG. 6) (50 µM FAC) were assayed as FXR effectors. FIG. 6 shows the metabolic route from farnesyl diphosphate (FDP) to methyl farnesoate in mammals or juvenile hormone III in insects and the relative efficacy of each isoprenoid as an inducer of FXR-dependent transcription. A negative sign indicates no activity and positive signs correlate with the efficacy (ratio of maximal inducible activity achieved with the highest non-cytotoxic dose of activator compared to that obtained with vehicle). Transcriptional activities ranged from 2-fold increases for farnesoic acid to 20-fold inductions for juvenile hormone III when tested at 50 µM.

Thus, nerolidol induced FXR-dependent CAT activity with a potency ($EC_{50}$=15 µM) and efficacy (9-fold induction) like its farnesol isomer (FIG. 6). Alcohol and aldehyde dehydrogenases oxidize farnesol farnesal and farnesoic acid (Christophe, J. and G Popjak, 1961, *J Lipid Res.*, 2:244-257), which exhibited 2 to 3-fold activity increases in FXR mediated transcriptional activity, respectively. Insects and mammals transform farnesoic acid into methyl farnesoate (Schooley, D. A. and F C Baker, 1985, Juvenile hormone biosynthesis. In: *Comprehensive Insect Physiology, Biochemistry, and Pharmacology* Edited by G A Kerkut, L I Gilbert, vol. 7. pp. 363-389. Oxford: Pergamon Press; 1985: 363-389) which showed a 6-fold induction of FXR mediated transcription. Methyl farnesoate is epoxidized in insects to the FXR activator JH III, which induced CAT activity 15-fold. Thus, it was found that FXR responds variably to all endogenously-produced open chain sesquiterpenoid metabolites of farnesyl diphosphate in the biochemical pathway that extends from farnesol to JH III.

B. Juvenile Hormone Mimetics Induce FXR-Dependent Transcription

FXR-activating farnesoids have been described as JH agonists in insect bioassays (Schneiderman, H. A., and L I Gilbert, 1964, *Science*, 143:325-333). Like farnesol, nerolidol was effective as a juvenoid and as an FXR effector (Table 4). The chlorophyll metabolite phytol increased activity three times, thereby evincing marginal JH activity (Table 4). In contrast, neither the monoterpenes linalool (200 µM) nor geraniol were effective as FXR activators or juvenoids.

Synthetic juvenoids (Table 4 and FIG. 7A) were also evaluated. The ethyl ester of 7,11-dichloro-2-ene farnesoic acid (ZR232) (Law, J. H. et al., 1966, *Proc. Natl. Acad. Sci. USA*, 55:576-578), induced CAT activity 5-fold when added at 50 µM (FIG. 7A). In addition, the synthetic juvenoids, methoprene and pyriproxyfen, increased FXR-dependent activity with efficacies like that produced by JH III (Table 4 and FIG. 7A). These results indicate that FXR activates transcription in response to isoprenoids and chemicals previously reported to have insect JH activities.

Plant-derived JH agonists were also examined as FXR effectors. Farnesol-like echinolone (FIG. 7A), an essential oil of echinacea (Jacobson, M., et al., 1975, *Lloydia*, 38:473-476) maximally induced FXR-dependent activity 7-fold. Juvocimene (found in sweet basil) and juvabione (from balsam fir) (FIG. 7B), two JH mimetics WS (Bowers, W. S. et al., 1966, *Science*, 154:1020-1; Bowers, W. S. and R Nishida, 1980, *Science*, 209:1030-1032), increased RXR mediated transcription 10-fold and 3-fold, respectively. Synthetic juvocimene (25 µM) increased FXR-dependent activity 5-fold. Also, α-bisabolol (50 µM), an analog of juvabione found in chamomile, increased activity 13-fold (FIG. 7B).

Certain olive oil vehicles have been distinguished as juvenoids in insect molting assays (Carlisle, D. B. and P. E. Ellis, 1968, *Science*, 162:1393-1394). Extra-virgin olive oil or its redolent tyrosine-like 2-, 3,- and 4-hydroxyphenethyl alcohol constituents (400 µM) all elevated FXR-dependent activity 3-fold. Unsubstituted phenethyl alcohol was inert at this dose. Activation of FXR by natural and synthetic JHs offers further evidence that FXR has functional attributes of an insect JH receptor.

C. FXR is Activated by Insecticide Synergists

The observation that sesame oil and its sesamin and sesamolin ingredients increased the toxicity of insecticides led to the development of synergist analogs like piperonyl butoxide (PB) (FIG. 7C) and the description of these compounds as JH agonists (Bowers, W. S., 1968, Science, 161:895-7). PB and sesamin (100 µM) induced FXR-dependent activity 9-fold and 12-fold, respectively. Crude sesame oil (Sigma) maximally increased activity 3-fold; three commercial brands of toasted sesame oil were more effective, however, delivering maximal activities between 8-fold and 17-fold. Also, 4-fold induction was produced by 50 µM piperine, a PB analog from black pepper, as well as by myristicin and its p-dimethoxylated congener apiole in dill and parsley (FIG. 7C) (both at 250 µM FAC). The sesamolin cleavage product sesamol (FIG. 7C) was inactive at 400 µM FAC as were PB analogs with small side chains such as piperonyl alcohol, piperonylic acid, and safrole. These results indicate that FXR shares functional qualities similar to those expected of an insect JH receptor, and that the synergistic actions of PB and sesamin may partly reflect intrinsic JH activities.

D. FXR is a Target for Plant Secondary Metabolites

Commercially available oils from various plants were also examined as FXR effectors. For example, cedarwood oil and its redolent sesquiterpene α- and β-ionone isomers increased FXR-dependent activity with potencies and efficacies like those induced by farnesol (Table 5). It is known that sesamin blocks liver HMG CoA reductase activity, that farnesol is anti-proliferative, and that FXR is inhibited by the hypocholesterolemia-inducing plant steroid guggulsterone (Wu, J. et al., 2002, *Mol Endocrinol.*, 16:1590-7; Urizar, N. L. et al., 2002, *Science*, 296:1703-6). Given the reported biochemical activities for sesamin, farnesol, and FXR, phytochemicals previously reported to modulate plasma cholesterol levels or growth in mammals were tested as FXR effectors. The data are summarized by molecular class in Table 5.

i. Monoterpenes: Given that FXR responds to endogenously-produced isoprenoids, plant-derived monoterpenes were examined for activity. Tea tree oil, which contains insecticidal terpinen-4-ol (40% of mass), 1,8-cineole (eucalyptol), and α-terpineol, maximally elevated FXR-dependent CAT activity 8-fold (Table 5 and FIG. 8A). Each of these constituents induced activity only two-fold at 800 µM, but notably 400 µM of any pairwise mixture increased activity like tea tree oil itself (FIG. 8A). Carvacrol and thymol (300 µM) in oregano inhibit tumor cell growth (Case, G. L. et al., 1995, *Lipids*, 30:357-9; Burke, Y. D. et al., 1997, *Lipids*, 32:151-6) and both induced CAT activity 6-fold (Table 5). Limonene in orange oil blocks tumors, inhibits HMG CoA reductase, and is being tested as a human chemotherapeutic agent (Crowell, P. L. and M. N. Gould, 1994, *Crit. Rev. Oncog.*, 5:1-22; Elegbede, J. A. et al., 1984, *Carcinogenesis*, 5:661-4.; and McNamee, D., 1993, Lancet 342, 801). Limonene and limonene oxide (400 µM) were inactive in activation of FXR, but either enantiomer of its metabolite perillyl alcohol induced FXR-dependent CAT activity 4-fold (Table 5). This dose matches that required to inhibit cell growth in culture (He, L. et al., 1997, *J. Nutr.*, 127:668-674). Finally, while menthol and fenchone (fennel) were inactive (0.5 mM), 0.5 mM fenchyl alcohol induced activity 5-fold, as did 0.5 mM pine tree-derived pinane diol (Table 5).

ii. Diterpenes: Forskolin, one of the most robust FXR effectors yet described (Howard, W. C. et al., 2000, *Tox. Appl. Pharm.*, 163:195-202), increased activity more than 100-fold when added at 2 µM. Like forskolin, 1-trans-$\Delta^9$-tetrahydrocannabinol (THC) from the *cannabis* plant contains a tricyclic ring. In addition to their psychoactive effects, cannabinoids block cell growth, inhibit DNA synthesis, and lower the incidence of spontaneously-arising mouse liver tumors (Carchman, R. A., et al, 1976, *Cancer Res.*, 36:95-100; Munson, A. E. et al, 1975, *JNCI*, 55:597-602). A 5-fold increase in FXR-dependent CAT activity was elicited by 15 µM THC, but not by its $\Delta^8$-isomer or by cannabinol (Table 5). Abietic acid (100 µM), another forskolin-like diterpene in ginko, spruce, and fir, induced CAT activity 50-fold (Table 5). FXR-dependent activity was also increased 3-fold by tumor-promoting croton oil at the highest non-cytotoxic dose. Phorbol-like diterpenes from *croton tiglium* and related plants such as phorbol 12,13-dibutyrate, mezerein, and ingenol 3,20-dibenzoate, increased activity 2, 3, and 5-fold, respectively, when added at 10 µM (Table 5). Phorbol and ingenol were inactive.

The palmitate esters of cafestol and kahweol have been identified as the mediators of the hypercholesterolemic effects of coffee in humans (but not in other primates or rodents) (see e.g., Weusten-Van der Wouw, M. P. et al., 1994, *J. Lipid Res.*, 1994, 35:721-735). Cafestol, kahweol and their acetate derivatives (20 µM) induced FXR-dependent CAT activity between 10- and 20-fold (FIG. 8B and Table 5). At this dose, the major diterpenoid-fatty acyl ester in coffee oil, cafestol palmitate, was inert.

iii. Triterpenes.

Resin from *Commiphora molmol* (myrrh) exhibits insecticidal activity in *lepidoptera* (Shonouda, M. L. et al., R M Farrag, O M Salama, 2000, *J Environ Sci Health B*, 35:347-56). FXR was activated by essential oils from myrrh and frankincense with maximal inductions approaching 20 times more than vehicle (Table 5). Some of the FXR-dependent activity promoted by frankincense is derived from triterpenoid components, β-boswellic acid and oleanolic acid (25 µM), which increased activity 11- and 3-fold, respectively (Table 5). Ursolic acid is a rosemary ingredient related to oleanolic acid that inhibits mouse skin tumors (Huang, M. T. et al., 1994, *Cancer Res.*, 54:701-708; Nishino, H. et al., 1988, *Cancer Res.*, 48:5210-5215). While rosemary oil maximally induced FXR-dependent activity 12-fold (Table 5), ursolic acid (50 µM) was ineffective as were its polyketide constituent rosemarinic acid and its curcumin congener.

Cucurbitacins are phytoecdysteroids that inhibit ecdysone receptor (EcR) function (Dinan, L. et al., 1997, *Biochem J*, 327:643-50). Cucurbitacin D (1 µM) suppressed FXR-dependent activity promoted by JH III and CDCA (40 µM each), 7- and 58-fold, respectively (FIG. 8C). The $\Delta^1$-unsaturated congener cucurbitacin I also inhibited farnesol-induced activity with an IC$_{50}$~50 nM (data not shown). The 22-oxo-$\Delta^{23}$-ene group of cucurbitacin is critical for EcR antagonist activity, allegedly by forming covalent adducts between its α,β-unsaturated carbonyl group and amino acids in the EcR ligand binding domain (Dinan, L. et al., 1997, *Biochem J*, 327:643-50). 22R-Hydroxycholesterol is metabolized in mammals to pregnenolone via a 20,22-dihydroxycholesterol intermediate with an apparent $K_m$ of 7 µM (Sugano, S., et al., 1966, *J Biochem* (Tokyo) 1996, 120:780-7). Coincidentally, FXR-dependent transcription was induced 10-fold by 20α- or 22R-hydroxycholesterol (7.5 µM), but not by 22S-hydroxy-, 7-keto-, or 7α-hydroxycholesterols (data not shown). It is possible that the 20,22-dihydroxy group can be metabolized to the 22-oxo-$\Delta^{23}$-ene functionality in insects and mammals to generate EcR or FXR antagonists.

iv. Furocoumarins and phenylpropanoids. The Earl Grey tea flavoring bergamot oil and its constituent bergamotin, which possesses a geranyl group, both induced CAT activity 8-fold when tested at 25 µM (Table 5 and FIG. 8D). The unprenylated bergamot ingredients bergapten (5-methoxypsoralen) and its hepatocarcinogenic 8-methoxylated psoralen congener were inactive at 50 µM (FIG. 8D). Also, methylenedioxyphenyls like myristicin and apiole in dill and parsley weakly elevated CAT activity 4-fold at 250 µM, but their congener safrole, a rodent liver carcinogen (Miller, E. C. et al., 1983, *Cancer Res.*, 43:1124-34), was inert (FIG. 8E). While the alkenylbenzenes eugenol and caffeic acid were also inactive, methyleugenol, a multi-site rodent carcinogen (Johnson, J. D., et al.,. *J. Agric. Food Chem.* 2000, 48:3620-3632) found in nutmeg and other plants, induced FXR-dependent activity 4 times more than vehicle at this same dose (FIG. 8E).

v. Coumarins and flavanoids. The flavolignin silybin from milk thistle (silymarin) induces macromolecular synthesis in the hepatectomized rodent liver (Fausto, M. and J. Sonnenbichler, 1977, *Hoppe-Seyler's Z. Physiol. Chem.*, 358:141-147), arrests cells in the G$_1$ phase of the cycle (Zi, X. and R. Agarwal, 1999, *Proc. Natl. Acad. Sci. USA*, 96:7490-7495), and shows anti-proliferative effects (Katiyar, S. K. et al., 1997, *J. Natl. Cancer Inst.*, 89:556-66). Silybin increased FXR-dependent activity 18-fold at 50 µM (Table 5). While silymarin lowers cholesterol better than silybin (Krecman, V. et al., 1998, *Planta Med.*, 64:138-42), FXR activity was maximally increased only 4-fold by the former (data not shown). FXR may respond to other analogs of silybin in milk thistle such as silydianin, silychristin or their metabolites. Taxifolin is one silymarin component that has been shown to inhibit HMG CoA reductase activity in hepatocytes (Theriault, A., et al., 2000, *J. Lipid Res.*, 41:1969-1979). FXR was unresponsive to taxifolin or to other flavonoids such as genistein, quercetin, catechins, and gossypetin (50 µM). However, activity was increased 4-fold in response to the same dose of tangeretin, a methoxylated flavone in citrus fruits.

The insecticidal actions of the *derris* plant flavonoid-like component rotenone allegedly result from its ability to inhibit electron transport and respiration (Chance, B., and G. Hollunger, 1963, *J. Biol. Chem.*, 278:418-431). Rotenone also reduces the incidence of spontaneously-arising liver tumors in male mice. These findings animated a test of rotenone as an FXR effector. Rotenone was inactive (FIG. 8F), but its rotenonic acid derivative with a cleaved furan ring, induced FXR-dependent activity 20-fold when added at 20 µM (FIG. 8F). This may have some functional significance since metabolites of rotenone such as 6',7'-dihydro-6',7'-dihydroxyrotenone and 8'-hydroxyrotenone, which are hydroxylated in the proximity of the furan ring, can be generated using microsomal homogenates prepared from either insect or rodent tissues (Fukami, J. I. et al., 1967, *Science*, 155:713-6).

vi. Linoleic acid metabolites. An oil extract of ylang ylang, which emits a jasmine-like aroma, maximally increased FXR-dependent activity 17-fold (Table 5). One of its components, cis-jasmone, a linoleic acid metabolite and defensive signal that is released by plants following herbivore damage (Birkett, M. A. et al., 2000, *Proc. Natl. Acad. Sci. USA*, 97:9329-9334), elicited a 6-fold increase in activity when added at 1 mM (Table 5). An identical dose of jasmonic acid had no effect, but a 17-fold increase was produced by its methyl ester (Table 5). Due to their volatilities, it is anticipated that the high doses of jasmonoids required for FXR activation in cell culture may not correspond to the doses that mediate attractant, repellant, or insecticidal activities in the animal.

vii. Polyketides. Since an extract of hops maximally induced FXR-dependent activity 18-fold, some individual components were tested. The flavanone 8-prenylnaringenin and its methylated isomer isoxanthohumol (20 µM) elicited 38- and 9-fold increases in activity, respectively (FIG. 8G and Table 5). However, FXR was not activated by xanthohumol, the chalcone precursor to isoxanthohumol that is produced during beer brewing (FIG. 8G). Humulone increased activity 8-fold, but lupulone, a structurally-related hops ingredient with an additional isoprenyl group, was inert (Table 5, both tested at 20 µM).

xiii Xanthines. FXR activation by forskolin animated tests of other plant compounds that modulate cAMP levels. FXR-dependent activity was induced 12-fold by 3 mM theophylline or caffeine, but congeners such as theobromine, hypoxanthine, xanthine, adenine, and the cAMP metabolite 5'-AMP were ineffective (FIG. 8H and data not shown). Modest (4-fold) increases in CAT activity were afforded by 8-Br-cAMP or dibutyryl cAMP (1 mM). However, mixing theophylline (3 mM) with 8-Br-cAMP (1 mM) increased activity more than 100-fold like forskolin itself (data not shown). The FXR-activating theophylline dose matches its concentration (4 mM) in tobacco hornworm larvae three days after eating tomato leaves sprayed with 1% theophylline, a dose that reduces leaf consumption by half (Nathanson, J. A., 1984, *Science*, 226:184-7). Given that caffeine and theophylline are present in coffee beans and tea leaves at concentrations that kill *Manduca* larvae, xanthines may function as natural insecticides (Nathanson, J. A., 1984, *Science*, 226:184-7).

In summary, the foregoing experiments indicate that FXR activates transcription in response to a broad range of plant secondary metabolites, which were previously described as insecticides or as modulators of cholesterol or growth in higher metazoans.

E. FXR is Activated by Diverse Class of Man-Made Insecticides

FXR activation by plant-derived JHs and secondary substances provoked tests of man-made insecticides. Its sodium channel-based toxicity notwithstanding (Soderlund, D. M.,: 1985, *Neurotoxicology*, 6:35-46), a pyrethrum extract of chysanthemum flowers maximally induced FXR-dependent activity 13-fold. Candidate active ingredients are the structurally-related cinerins, pyrethrins, and jasmolins since FXR was induced by synthetic pyrethroids (25 µM) including cypermethrin (15-fold induction), permethrin (5-fold induction), phenothrin (8-fold induction), and bioallethrin (14-fold induction) (Table 6).

Organochlorine insecticides (5 µM) such as o,p-DDT (but not p,p-DDT), chlordane, kepone, lindane, dieldrin, and toxaphenes increased CAT activity 3, 7, 12, 5, 17, and 9-fold, respectively (data not shown). Other organochlorines like aroclor 1254 (5 µM) and 2,3,7,8-tetrachlorodibenzo-p-dioxin (100 nM) increased activity 5 and 15-fold, respectively (data not shown). FXR was activated by organophosphates such as malathion, diazinon, chlorpyrifos, and parathion (25 µM) with potencies and efficacies like farnesol (Table 6). Others like ethion and coumaphos were more efficacious and more potent, exhibiting 50- and 16-fold increases in activity, respectively, when tested at 5 µM. Lower molecular weight insecticides phosdrin, carbaryl, and imidan were inactive. Phenylpyrazoles such as chlorfenapyr which lowers ATP levels and structurally-related fipronil that distinctively blocks chloride channels increased FXR-dependent activity 10- and 20-fold, respectively, at 25 µM (FIG. 9). FXR was unaffected by imidacloprid, a nicotine-like compound that interferes with acetylcholine receptor function. These results indicate that FXR may activate transcription in response to structurally-diverse synthetic chemicals that manifest pleiotropic cytotoxicities through equally disparate mechanisms.

F. FXR May be Inhibited or Activated by a Metabolite of the JH Antagonist Precocene Chromene ring-containing precocenes are plant-derived JH antagonists that hasten insect metamorphosis (Bowers, W. S. et al., 1976, *Science*, 193:542-7). Like safrole and other alkenylbenzenes, the precocenes are rodent hepatocarcinogens (Wiseman R. W. et al., 1987, *Cancer Res.*, 47:2275-83). Their alkylation of DNA and proteins and their metabolism to 3,4-diols hinted that precocenes may form reactive epoxides (Brooks, G. T., et al., 1979, *Nature*, 281:570-572; Pratt, G. E., et al., 1980, *Nature*, 284:320-323). To more firmly establish a role for FXR as a functional homolog of an insect JH receptor, precocene could was tested for its ability to function as an FXR antagonist. Instead of acting as an antagonist, precocene I and its 6,7-dimethoxy congener precocene II (both from Sigma-Aldrich) induced FXR-dependent activity 15-fold, but with reduced potencies ($EC_{50}$=150 µM) compared to farnesol. Precocene I was inactive in RAR, RXR, PPAR, or GR-based transcriptional assays, which suggests that it may be relatively specific for FXR (data not shown).

Different lots of precocene induced FXR-dependent activity with varying efficacies, prompting further analysis by thin layer chromatography (TLC). UV-absorbing material eluted from silica was tested for CAT activity and analyzed gas chromatography and mass spectrometry following trimethylsilane derivatization. Non-polar species corresponding to precocene I ($R_f$=0.44; m/z=190) did not affect FXR (FIG. 10A; Polar), but a more polar dimer ($R_f$=0.27; m/z=380) increased activity 22-fold. Its structure was inferred from the observation that FXR was activated by 5,11-dimethyltetrahydrochrysene, but not by its 6,12-dimethyl congener (FIG. 5A) (Meyers, M. J. et al., 1999, *J Med. Chem* 1999, 42:2456-68). The most polar species ($R_f$<0.16) elevated activity 12-fold and had molecular weights consistent with hydroxylated precocenes (FIG. 10A). These likely arose by silica gel-catalyzed air oxidation since they were not detected by GC/MS in the crude sample prior to TLC. Precocene I (25 mg, Sigma-Aldrich, 99% purity) was separated by thin layer chromatography using hexane-ethyl acetate (9:1) as the mobile phase. Aliquots (1× and 3× doses) were tested for FXR effector activity in parallel. In FIG. 10A, precocene carbons are numbered for reference, and the putative structure for the precocene dimer is presented based upon FXR responsiveness (box within graph). One prospective silica gel-catalyzed air oxidation product of precocene (3,4-dihydroxyprecocene) is depicted.

Given that FXR did not respond to the 3,4-diol or its precursor epoxide (data not shown) and that insects and mammals produce other hydroxylated species, experiments were performed to determine whether precocene could be metabolized to some other FXR effector. Incubations with mouse liver microsomes yielded ethyl acetate-extractable material that induced FXR activity 3-fold, which hinted at the presence of some liver activators such as farnesol or bile acids (FIG. 10B). In these experiments, NADPH and either DMSO and 100 µM precocene I were mixed with CD-1 mouse liver microsomes and incubated at 37° C. for one hour. Reaction products were extracted with ethyl acetate, dried, resuspended in DMSO, and tested for FXR effector activity. Parallel microsome incubations with 100 µM of TLC-purified inert precocene I ($R_f$=0.44; m/z=190) generated ethyl acetate-soluble products that reduced this activity by 70%. Since precocene II is O-demethylated (Soderlund, D. M. et al., 1980, *J. Agric. Food Chem.*, 1980, 28:724-731) and 6,7-methylenedioxyprecocene (FIG. 10C) is not a JH antagonist (Bowers, W. S., 1969, Toxicology of the precocenes. In: *Insecticide Mode of Action* Edited by JR Coats. New York: Academic Press; 1969), it was surmised that the 6,7-catechol is the FXR antagonist produced by microsomes. FIG. 10C shows that precocene I and precocene II are metabolically interconverted by methylations and demethylations; also shown is a model (in box) for oxidation (O) and tautomerization of 3,4-dimethoxy-6-isopentenylphenol to a quinone methide and subsequent adduct formation with cellular nucleophiles. Support for this conjecture came from the finding that the FXR activity induced by farnesol was inhibited 44% by 100 µM esculetin, an analog of precocene with a similarly positioned 6,7-catechol (FIG. 10D). In these experiments, increasing amounts of esculetin were added along with 45 µM farnesol to CHO cells transfected with plasmids that express FXR and mouse RXRα, along with a ΔMTV-(EcRE)$_5$—CAT reporter plasmid. Normalized CAT activities are expressed as mean values ± standard deviation calculated from triplicate well samples. The ineffectiveness of esculetin and its analog 7-hydroxy-6-methoxycoumarin as FXR agonists and the ability of 7-methoxycoumarin (all at 1 mM) to increase activity 10-fold emphasize the specificity of congeners. FXR was activated by other precocene-like JH antagonists (FIG. 10C) including 3,4-dimethoxy-6-isopentenylphenol (3-fold induction at 100 µM) and a tricyclic dichromene (29-fold induction at 25 µM). It has been proposed that, like preocene, these suicide substrates disrupt metamorphosis by covalently binding to nucleophilic DNA or proteins following their oxidation to epoxides, catechols, or quinone methides (Bowers, W. S. et al., 1976, *Science*, 217:647-648). Since P450 metabolism may be impaired in cultured cells, it is not entirely unexpected to find that precocene and analogs did not inhibit FXR-dependent activity in the CHO cell-based assay.

Additional experiments were performed to determine whether analogs of precocene function as potential endogenously-produced FXR antagonists. Ubiquinone-1 (U1) with a single isoprene unit is a congener of decaprenylated U10 (coenzyme Q), which functions in electron transport. At 10 µM, U1 completely inhibited farnesol-induced FXR-dependent activity (FIG. 1E). In contrast, di-, tri-, and tetraprenylated ubiquinones (U2, U3, and U4) increased activity 7, 5, and 3-fold, respectively (data not shown). FXR activation by U2 is depicted (FIG. 10F). U6, U8, U9, and U10 were inactive (data not shown). U2, U3, and U4 are detected in bacteria and U6 is found in yeast (Daves, G. D. et al, 1967, *Biochemistry*, 6:2861-2866). However, only U9 and U10 have been reported in insects and mammals (Olson, R. E., 1966, *Vitam Horm.*, 24:551-74). U1, U2, U3, and U4 have not been measured in mammals and hence their physiological significance is not known. Nonetheless, these results illustrate how in situ-generated electrophilic metabolites of precocene may antagonize the effects of JHs via interactions with an FXR homolog in insects.

Example 8

Ecdysone Receptor Activity is Potentiated by JHs and Insecticides

Figure 11A:
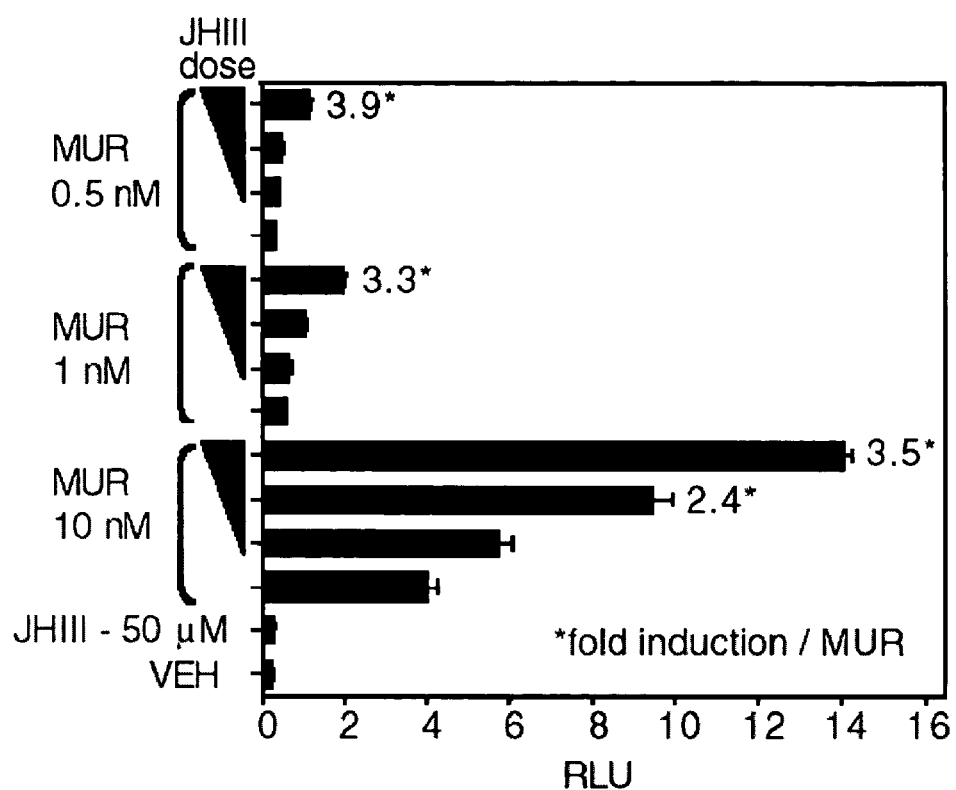
FIG. 11 shows that transcriptional activity programmed by muristerone-primed ecdysone receptors may be potentiated by juvenile hormones and insecticides in accordance with example embodiments of the present invention where: (11A) shows potentiation of ecdysone receptor activity by JH III, where muristerone A (MUR) was added at the indicated doses in ethanol vehicle, and increasing amounts of JH III (12, 25, or 50 µM) were added (underlying triangles), and numbers over bars indicate the ratio of the GEcEc-dependent activity produced by 50 µM JH III in the presence of the indicated dose of MUR to the activity produced by MUR alone; (11B) shows that JH III activity may require both EcR and RXR; (11C) shows that the JH agonist juvocimene from basil may be an EcR effector molecule where muristerone A (0.2 µM) was added alone or with 10 or 20 µM juvocimene (J) to GEcEc-transfected cells, and farnesol (farn) (45 µM) or juvocimene was added to FXR-transfected cells; (11D) shows that insecticides may potentiate EcR-dependent transcriptional activity in the presence (+) or absence (−) of muristerone A, where cells were incubated with the indicated natural and synthetic insecticides (added at 25 µM, except endosulfan which was added at 5 µM), where the numbers above the bars indicate the ratio of activity from cells treated with insecticide plus MUR divided by that treated with MUR alone (fold-induction).
Figure 11B:
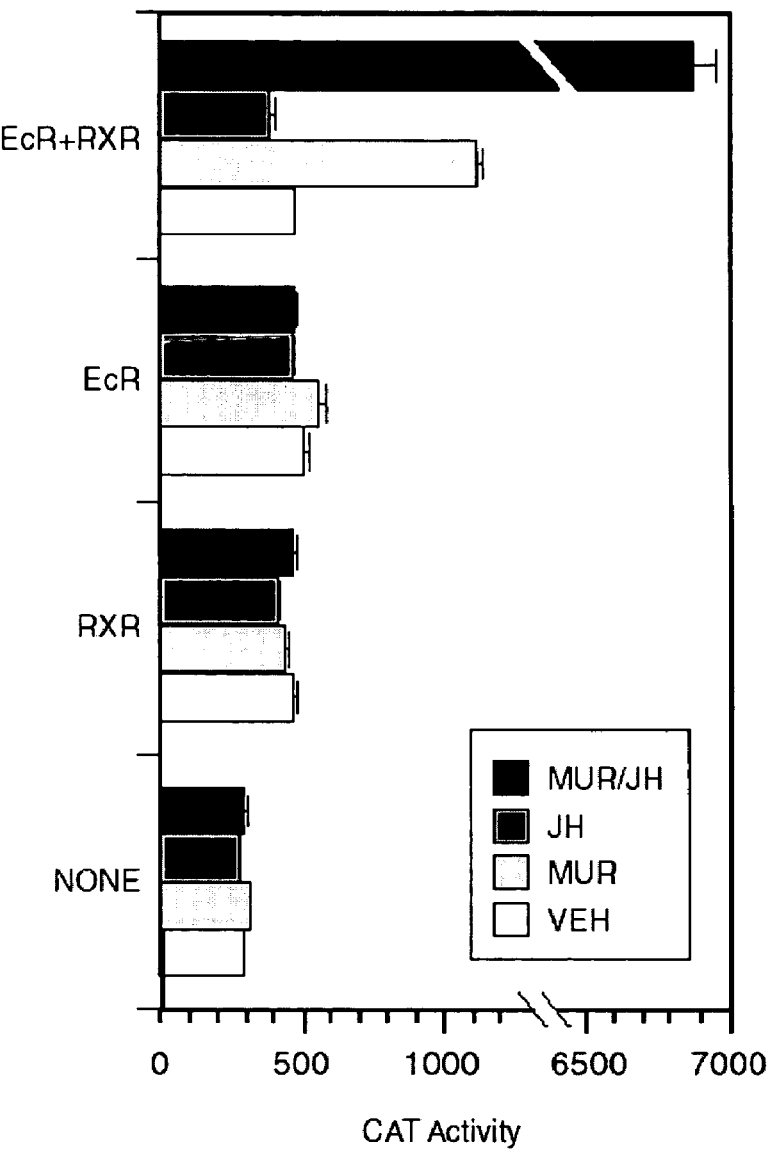

The activation of FXR by natural and synthetic JHs and its inhibition by precocene indicated that FXR may have pharmacological features of a long-postulated insect JH receptor. The prominent candidate for this JH-responsive macromolecule in insects is the structurally-related ecdysone receptor (EcR). Like FXR, EcR heterodimerizes with RXR and binds to the hsp27 ecdysone-responsive DNA element (Forman et al., 1995), but distinctively activates transcription in response to muristerone A (MurA or MUR), a synthetic ecdysone (Yao, T. P., et al., 1992) *Cell*, 71:63-72). Despite these similarities, a MurA-inducible chimeric receptor (GEcEc), constructed by fusing the human glucocorticoid receptor (GR) amino-terminus to the *Drosophila* EcR DNA and ligand binding domains, failed to respond to 80 µM JH III (FIG. 11A). In the experiments shown in FIG. 11A, muristerone A (MUR) was added at the indicated doses in ethanol vehicle, and increasing amounts of JH III (12, 25, or 50 µM) were added (underlying triangles). Numbers over bars indicate the ratio of the GEcEc-dependent activity produced by 50 µM JH III in the presence of the indicated dose of MUR to the activity produced by MUR alone. Relative light units (RLU) from firefly luciferase in cell lysates are expressed relative to *renilla luciferase* (Promega).

Given that JHs modulate ecdysone actions, it was originally anticipated that JH III might antagonize MurA inducible GEcEc-dependent signaling. In contrast, and as discussed above, the GEcEc-dependent transcriptional activity induced by MurA was increased 3-times more by the addition of 80 µM JH III (FIG. 11A). The effect was seen with as little as 0.5 nM MurA, an amount of MurA that barely elevated activity by itself. Similar JH III-mediated increases were afforded by higher doses of MurA (1 and 10 nM, FIG. 11A). Thus, farnesol (45 µM) elicited a 4-fold increase in activity over that provided by MUR alone. In the experiments shown in FIG. 11B, CHO cells were separately transfected with plasmid DNAs that express mouse RXRα or GEcEc (1.25 µg plasmid DNA per well), or transfected with both plasmids or none. MUR was added to cells at 10 nM and JH III at 50 µM. Normalized CAT activity was determined by measuring β-galactosidase activity produced by cotransfected SV40-β-gal plasmid DNA. Note that the ordinate axis is broken. The potentiative effect was also seen using a VP16-*Chironomus* Usp substituted for its mammalian homolog RXR (data not shown). Also, both RXR and GEcEc were essential for activity (11B).

Figure 11C:
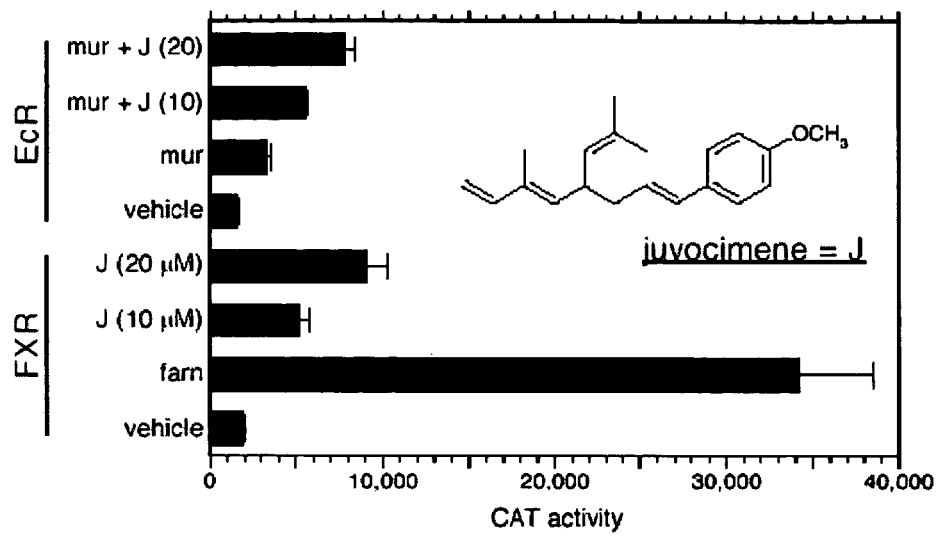

Given that EcR responds to farnesol and JH III, other FXR-activating natural and synthetic JHs and insecticides were tested. For the experiments shown in FIG. 1C, CHO cells were transfected with rat FXR and mouse RXRα or GEcEc and mouse RXRα as described in Methods. Muristerone A (0.2 µM) was added alone or with 10 or 20 µM juvocimene (J) to GEcEc-transfected cells. Farnesol (45 µM) or juvocimene was added to FXR-transfected cells. Mean CAT activity is displayed ± standard deviation from triplicate well samples. Juvocimene, sesamin, and piperonyl butoxide (25 µM) potentiated the MUR-inducible GEcEc-dependent activity between two and four times (FIG. 11C and data not shown).

Figure 11D:
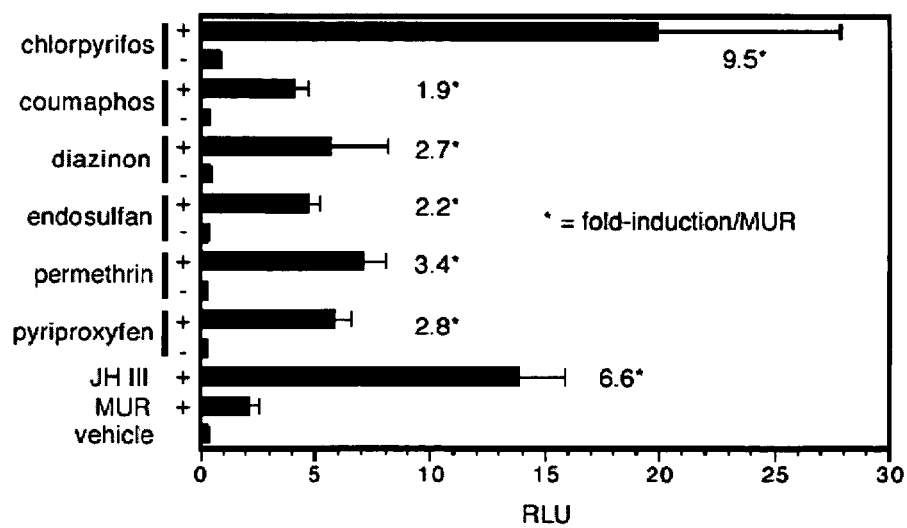

Also, GEcEc-dependent activity was induced between two and three times by other insecticides (25 µM) including diazinon, endosulfan (5 µM), coumaphos, permethrin, and pre-cocene, while 25 µM chlorpyrifos potentiated the MUR response nine times (FIG. 11D). For the experiments shown in FIG. 11D, triplicate wells of CHO cells were transfected with GEcEc and RXR, after which muristerone A (MUR) was added at 10 nM in ethanol vehicle. Cells were incubated with the indicated natural and synthetic insecticides (25 µM), except endosulfan which was added at 5 µM. Plus and negative signs refer to MUR addition. Numbers above bars indicate the ratio of activity from a lysate of cells treated with insecticide plus MUR divided by that treated with MUR alone.

Although FXR and EcR exhibit substantial homology, FXR was unresponsive to muristerone A, ecdysone, or 20-hydroxyecdysone. Reciprocally, the FXR activator chenodeoxycholic acid (CDCA) did not induce GEcEc (data not shown). Thus, it appears that EcR and FXR may both activate transcription in response to natural and synthetic JHs and insecticides, but that the two receptors may not be seamlessly interchangeable.

Example 9

JH and Insecticide Effects Mediated Via FXR and EcR Ligand Binding Domains

The ligand binding domains (LBDs) of nuclear receptors map to their carboxyl termini (Kumar, R. and E. B. Thompson, 1999, *Steroids*, 64:310-9). To ask whether JHs and insecticides transduce their effects via their putative LBDs, chimeric receptors that link the GR DNA binding domain (DBD) to the carboxy-terminal regions of FXR or EcR were examined.

EcR/GR Chimeras

For these experiments, the luciferase reporter construct was used. To obviate influences from other transcription factors, results were normalized using a reporter plasmid from which CAT expression is driven by a minimal promoter consisting of dimerized GREs linked upstream of a 13 base pair TATA box DNA element derived from the adenovirus E1B gene.

Figure 12A:
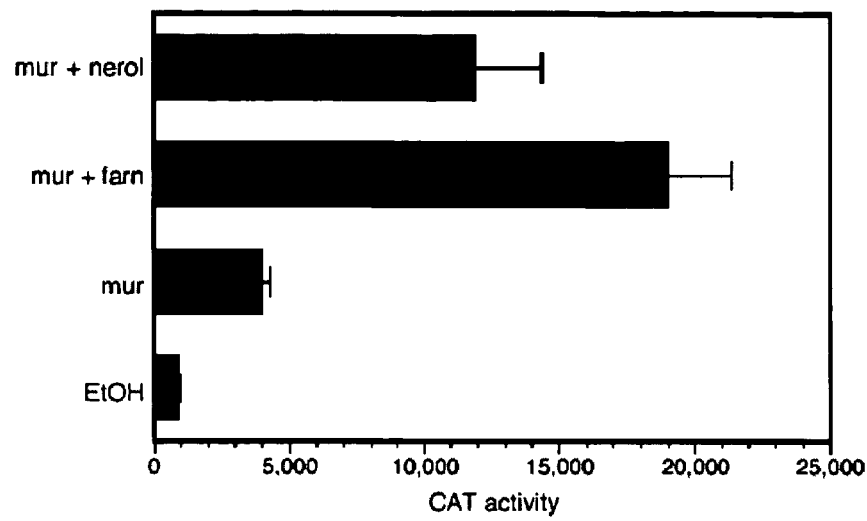
FIG. 12 shows that EcR and FXR ligand binding domains may mediate the transcriptional effects of juvenile hormones and insecticides in accordance with an embodiment of the present invention where: (12A) shows GGEc chimeric receptor activation in the presence or absence of 0.2 µM muristerone A (mur) by farnesol (farn) (25 µM) and its nerolidol isomer; (12B) shows that juvocimene may potentiate muristerone-primed GEcEc and GGEc-dependent activity; (12C) shows that GGEc may mediate the transcriptional effects of the FXR effector ubiquinone-2 (U2); (12D) shows that GGF chimeric receptor-dependent activation is increased by RXR where CHO cells were transfected with the indicated combinations of FXR- or RXR-expressing plasmid DNAs and chenodeoxycholic acid (CDCA) was added at a final dose of 40 µM (+) or is absent (−); and (12E) shows that the chimeric plasmid GGF is activated by the natural and synthetic insecticides cypermethrin, diazinon, dieldrin, precocene, methyl jasmonate, and abietic acid added at final doses of 25 µM.

The MUR-inducible GR/EcR hybrid, GGEc, that fuses the rat GR amino terminus and DBD to the *Drosophila* EcR LBD (Christopherson, K. S., et al., 1992, *Proc Natl Acad Sci USA*, 89:6314-6318) induced transcription between two and four times more with 50 µM farnesol, its isomer nerolidol, or diazinon than with 0.2 µM MUR alone (FIG. 12A). In this experiment, GGEc and RXR were transfected into CHO cells with either a CAT or a luciferase reporter plasmid containing 1.5 kilobase pairs of the glucocorticoid-inducible mouse mammary tumor virus (MTV) promoter. Farnesol was added at 25 µM with or without 0.2 µM muristerone A. Normalized CAT activities are mean ± standard deviation as measured from lysates sampled from triplicate wells. Like GEcEc, this activity required an RXR-expressing plasmid (data not shown).

Figure 12B:
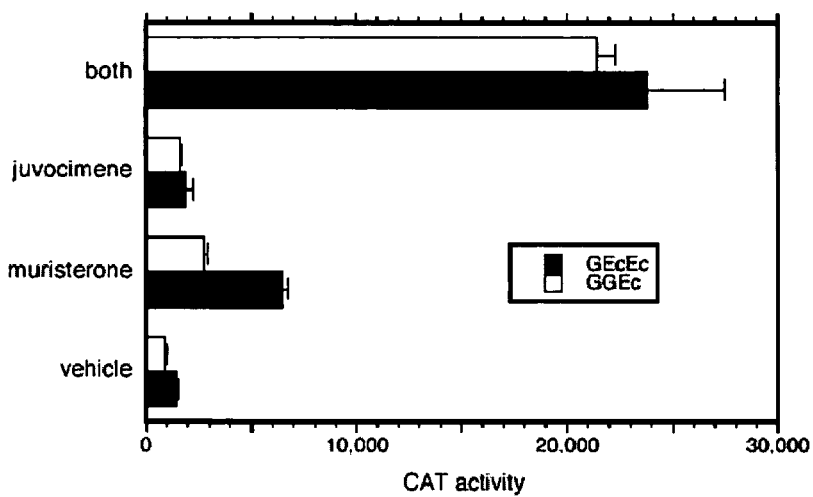

As seen for FXR, GGEc responded to juvocimene (20 µM), the JH mimetic from basil, by increasing activity 7 times more than MUR (FIG. 12B). In these experiments, CHO cells were transfected with a GGEc-expressing plasmid, a mouse RXRα expression plasmid, and an adenovirus E1b TATA-(GRE)$_2$-CAT reporter plasmid. The GGEc plasmid was eliminated from DNA mixtures added to cells transfected in parallel. CAT activities were measured from lysates of cells from triplicate wells treated with ethanol vehicle, juvocimene (20 µM), muristerone A (0.2 µM), or both.

Figure 12C:
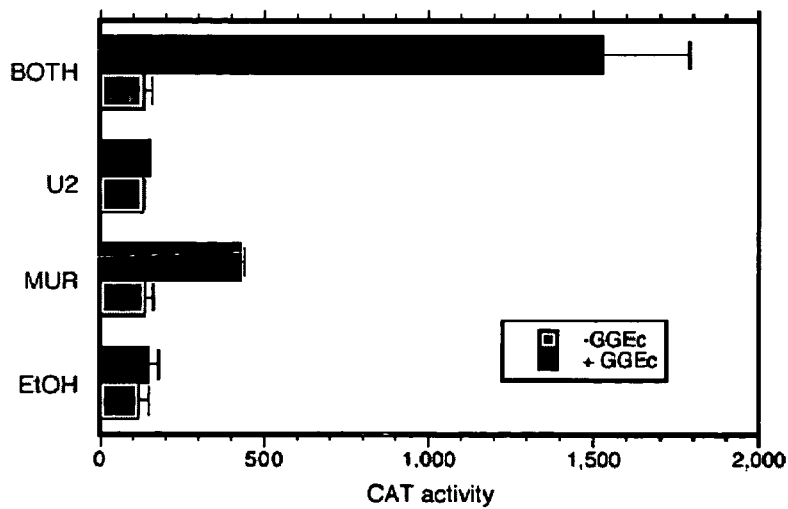

Functional harmony for FXR and EcR was underscored by the observation that the FXR effector ubiquinone-2 (10 µM) similarly increased GGEc-dependent activity 7 times more than MUR (FIG. 12C). In these experiments, CHO cells were transfected with DNAs as described above for the experiment shown in 12B, but ubiquinone-2 (10 µM) was substituted for juvocimene. None of the compounds tested in FIGS. 12A, 12B, or 12C were effective in the absence of ecdysone.

FXR Chimeras

Figure 12D:
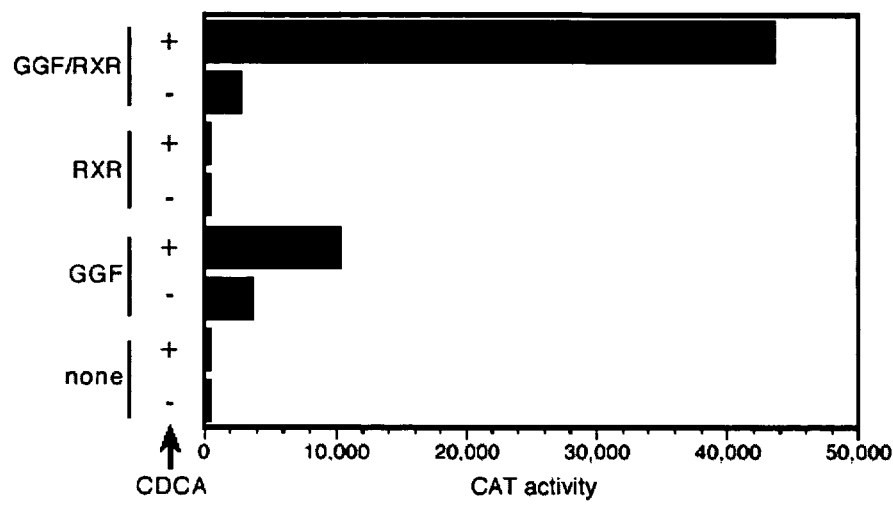

A plasmid was constructed that expresses a hybrid protein (GGF) consisting of the human GR amino terminus and DBD linked to the carboxyl terminus of FXR. GGF-dependent transcriptional activity was increased 3- and 15-fold by farnesol and CDCA (40 µM each), respectively (FIG. 12D). The limited GGF-dependent induction by farnesol was doubled by cotransfecting an RXR-expressing plasmid (FIG. 12D). Importantly, no activity was detectable without GGF.

Figure 12E:
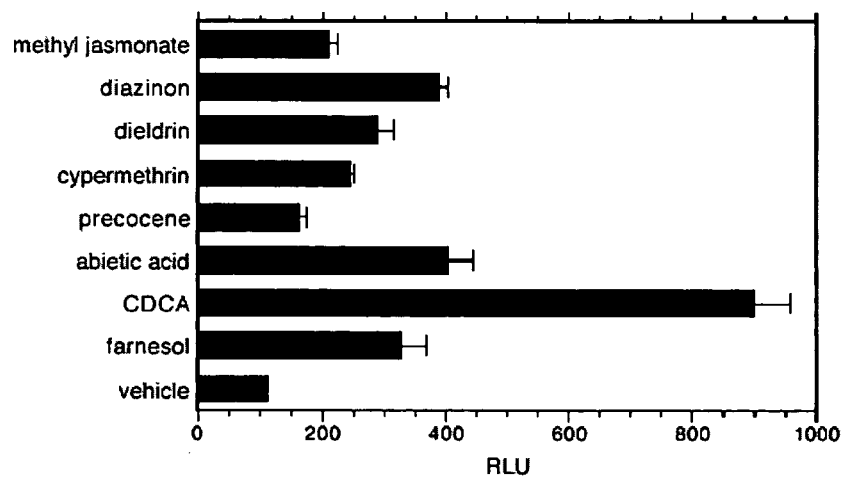

As shown in FIG. 12E, this FXR-like responsiveness led to tests of natural and synthetic insecticides as GGF effectors. In these experiments, CHO cells were transfected with receptor plasmids expressing GGF and mouse RXRα and a luciferase reporter plasmid containing the upstream 1.5 kbp of the MTV promoter. GGF-dependent activity was stimulated between 2- and 7-fold in response to micromolar doses (e.g., 25 µM) of cypermethrin, diazinon, dieldrin, fipronil, piperonyl butoxide, rotenonic acid, cafestol, precocene, methyl jasmonate, and abietic acid (FIG. 12E). Finally, esculetin inhibited CDCA-induced GGF-dependent activity by 54% just as this precocene analog repressed farnesol-induced activity in the assay using native FXR (data not shown). These results indicate that the ligand binding domains of FXR and EcR are required to mediate the transcriptional effects of JHs and insecticides.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness insect population being treated. Likewise, the specific biochemical responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. All references referred to herein are incorporated by reference in their entireties.

What is claimed is:

1. A method for testing the ability of a compound to act as a modulator of insect growth by determining whether the compound potentiates ecdysteroid-activated ecdysone receptor (EcR)-mediated transcription, said method comprising the steps of:
   (a) selecting a compound to be tested for potentiator activity;
   (b) transfecting isolated mammalian cells with:
      (i) an expression vector comprising a nucleotide sequence encoding a functional isoform of an ecdysone receptor (EcR) protein;
      (ii) an expression vector comprising a nucleotide sequence encoding an Ultraspiracle (USP) protein, wherein the USP protein complexes with the EcR protein;
      (iii) a DNA molecule comprising a reporter construct, the reporter construct comprising a reporter gene operably linked to an EcR-hormone response element (HRE);
   (c) adding to each aliquot of the isolated mammalian cells of step (b) an ecdysteroid; or the compound to be tested; or both an ecdysteroid and the compound to be tested;
   (d) measuring whether there is an increase in EcR-mediated transcription in the isolated mammalian cells of step (c) in the presence of both an ecdysteroid and the tested compound, as compared to isolated mammalian cells of step (c) in the presence of an ecdysteroid alone or the tested compound alone;
   (e) performing steps (c)-(d) for various doses of the test compound at various ecdysteroid doses; and
   (f) assessing the ability of the test compound to increase the ability of the ecdysteroid to increase EcR-mediated transcription at sub-maximal doses of the ecdysteroid up to, but not greater than the maximal response evoked by the ecdysteroid.

2. The method of claim 1, wherein the ecdysteroid comprises a hormone.

3. The method of claim 1, wherein the ecdysteroid comprises 20-hydroxyecdysone (20E).

4. The method of claim 1, wherein the ecdysteroid comprises muristerone A (murA).

5. The method of claim 1, wherein the hormone response element is an EcR response element from a promoter of a 27 KDa heat shock protein (hsp 27) gene.

6. The method of claim 1, wherein the functional isoform of the ecdysone receptor comprises at least one of an ecdysone receptor trans-activating domain, an ecdysone receptor DNA binding domain, and an ecdysone receptor ligand binding domain.

7. The method of claim 6, wherein at least one of the ecdysone receptor trans-activating domain, the ecdysone receptor DNA binding domain, and the ecdysone receptor ligand binding domain is from *Drosophila melanogaster*.

8. The method of claim 1, wherein the ability of the test compound to potentiate ecdysteroid-activated EcR-mediated transcription is correlated to the potential insecticidal activity of the test compound.

9. The method of claim 1, wherein the isoform of the ecdysone receptor comprises a *Drosophila* EcRA isoform, a *Drosophila* EcRB1 isoform, or a *Drosophila* EcRB2 isoform.

10. The method of claim 1, wherein the reporter construct comprises a promoter comprising multiple EcR hormone response elements (HREs) linked to a reporter gene encoding a detectable gene product.

11. The method of claim 1, wherein the reporter gene encodes chloramphenicol acetyltransferase (CAT).

12. The method of claim 1, wherein the reporter gene encodes luciferase (LUC).

13. The method of claim 1, wherein the reporter gene encodes green fluorescent protein (GFP).

14. The method of claim 1, wherein the nucleotide sequence encoding the ecdysone receptor (EcR) functional isoform comprises a chimera of DNA from different species.

15. The method of claim 14, wherein the chimera encodes a mammalian activating domain.

16. The method of claim 15, wherein the activating domain is from a glucocorticoid receptor.

17. The method of claim 14, wherein the chimera encodes a mammalian DNA binding domain (DBD).

18. The method of claim 17, wherein the DNA binding domain is from a glucocorticoid receptor.

19. The method of claim 14, wherein the chimera comprises a nucleotide sequence that encodes a viral protein-16 (VP16) activating domain.

20. The method of claim 1, wherein the ecdysteroid comprises ponasterone A, 3-dehydro-20-hydroxyecdysone, ecdysone, or makisterone A.

21. The method of claim 1, wherein the USP comprises a protein encoded by at least one of VP16-dUSPF1, VP16-dUSPF2, or VP16-dUSPF3.

* * * * *